US009889213B2

(12) United States Patent
Caravan

(10) Patent No.: US 9,889,213 B2
(45) Date of Patent: *Feb. 13, 2018

(54) MULTIMODAL IMAGING OF FIBRIN

(71) Applicant: The General Hospital Corporation, Boston, MA (US)

(72) Inventor: Peter D. Caravan, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 65 days.

This patent is subject to a terminal disclaimer.

(21) Appl. No.: 14/954,236

(22) Filed: Nov. 30, 2015

(65) Prior Publication Data

US 2016/0199519 A1    Jul. 14, 2016

Related U.S. Application Data

(63) Continuation of application No. 13/256,795, filed as application No. PCT/US2010/031396 on Apr. 16, 2010, now Pat. No. 9,200,017.

(60) Provisional application No. 61/170,345, filed on Apr. 17, 2009.

(51) Int. Cl.
*A61K 49/00* (2006.01)
*A61K 51/08* (2006.01)
*A61K 49/14* (2006.01)

(52) U.S. Cl.
CPC ........ *A61K 51/088* (2013.01); *A61K 49/0032* (2013.01); *A61K 49/0041* (2013.01); *A61K 49/0056* (2013.01); *A61K 49/14* (2013.01)

(58) Field of Classification Search
CPC ...... A61K 51/00; A61K 51/08; A61K 51/088; A61K 49/00; A61K 49/0032; A61K 49/0041; A61K 49/14; A61K 49/0056; A61K 2121/00; A61K 2123/00
USPC .... 424/1.11, 1.65, 1.69, 1.81, 1.85, 9.1, 9.2, 424/9.3, 9.4, 9.5, 9.6; 514/1, 1.1, 13.6, 514/21.1, 21.4, 21.5, 21.6, 21.7; 530/300, 530/317, 324, 325, 326, 327, 328, 329; 534/7, 10–16
See application file for complete search history.

(56) References Cited

U.S. PATENT DOCUMENTS

| 4,899,755 | A | 2/1990 | Lauffer et al. |
|---|---|---|---|
| 5,021,556 | A | 6/1991 | Srinivasan |
| 5,075,099 | A | 12/1991 | Srinivasan et al. |
| 5,364,613 | A | 11/1994 | Sieving et al. |
| 5,367,080 | A | 11/1994 | Toner et al. |
| 5,672,877 | A | 9/1997 | Liebig et al. |
| 5,720,934 | A | 2/1998 | Dean et al. |
| 5,849,261 | A | 12/1998 | Dean et al. |
| 5,879,658 | A | 3/1999 | Dean et al. |
| 5,886,142 | A | 3/1999 | Thakur et al. |
| 6,549,798 | B2 | 4/2003 | Stefancik et al. |
| 6,898,331 | B2 | 5/2005 | Tiana |
| 6,984,373 | B2 | 1/2006 | Wescott et al. |
| 6,991,775 | B2 | 1/2006 | Koerner et al. |
| 7,110,616 | B2 | 9/2006 | Ditt et al. |
| 7,238,341 | B2 | 7/2007 | Zhang et al. |
| 7,412,279 | B2 | 8/2008 | Weisskoff et al. |
| 8,278,274 | B2 * | 10/2012 | Bussat ............... A61K 49/0043 514/13.6 |
| 9,200,017 | B2 * | 12/2015 | Caravan ............... C07F 9/4006 |
| 2003/0180222 | A1 | 9/2003 | Zhang et al. |
| 2005/0261472 | A1 | 11/2005 | Wescott et al. |
| 2006/0155120 | A1 | 7/2006 | Amedio et al. |
| 2007/0111947 | A1 | 5/2007 | McMurry et al. |
| 2007/0244316 | A1 | 10/2007 | Amedio et al. |
| 2007/0269375 | A1 | 11/2007 | Chen et al. |

FOREIGN PATENT DOCUMENTS

| WO | WO 1991/03200 | 3/1991 |
|---|---|---|
| WO | WO 1995/25119 | 9/1995 |
| WO | WO 1995/28179 | 10/1995 |
| WO | WO 1996/23526 | 8/1996 |
| WO | WO 1997/36619 | 10/1997 |
| WO | WO 1998/18496 | 5/1998 |
| WO | WO 1998/046612 | 10/1998 |
| WO | WO 1998/52618 | 11/1998 |
| WO | WO 1999/017809 | 4/1999 |
| WO | WO 2008/71679 | 6/2008 |

OTHER PUBLICATIONS

Eisenwiener et al., "NODAGATOC, a new chelator-coupled somatostatin analogue labeled with [67/68Ga] and [111In] for SPECT, PET, and targeted therapeutic applications of somatostatin receptor (hsst2) expressing tumors," *Bioconjug Chem.*, 13(3):530-41 (2002).
International Preliminary Report on Patentability issued in PCT/US2010/031396 dated Oct. 18, 2011 (7 pages).
International Search Report and Written Opinion issued in PCT/US1010/031396 dated Dec. 30, 2010 (11 pages).
Loening et al., "AMIDE: a free software tool for multimodality medical image analysis," *Mol Imaging*, 2(3):131-7 (2003).
Merrifield, *J. Am. Chem. Soc.*, 85:2149-2145 (1963).
Nair et al., "Monovalent and bivalent fibrin-specific MRI contrast agents for detection of thrombus, (1963)," *Angew Chem. Int. Ed.*, 47:4918-21 (2008).
O'Brien, T.J., *Epilepsia*, 49:82-89 (2007).
Overoye-Chan et al.,"EP-2104R: a fibrin-specific gadolinium-Based MRI contrast agent for detection of thrombus," *J. Am. Chem. Soc.*, 130:6025-39 (2008).

(Continued)

*Primary Examiner* — D L Jones

(74) *Attorney, Agent, or Firm* — Fish & Richardson P.C.

(57) ABSTRACT

Fibrin-specific imaging agents that contain at least two imaging reporters are described, as well as methods of making and using the contrast agents.

14 Claims, 7 Drawing Sheets

(56) References Cited

OTHER PUBLICATIONS

Rudd et al., "Atherosclerosis inflammation imaging with 18F-FDG PET: carotid, iliac, and femoral uptake reproducibility, quantification methods, and recommendations," *J. Nucl. Med.*, 49(6):871-878 (2008).

Slomka et al., "Quantitative analysis of myocardial perfusion SPECT anatomically guided by coregistered 64-slice coronary CT angiography," *J. Nucl. Med.*, 50:1621-1630 (2009).

Spuentrup et al., "MR imaging of thrombi using EP-2104R, a fibrin-specific contrast agent: initial results in patients," *Eur Radiol.*, 18(9):1995-2005 (2008).

Vymazal et al., "Thrombus imaging with fibrin-specific gadolinium-based MR contrast agent EP-2104R: results of a phase II clinical study of feasibility," *Invest Radiol.*, 44(11):697-704 (2009).

Zhang et al., "A rat model of focal embolic cerebral ischemia," *Brain Res.*, 766(1-2):83-92 (1997).

\* cited by examiner

MULTIMODAL IMAGING OF FIBRIN

CROSS-REFERENCE TO RELATED APPLICATIONS

This application is a continuation of U.S. application Ser. No. 13/256,795, filed May 3, 2012, which is a 371 application of International Application No. PCT/US2010/031396, filed on Apr. 16, 2010, and claims priority to U.S. Application Ser. No. 61/170,345, filed on Apr. 17, 2009, which are incorporated by reference herein in their entirety.

TECHNICAL FIELD

This disclosure relates to fibrin-specific imaging agents having two or more imaging reporters.

BACKGROUND

Fibrin is a major component of blood clots. Fibrin is a fibrillar protein derived from the soluble plasma protein fibrinogen. During the clotting cascade the enzyme thrombin cleaves fibrinopeptides on fibrinogen resulting in an end-to-end polymerization to give the polymer fibrin. The transglutaminase Factor XIII further stabilizes the fibrin mesh by crosslinking the fibrin fibrils. Fibrin is found in all thrombi: fresh thrombus, old thrombus; thrombus in the venous system, arterial system, and cardiac chambers. In this respect fibrin is different from activated platelets which are found mainly in fresh thrombi in the arterial system. Besides thrombus, fibrin is often associated with solid tumors, and is found in the tumor stroma. Fibrin is often associated with complex atherosclerotic plaque where it is believed to be present as a result of plaque rupture or fissure and subsequent healing.

Fibrin is a broadly useful target for imaging. For instance, since fibrin is found in thrombus but not in the circulating blood, a fibrin-targeted imaging would be expected to have high specificity for disease. The concentration of circulating fibrinogen is on the order of 1.5-4.0 g/L (4-12 µM), and one expects similar and higher levels of fibrin in thrombus. High concentrations of fibrin, coupled with its presence in all types of thrombi suggest that a fibrin-targeted imaging would have high sensitivity for disease as well.

Because of the perceived sensitivity and specificity for disease, and the relevance of fibrin in thromboembolic disease, cancer, and vulnerable atherosclerotic plaque, there have been several efforts to develop fibrin-specific imaging probes. This large body of scientific and patent literature speaks to the still unmet medical need of imaging fibrin in order to detect, diagnose, or monitor therapy for thromboembolic diseases and cancer. Despite the innovative approaches to imaging fibrin, there remains room for improvement.

SUMMARY

This disclosure provides peptide-targeted imaging probes that contain at least two imaging reporters. An imaging reporter (IR) is a group that makes the probe visible in a particular imaging modality. For instance, an IR can be a complex of Gd(III) to make the probe detectable by MRI, it can be a radionuclide to make the probe detectable by PET or SPECT imaging, or it can be a fluorophore detectable by optical imaging. The two or more imaging reporters can be the same or can be different. In instances where the imaging reporters differ, it can be possible to detect the probe using two different imaging modalities. Surprisingly, appending different imaging reporters to a short fibrin specific peptide did not affect the affinity of the resultant probe to fibrin.

An imaging agent, or a pharmaceutically acceptable salt form thereof, can include a fibrin binding peptide bound optionally through one or more linkers to two or more imaging reporters, wherein at least one of the imaging reporters comprises the radioisotope of copper-64 ($^{64}$Cu, Cu-64).

A fibrin binding peptide includes any peptide known in the art to have an affinity for fibrin. In some embodiments, the fibrin binding peptide comprises:

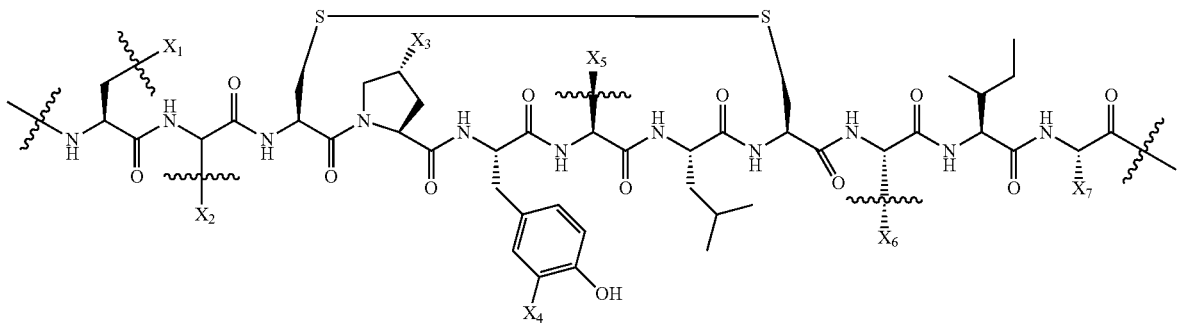

wherein:

$X_1$ is selected from the group consisting of:

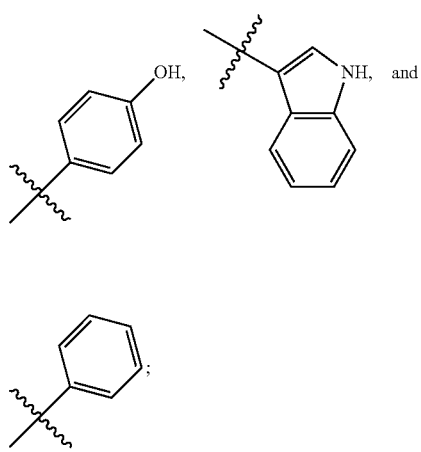

$X_2$ is selected from the group consisting of:

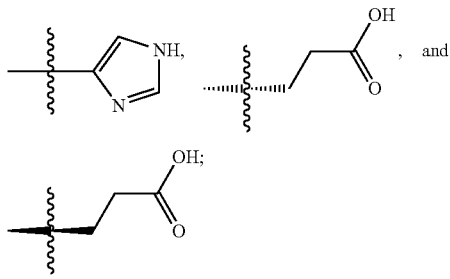

$X_3$ is selected from the group consisting of H and OH;
$X_4$ is selected from the group consisting of H, I, Br, and Cl;
$X_5$ is selected from the group consisting of H and $CH_2COOH$;
$X_6$ is selected from the group consisting of:

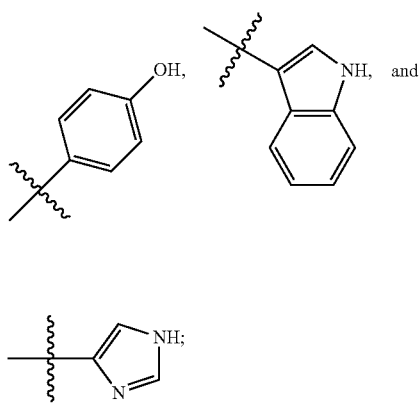

and
$X_7$ is selected from the group consisting of $CH_2CH_2C(O)NH_2$ and $CH_2CH(CH_3)_2$.

Any suitable linker can be used to link an imaging reporter to a fibrin binding peptide. Examples include:
—NHCH(R)C(O)—, wherein R is any natural amino acid side chain;
—NH(CH$_2$)$_n$C(O)—, wherein n is an integer from 1-6;
—NHCH$_2$CH$_2$OCH$_2$CH$_2$C(O)—;
—NHCH$_2$CH$_2$OCH$_2$CH$_2$OCH$_2$CH$_2$C(O)—;
—NHCH$_2$C$_6$H$_4$CH$_2$NH—;
—NH(CH$_2$)$_m$NH—, wherein m is an integer from 2-6;
—NHCH$_2$OCH$_2$NH—;
—NHCH$_2$CH$_2$OCH$_2$CH$_2$NH—; and
—NHCH$_2$CH$_2$OCH$_2$CH$_2$OCH$_2$CH$_2$NH—.

The imaging reporters can be chosen from a chelator comprising a radioactive metal ion, a chelator comprising a paramagnetic metal ion, and a fluorescent dye. The two or more imaging agents can be the same or can be different. In some embodiments, when the imaging reporter includes a chelator, the chelator can be selected from the group consisting of:

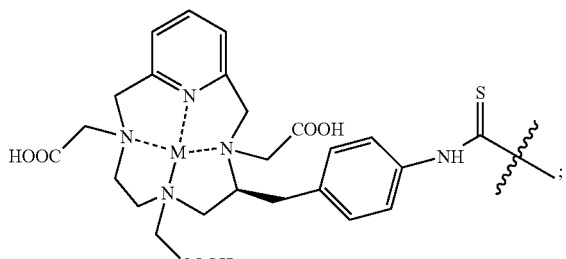

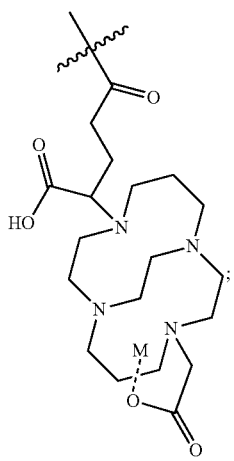

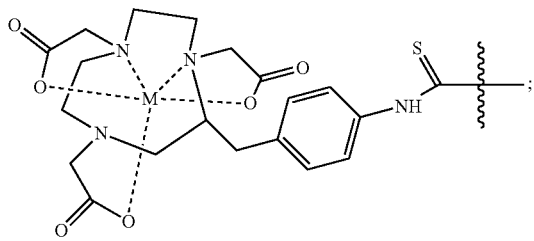

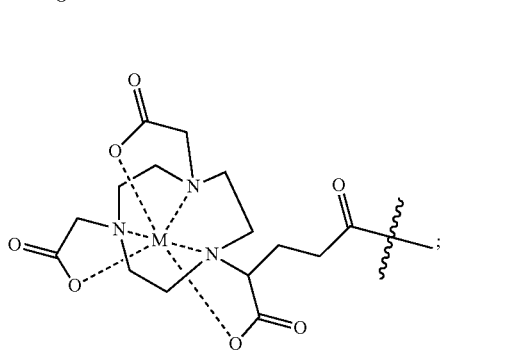

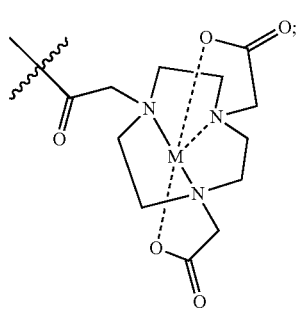

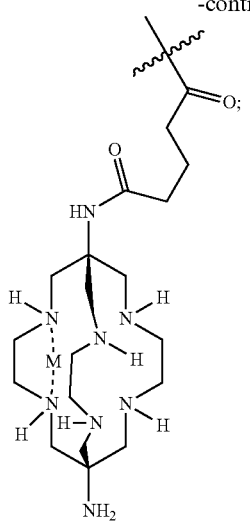

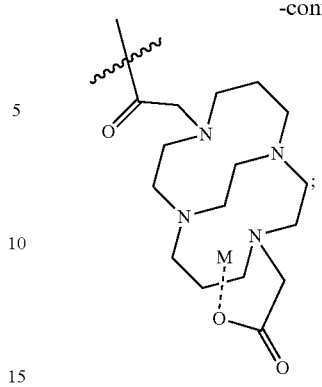

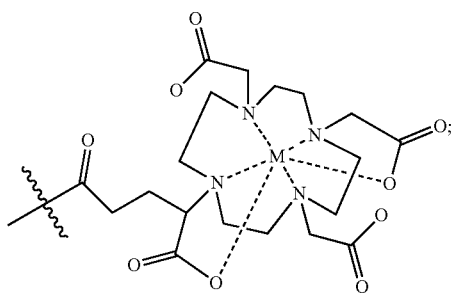

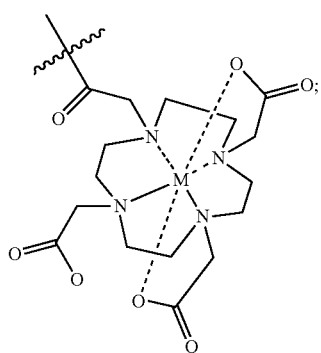

wherein M is a radioactive metal ion or a paramagnetic metal ion. Radioactive metal ions can be, for example, $^{45}$Ti, $^{51}$Mn, $^{52}$Mn, $^{52m}$Mn $^{52}$Fe, $^{60}$Cu, $^{61}$Cu, $^{64}$Cu, $^{67}$Cu, $^{67}$Ga, $^{68}$Ga, $^{72}$As, $^{86}$Y, $^{89}$Zr, $^{94m}$Tc, $^{99m}$Tc, $^{110}$In, $^{111}$In, $^{113}$In, $^{177}$Lu. In some embodiments, the radioactive metal ion can be selected from the group consisting of: $^{52}$Fe, $^{60}$Cu, $^{64}$Cu, $^{67}$Cu, $^{67}$Ga, $^{68}$Ga, $^{72}$As, $^{94m}$Tc, $^{99m}$Tc, $^{110}$In, and $^{111}$In. Paramagnetic metal ions can be, for example, a paramagnetic metal ion having atomic numbers 21-29, 43, 44, and 57-83, such as $Gd^{3+}$, $Mn^{2+}$, $Fe^{3+}$, and $Mn^{3+}$.

An imaging agent can also be a fluorescent dye, such as

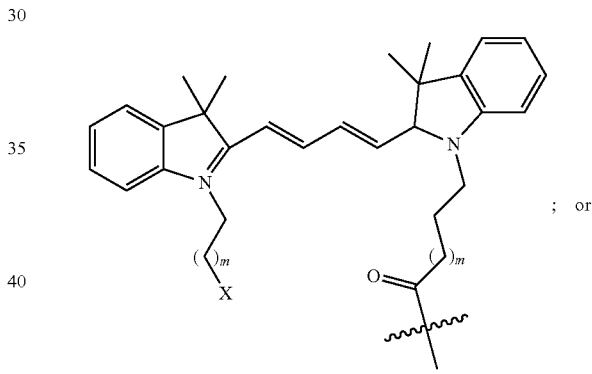

; or

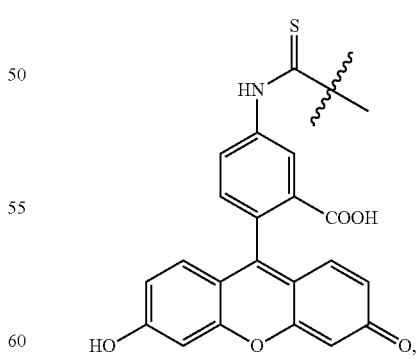

wherein:
n is an integer from 0 to 4;
each m is independently an integer from 0 to 6; and
X is selected from the group consisting of $SO_3^-$, OH, $PO_4^{2-}$.

An example of a fibrin-specific imaging agent includes:

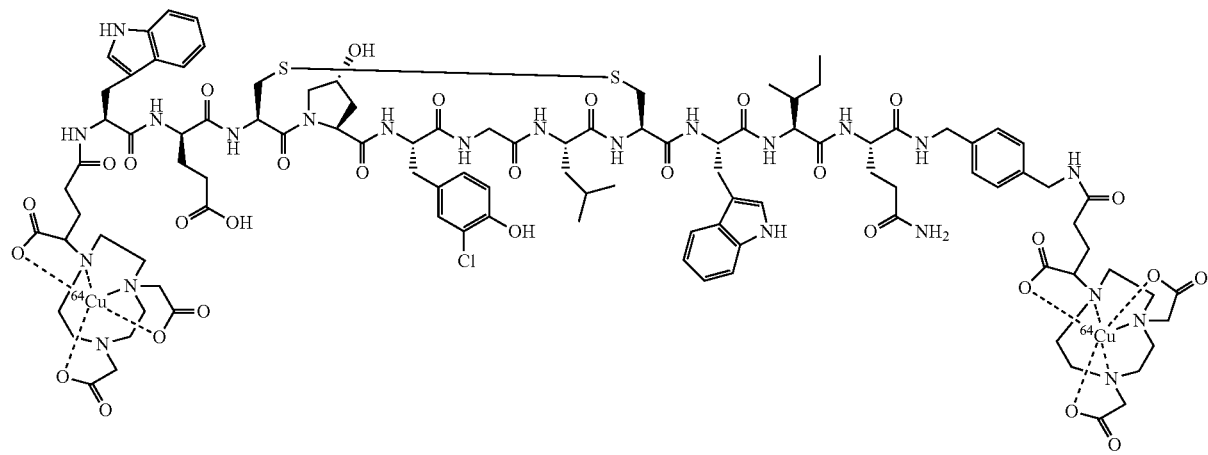

or a pharmaceutically acceptable salt form thereof.

Also provided herein is an imaging agent having the formula

IR$_1$-L$_1$-FTP-L$_2$-IR$_2$ or a pharmaceutically acceptable salt form thereof, wherein:

FTP is a fibrin binding peptide;

L$_1$ and L$_2$ are optional linkers;

IR$_1$ and IR$_2$ are imaging reporters wherein the two imaging reporters are selected from the pairs consisting of: a fluorescent dye and a chelator comprising a radioactive metal ion; a fluorescent dye and a chelator comprising a paramagnetic metal ion; and a chelator comprising a radioactive metal ion and a chelator comprising a paramagnetic metal ion.

For example, the imaging agent can be a compound of the formula:

or a pharmaceutically acceptable salt form thereof, wherein:

X$_1$ is selected from the group consisting of:

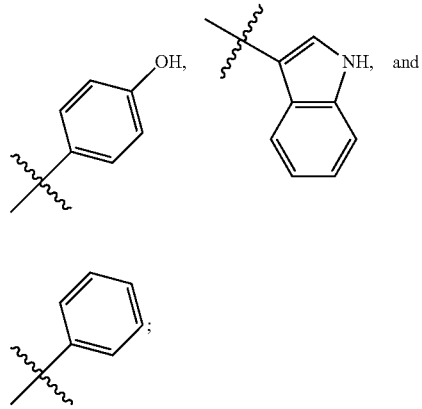

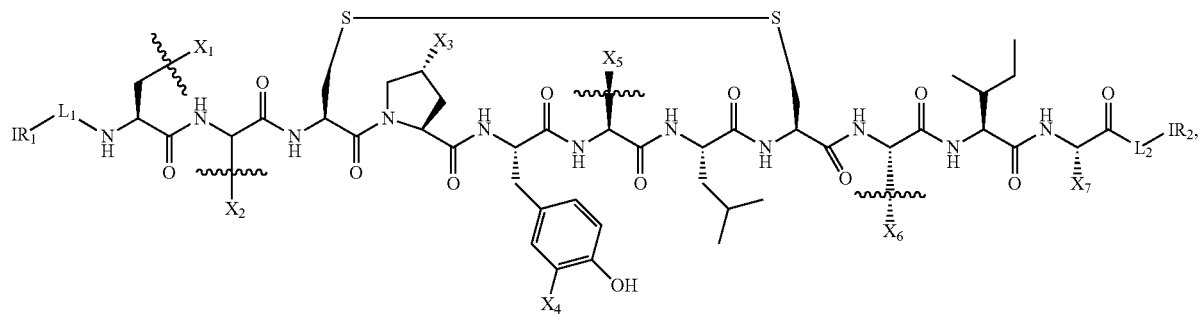

$X_2$ is selected from the group consisting of:

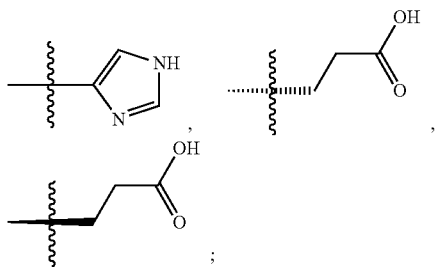

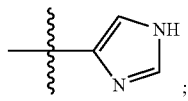

and $X_7$ is selected from the group consisting of $CH_2CH_2C(O)NH_2$ and $CH_2CH(CH_3)_2$.

In some embodiments, $L_1$ can be absent or can be selected from the group consisting of:
—NHCH(R)C(O)—, wherein R is any natural amino acid side chain;
—NH(CH$_2$)$_n$C(O)—, wherein n is an integer from 1-6;
—NHCH$_2$CH$_2$OCH$_2$CH$_2$C(O)—; and
—NHCH$_2$CH$_2$OCH$_2$CH$_2$OCH$_2$CH$_2$C(O)—.

$X_3$ is selected from the group consisting of H and OH;
$X_4$ is selected from the group consisting of H, I, Br, and Cl;
$X_5$ is selected from the group consisting of H and CH$_2$COOH;
$X_6$ is selected from the group consisting of:

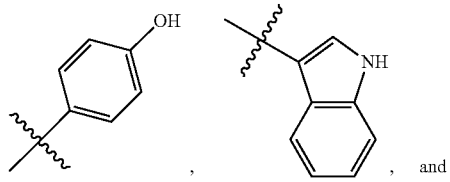

, and

In some embodiments, $L_2$ can be selected from the group consisting of:
—NHCH$_2$C$_6$H$_4$CH$_2$NH—;
—NH(CH$_2$)$_m$NH—, wherein m is an integer from 2-6;
—NHCH$_2$OCH$_2$NH—;
—NHCH$_2$CH$_2$OCH$_2$CH$_2$NH—; and
—NHCH$_2$CH$_2$OCH$_2$CH$_2$OCH$_2$CH$_2$NH—.

Examples of imaging agents having two different imaging reporters include:

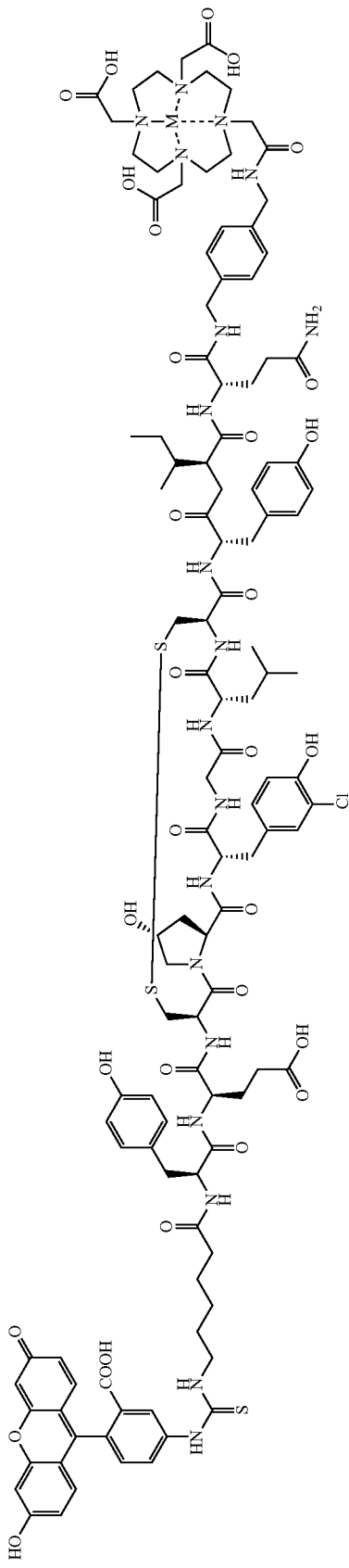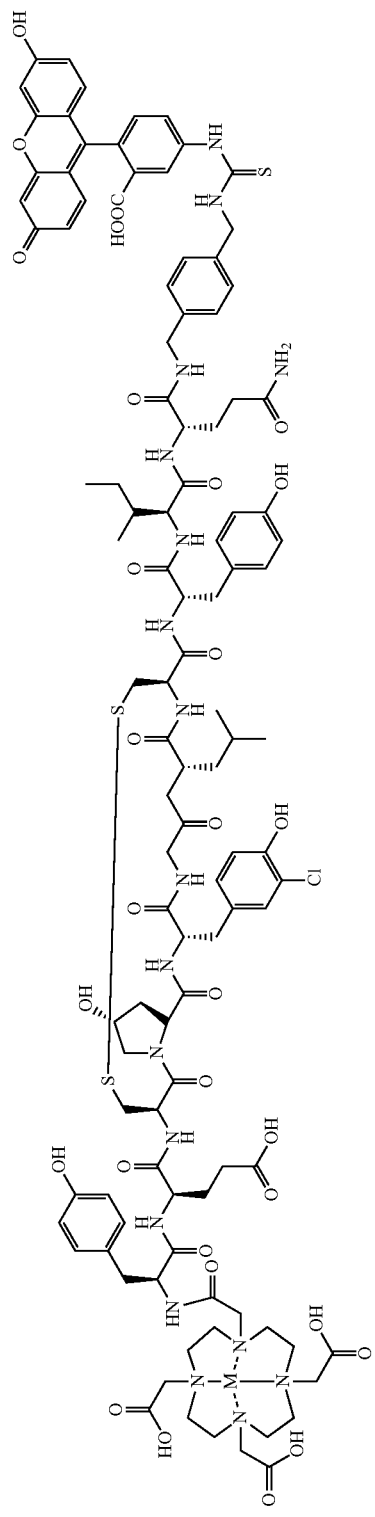
and wherein M is a radioactive or paramagnetic metal ion.

Further provided herein is an imaging agent having the formula:

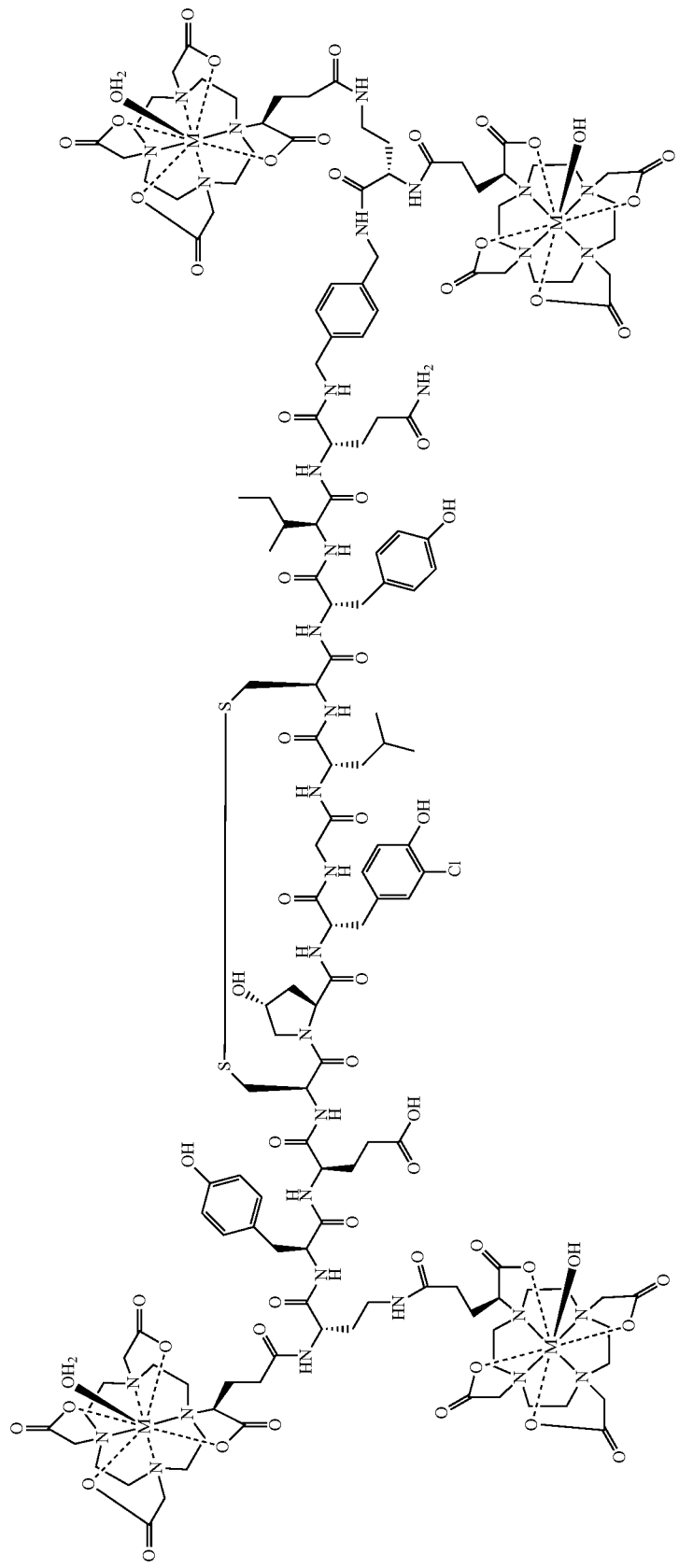

or a pharmaceutically acceptable salt form thereof, wherein:

each M is independently a paramagnetic metal ion or $Gd^{3+}$, with the proviso that no more than three M are $Gd^{3+}$. In some embodiments, at least one M is selected the group consisting of: $^{64}Cu$, $^{68}Ga$, $^{99m}Tc$, and $^{111}In$; for example, at least one M is $^{64}Cu$.

The imaging agents described above can be combined with a pharmaceutically acceptable carrier.

Methods of imaging fibrin in a mammal are also provided. In some cases, the method includes: a) administering to the mammal an imaging agent having at least one chelator comprising a paramagnetic metal ion; b) acquiring an image of the fibrin of the mammal using a nuclear imaging technique (e.g., single photon emission computed tomography and positron emission tomography); c) acquiring an anatomical image of the mammal using magnetic resonance imaging or computed tomography; and d) overlaying the images of steps b) and c) to localize the image of fibrin within the anatomical image of the mammal.

In some embodiments, the images of steps b) and c) are acquired simultaneously. The method can further include administering to the mammal a second imaging agent, wherein the second imaging agent does not target fibrin. For example, the second imaging agent is selected from the group consisting of: gadoteridol, gadopentetate, gadobenate, gadoxetic acid, gadodiamide, gadoversetamide, gadoversetamide, and gadofosveset for use with MRI and iopamidol, iohexol, ioxilan, iopromide, iodixanol, ioxaglate, metrizoate, and diatrizoate for use with CT.

Also provided herein is a method of locating fibrin in a mammal, the method comprising: a) administering to the mammal an imaging agent as described herein; b) acquiring a first and second image of the mammal using two imaging methods selected from 1) nuclear imaging technique, 2) magnetic resonance imaging, 3) computed tomography, and 4) optical imaging (e.g., near infrared imaging), wherein the selected imaging methods are appropriate for the imaging reporters present in the imaging agent of step a). In some embodiments, when optical imaging is used to image the mammal, it is used to obtain the second image. In some cases, the first and second images are acquired simultaneously.

Further provided herein is a kit that includes an imaging agent as described herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
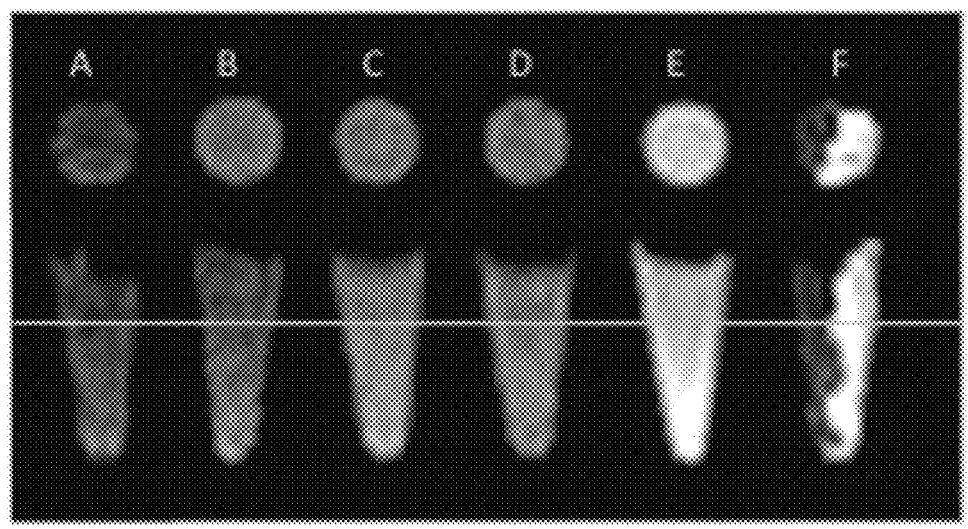
FIG. 1 illustrates phantoms imaged at 1.5 T. Top row are axial slices corresponding to the point indicated by the line through the coronal images (bottom row). A) pure water; B) 5 mg/mL fibrinogen; C) [Gd(HP-DO3A)] at 25 μM in 5 mg/mL fibrinogen; D) [Gd(HP-DO3A)] at 25 μM in 5 mg/mL fibrin gel; E) GdDOTA-cyclic-FBP-p-XD-FITC (compound 17) at 25 μM in 5 mg/mL fibrinogen; F) GdDOTA-cyclic-FBP-p-XD-FITC (compound 17) at 25 μM in 5 mg/mL fibrin gel.

This disclosure provides peptide-targeted imaging probes that contain at least two imaging reporters. An imaging reporter (IR) is a group that makes the probe visible in a particular imaging modality. For instance, an IR can be a complex of Gd(III) to make the probe detectable by MRI, it can be a radionuclide to make the probe detectable by PET or SPECT imaging, or it can be a fluorophore detectable by optical imaging. The two or more imaging reporters can be the same or can be different. In instances where the imaging reporters differ, it can be possible to detect the probe using two different imaging modalities. Surprisingly, appending different imaging reporters to a short fibrin specific peptide did not affect the affinity of the resultant probe to fibrin.

The peptide-targeted imaging probes can be used in a variety of ways to image fibrin. For example, a fibrin-specific imaging agent that contains a radioactive element can be prepared. After administering this radio-labeled fibrin-specific agent, an image can be obtained using a nuclear imaging technique like PET or SPECT that detects the imaging agent directly. A second image can then be obtained to acquire a high resolution anatomical map using either MRI or CT. The images can then be overlaid to localize the low resolution fibrin-targeted image within the high resolution anatomical image.

Another embodiment involves synthesis of a fibrin-specific imaging agent that contains two separate imaging reporters: e.g. a fluorescent dye and a radioactive element, a fluorescent dye and a MR active imaging moiety, or a radioactive element and a MR active imaging moiety. After administering this fibrin-specific agent, two images are obtained using the modalities appropriate to the imaging reporter, e.g. PET and optical.

Fibrin-Specific Imaging Agents

An imaging agent, as provided herein, incorporates a fibrin binding peptide to allow for specific imaging of fibrin (e.g., thrombi, solid tumors, and atherosclerotic plaques) within a mammal. Any peptide capable of binding fibrin may be used. For example, the peptides disclosed in WO 2008/071679, U.S. Pat. Nos. 6,984,373; 6,991,775; and 7,238,341 and U.S. Patent Application No. 2005/0261472 may be used. A peptide can be from about 2 to about 25 amino acids in length (e.g., about 3 to about 20, about 5 to about 18, about 8 to about 15, and about 10 to about 14).

A fibrin binding peptide can have the general formula:

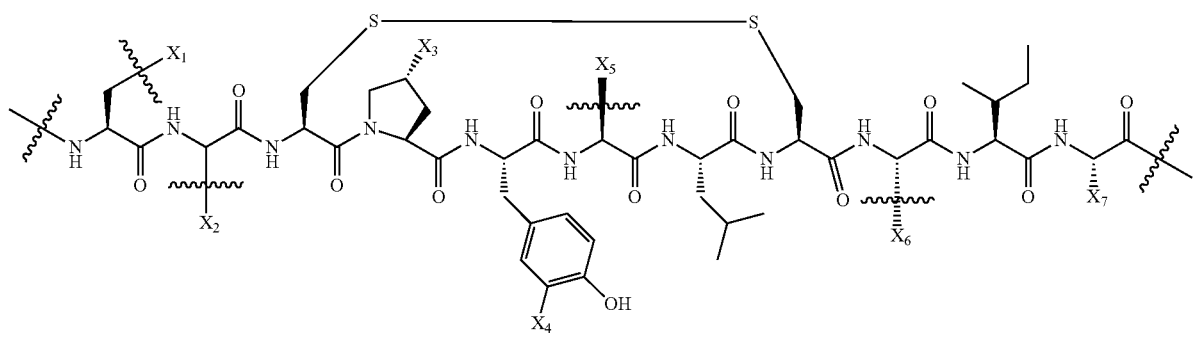

wherein $X_1$ is selected from the group consisting of:

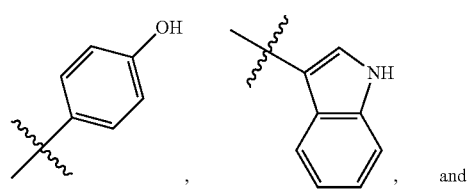

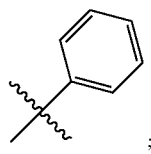

wherein $X_2$ is selected from the group consisting of:

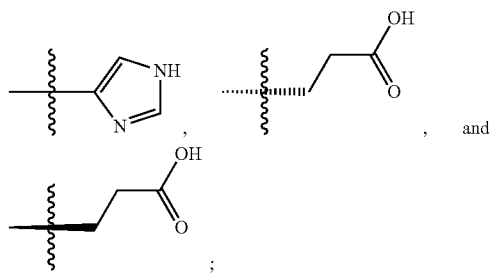

$X_3$ is selected from the group consisting of H and OH; $X_4$ is selected from the group consisting of H, I, Br, and Cl; $X_5$ is selected from the group consisting of H and $CH_2COOH$;

$X_6$ is selected from the group consisting of:

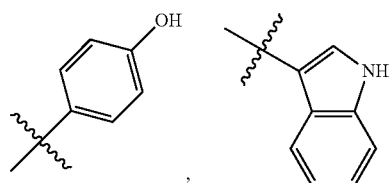

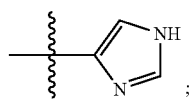

$X_7$ is selected from the group consisting of $CH_2CH_2C(O)NH_2$ and $CH_2CH(CH_3)_2$.

In some embodiments, the fibrin binding peptide can comprise:

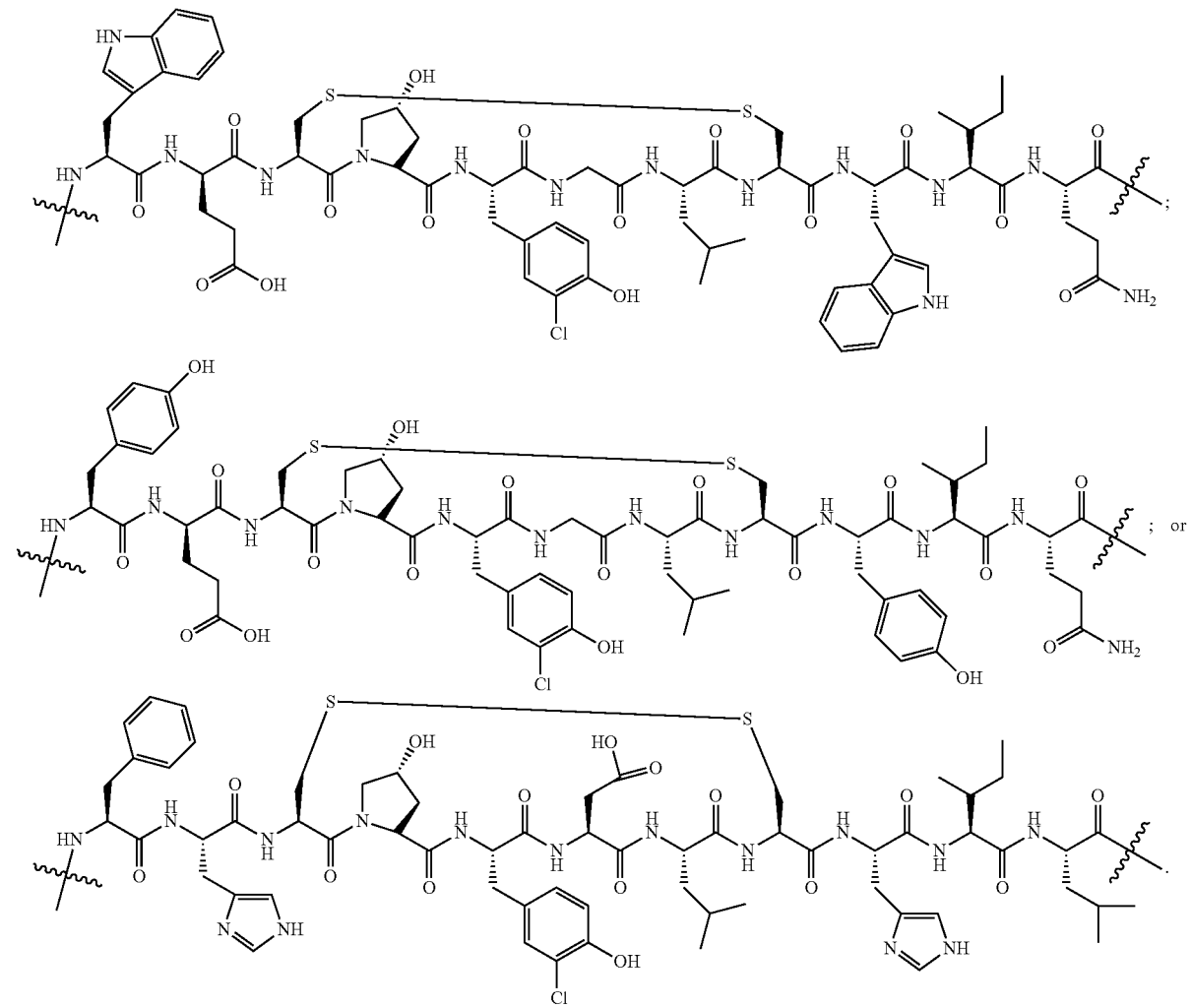

The ability of peptides to bind fibrin can be assessed by known methodology. For example, affinity of the peptide for fibrin can be assessed using the DD(E) fragment of fibrin, which contains subunits of 55 kD (Fragment E) and 190 kD (Fragment DD). The DD(E) fragment can be biotinylated and immobilized via avidin to a solid substrate (e.g., a multi-well plate). Peptides can be incubated with the immobilized DD(E) fragment in a suitable buffer and biding detected using known methodology. See, for example, WO 2001/09188.

Binding can also be assessed in a blood plasma-derived clot assay assay (see e.g. Overoye-Chan et al. *J Am Chem Soc* 2008 130:6025-39). Here, known concentrations of peptide are incubated in blood plasma (human or other species), and thrombin is added to induce clot formation. The clot is separated from the serum, and the concentration of the peptide in the serum ([peptide]free) is determined (e.g. by HPLC or if the peptide is labeled with a fluorophore by fluorescence, or if labeled by a radionuclide concentration is determined by radioactivity). The concentration of fibrin-bound peptide ([peptide]bound) is calculated by subtraction ([peptide]bound)=[peptide]total −[peptide]free).

Binding can also be assessed by a dried fibrin assay. Here, purified fibrinogen (2.5 mg/mL; 7 μM fibrin) is clotted with thrombin and dried to a thin film in wells of a microtiter plate. The resulting clots bind to the plate without loss of protein. The clots are rehydrated with buffer containing known concentrations of peptide. After incubation at 37° C. for 2 hr, the concentration of peptide in the supernatant ([peptide]free) is determined (e.g. by HPLC or if the peptide is labeled with a fluorophore by fluorescence, or if labeled by a radionuclide concentration is determined by radioactivity). The concentration of fibrin-bound peptide ([peptide] bound) is calculated by subtraction ([peptide]bound)=[peptide]total−[peptide]free). A dissociation constant (Kd) for fibrin binding can be determined by fitting a plot of [peptide] bound versus [peptide]free to either a stoichiometric (see e.g. Nair et al., *Angew Chem Int Ed* 2008 47:4918-21) or equivalent binding sites model (see e.g. Overoye-Chan et al. *J Am Chem Soc* 2008 130:6025-39).

Peptides may be synthesized directly using conventional techniques, including solid-phase peptide synthesis, solution-phase synthesis, etc. See, for example, Stewart et al., *Solid-Phase peptide Synthesis* (1989), W.H. Freeman Co., San Francisco; Merrifield, *J. Am. Chem. Soc.*, 1963 85:2149-2145; Bodanszky and Bodanszky, *The Practice of Peptide*

Synthesis (1984), Springer-Verlag, New York. Peptides may also be prepared or purchased commercially. Automated peptide synthesis machines, such as manufactured by Perkin-Elmer Applied Biosystems, may also be used.

The fibrin binding peptide is preferably purified once it has been isolated or synthesized by either chemical or recombinant techniques. For purification purposes, there are many standard methods that may be employed including reversed-phase high-pressure liquid chromatography (RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the fibrin binding peptide may be determined by various methods, including identification of a major large peak on HPLC. A peptide that produces a single peak that is at least 95% of the input material on an HPLC column is preferred. Even more preferable is a peptide that produces a single peak that is at least 97%, at least 98%, at least 99% or even 99.5% of the input material on an HPLC column.

To facilitate imaging of the fibrin, the fibrin binding peptide is detectably labeled with two or more imaging reporters. Each imaging reporter can be independently selected from a chelator comprising a radioactive metal ion, a chelator comprising a paramagnetic metal ion, and a fluorescent dye. In some embodiments, the two or more imaging reporters are the same.

A chelator is a polydentate ligand which is capable of coordinating a radioactive or paramagnetic metal ion. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclotetradecane-1,4,7,10-tetraacetic acid (DOTA), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5Br-EHPG, 5-Me-EHPG, 5t-Bu-EHPG, and 5 sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof, the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl) aminomethylbenzene (MECAM). Additional examples of representative chelators and chelating groups are described in WO 98/18496, WO 86/06605, WO 91/03200, WO 95/28179, WO 96/23526, WO 97/36619, PCT/US98/01473, PCT/US98/20182, U.S. Pat. Nos. 4,899,755 and 6,991,775, and U.S. Patent Application No. 2005/0261472.

In some embodiments, a chelator can be, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, TETA, and bisamino bisthiol (BAT) chelators (see also U.S. Pat. No. 5,720,934). The chelates may be covalently linked directly to the fibrin binding moiety or linked to the fibrin binding moiety via a linker, as described below, and then directly labeled with the metal ion (e.g., paramagnetic or radioactive ion) of choice (see, WO 98/52618, WO 2008/071679, U.S. Pat. Nos. 5,879,658, and 5,849,261).

In some embodiments, a chelator is selected from the group consisting of:

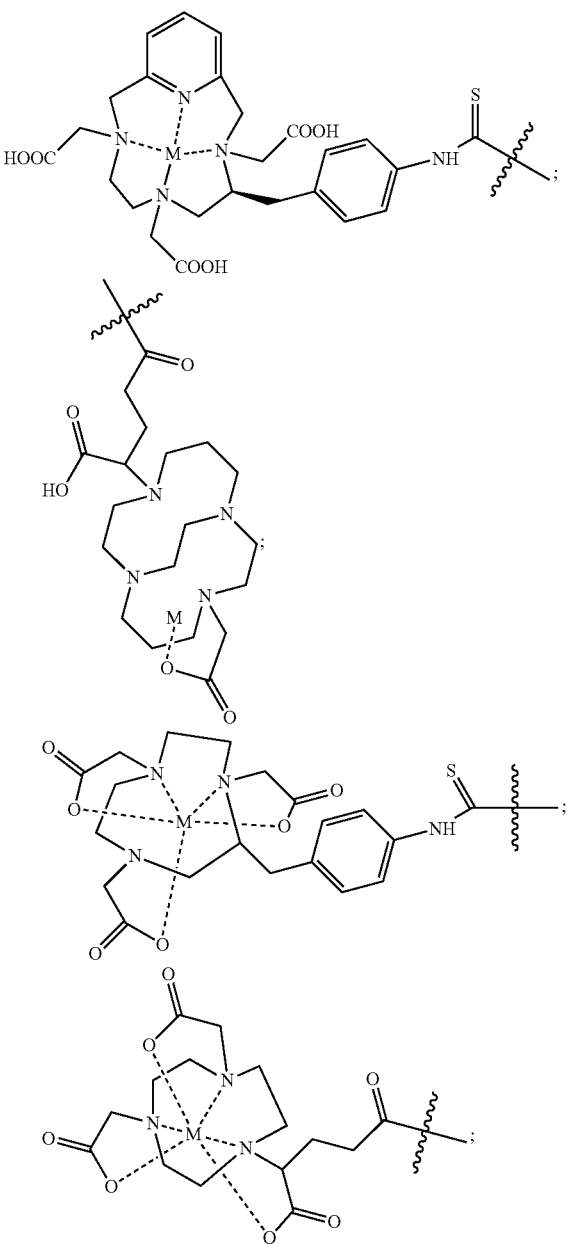

-continued

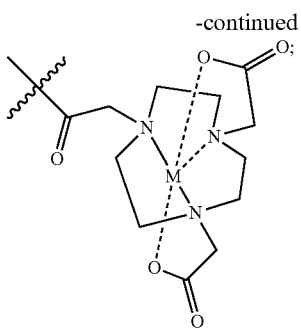

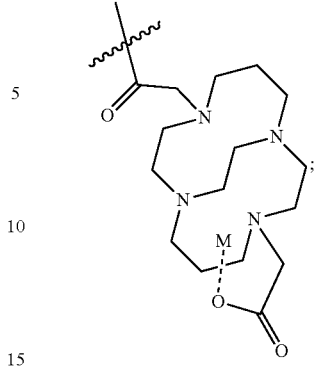

wherein M is a radioactive metal ion or a paramagnetic metal ion. In some embodiments, the chelator is:

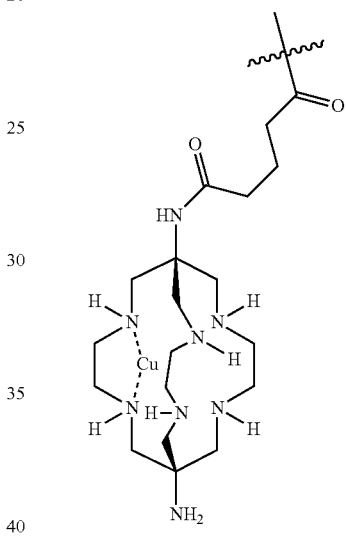

In some cases, a fibrin binding peptide can be labeled with two imaging reporters, wherein the two imaging reporters are selected from the pairs consisting of: a fluorescent dye and a chelator comprising a radioactive metal ion; a fluorescent dye and a chelator comprising a paramagnetic metal ion; and a chelator comprising a radioactive metal ion and a chelator comprising a paramagnetic metal ion.

In some embodiments, a fibrin binding peptide can be labeled with three imaging reporters, wherein two of the imaging reporters are selected from the pairs consisting of a fluorescent dye and a chelator comprising a radioactive metal ion; fluorescent dye and a chelator comprising a paramagnetic metal ion; and a chelator comprising a radioactive metal ion and a chelator comprising a paramagnetic metal ion. In some embodiments, a fibring binding peptide can be labeled with four imaging reporters, wherein two of the imaging reporters are selected from the pairs consisting of a fluorescent dye and a chelator comprising a radioactive metal ion; fluorescent dye and a chelator comprising a paramagnetic metal ion; and a chelator comprising a radioactive metal ion and a chelator comprising a paramagnetic metal ion. In such embodiments with 3 or 4 imaging reporters, the remaining imaging reporter(s) can be selected from any described herein.

The fibrin binding peptide may be conjugated with an imaging reporter agent comprising a chelator comprising a

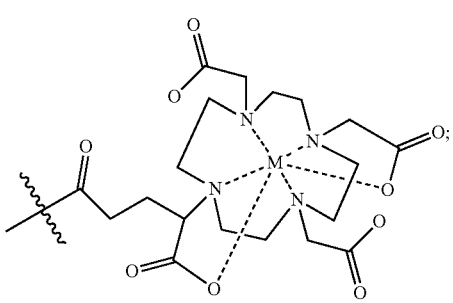

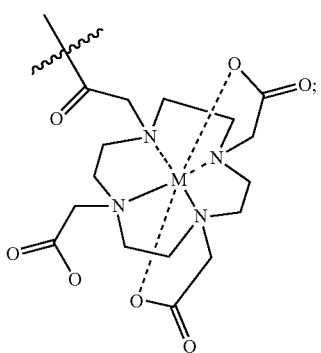

radioactive metal ion appropriate for single photon emission computed tomography (SPECT) and/or positron emission tomography (PET) imaging. A radioactive metal ion can be selected from $^{45}$Ti, $^{51}$Mn, $^{52}$Mn, $^{52m}$Mn $^{52}$Fe, $^{60}$Cu, $^{61}$Cu, $^{64}$Cu, $^{67}$Cu, $^{67}$Ga, $^{68}$Ga, $^{72}$As, $^{86}$Y, $^{89}$Zr, $^{94m}$Tc, $^{99m}$Tc, $^{110}$In, $^{111}$In, $^{113}$In, $^{177}$Lu.

In some embodiments, at least one of the radioactive metal ions is $^{64}$Cu. Copper -64 ($t_{1/2}$=12.7 h; $E(\beta^+)^{max}$=656 keV; $E(\beta^-)^{max}$=573 keV) is a useful radionuclide for PET applications. The longer half-life of $^{64}$Cu relative to other positron emitting isotopes like $^{11}$C (20 min) means no onsite cyclotron is required for production. Thus $^{64}$Cu can be shipped to users all over the country. An additional benefit to $^{64}$Cu is that the $^{64}$Cu label is introduced in the ultimate synthetic step via a highly thermodynamically favored chelation reaction which leads to higher specific activity and potentially no requirement for final HPLC purification. The long half-life and potential ease of preparation mean that Cu-64 based molecular imaging probes have the potential to be more widely available to the nuclear medicine community, either in a kit form where the end user mixes the $^{64}$Cu with a probe precursor to formulate the probe or if the formulated probe is delivered by a centralized supplier. $^{64}$Cu is a particularly useful isotope for fibrin imaging. In human clinical trials with a fibrin-targeted MR probe it was found that imaging was best 2 to 24 hrs post injection of the probe (see, e.g., Vymazal J. et al., *Invest Radiol.* 2009 44(11):697-704; and Spuentrup E. et al., *Eur Radiol.* 2008 18(9): 1995-2005). For a PET application it is preferred to use a radionuclide whose half-life is similar to the biological time scale.

A paramagnetic metal ion can be conjugated to a fibrin binding peptide through a chelating group. Examples of suitable paramagnetic metal ions include, but are not limited to, those metal ions having atomic numbers 21-29, 42, 44, or 57-83. This includes ions of the transition metal or lanthanide series which have at least one (e.g., at least two, at least four, at least five) unpaired electrons and a magnetic moment of at least 1.7 Bohr magneton. In some embodiments, a paramagnetic metal ion is selected from the group consisting of Gd(III), Fe(III), Mn(II and III), Cr(III), Cu(II), Dy(III), Tb(III), Ho(III), Er(III), and Eu(III). For example, a paramagnetic metal ion can be Gd(III), Mn(II), or Mn(III).

A fibrin binding peptide can also be conjugated to a fluorescent dye. Examples of fluorescent dyes include, but are not limited to, fluorescein and derivatives thereof (e.g., fluorescein isothiocyanate (FITC)), Alexa 488, Alexa 532, cy3, cy5, 6-joe, EDANS, rhodamine 6G (R6G) and derivatives thereof (e.g., tetramethylrhodamine (TMR), tetramethylrhodamine isothiocynate (TMRITC), and x-rhodamine), Texas red, BODIPY FL (Molecular Probes Corporation, U.S.A.), BODIPY FL/C3, BODIPY FL/C6, BODIPY 5-FAM, BODIPY TMR, and their derivatives (e.g., BODIPY TR, BODIPY R6G, and BODIPY 564) Dapoxyl® dyes, PyMPO derivatives (PyMPO maleimide, PyMPO-OSu), Prodan and derivatives (BADAN, Acrylodan), Dansyl derivatives (IAEDANS, Dansyl chloride), NDB derivatives (NBD-Cl, IANBD), Coumarin and derivatives (MDCC, DACIA, DACITC, CPM), Merocyanine derivatives (Merocyanine 540), amd Dimethylaminophthalimides (4-DMAP, 4-DMN, 6-DMN).

In some embodiments, a fluorescent dye is selected from the group consisting of:

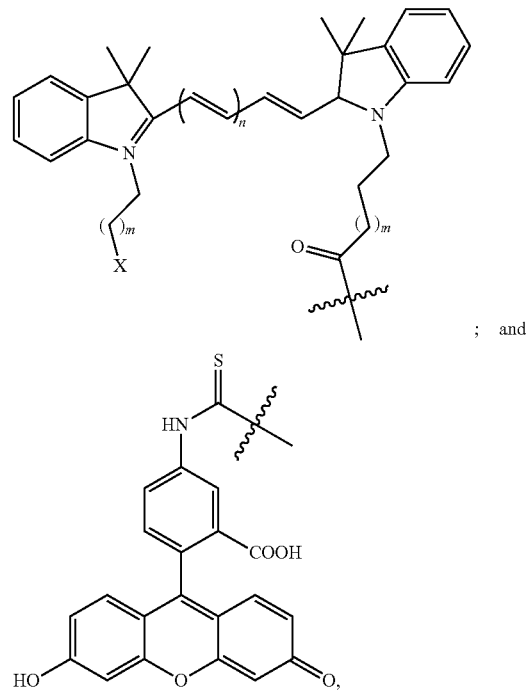

; and wherein:

n is an integer from 0 to 4;

each m is independently an integer from 0 to 6; and

X is selected from the group consisting of $SO_3^-$, OH, $PO_4^{2-}$.

The imaging reporters described herein may be directly bound to the fibrin binding peptide or conjugated through a linker moiety. A linker can be used to covalently attach one or more imaging reporters to the peptide terminus. The linker may be branched or unbranched and may comprise multiple functional groups for imaging reporter attachment. Linkers, if present, typically are relatively small and rigid for the imaging agents described herein. For example, a linker can have a molecular weight less than about 350 (e.g., less than about 200).

In some embodiments, a linker is independently selected from the group consisting of:

—NHCH(R)C(O)—, wherein R is any natural amino acid side chain;

—NH(CH$_2$)$_n$C(O)—, wherein n is an integer from 1-6;

—NHCH$_2$CH$_2$OCH$_2$CH$_2$C(O)—;

—NHCH$_2$CH$_2$OCH$_2$CH$_2$OCH$_2$CH$_2$C(O)—;

—NHCH$_2$C$_6$H$_4$CH$_2$NH—;

—NH(CH$_2$)$_m$NH—, wherein m is an integer from 2-6;

—NHCH$_2$OCH$_2$NH—;

—NHCH$_2$CH$_2$OCH$_2$CH$_2$NH—; and

—NHCH$_2$CH$_2$OCH$_2$CH$_2$OCH$_2$CH$_2$NH—.

In some cases, a fibrin-specific imaging agent comprises a fibrin binding peptide bound optionally through one or more linkers to two or more imaging reporters. In some embodiments, at least one of the imaging reporters comprises $^{64}$Cu. Examples of imaging agents include:

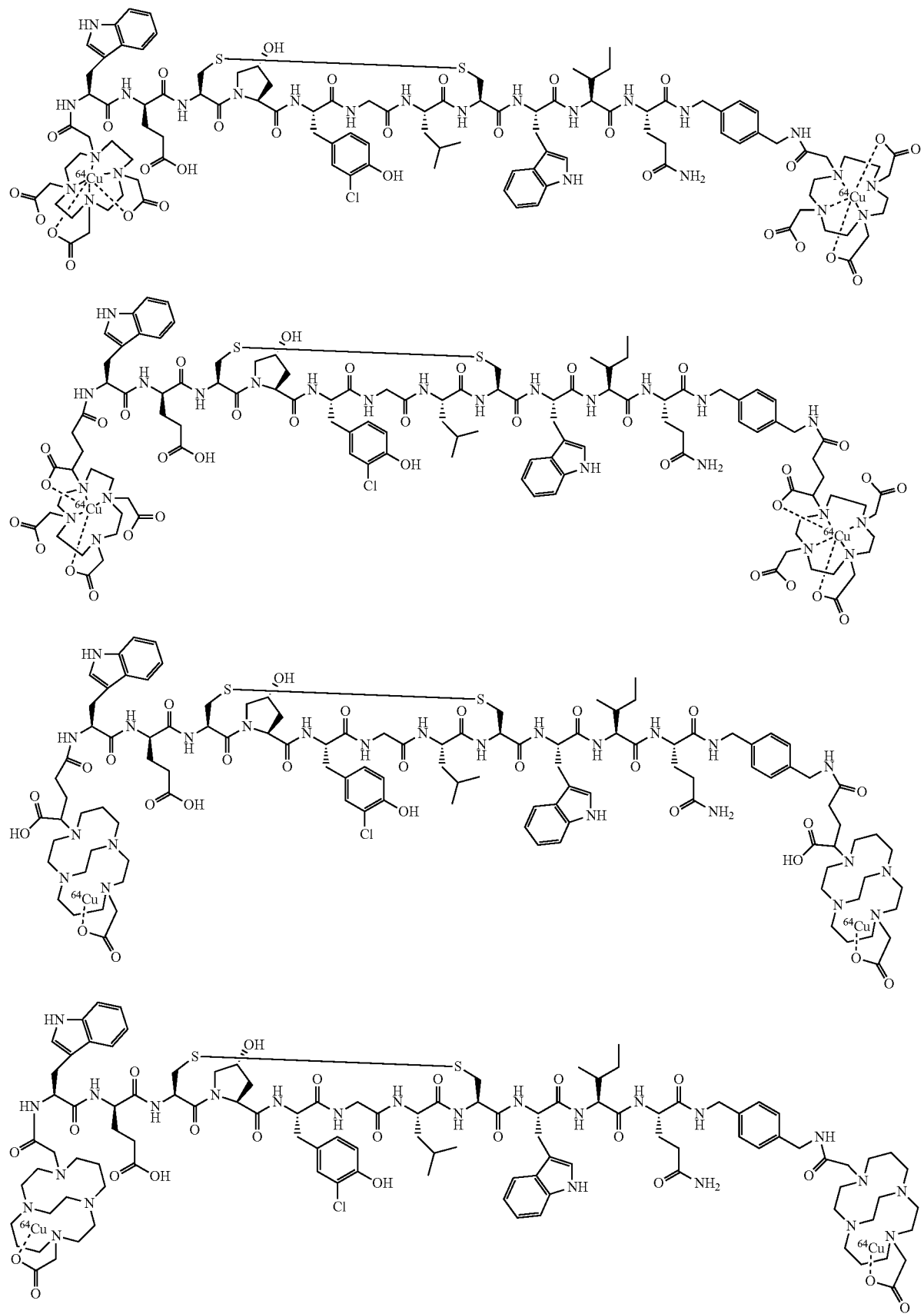

-continued
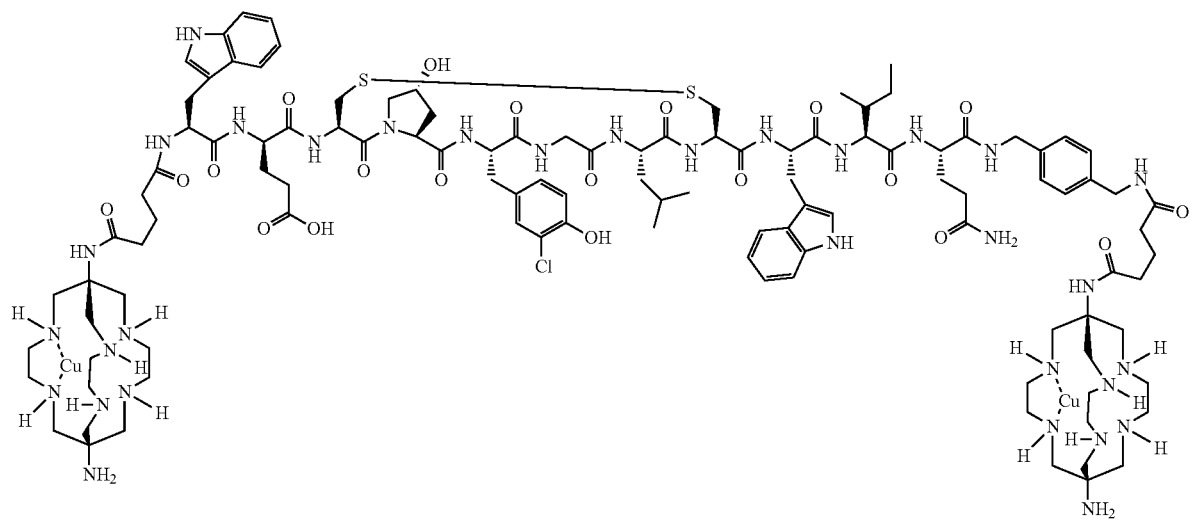
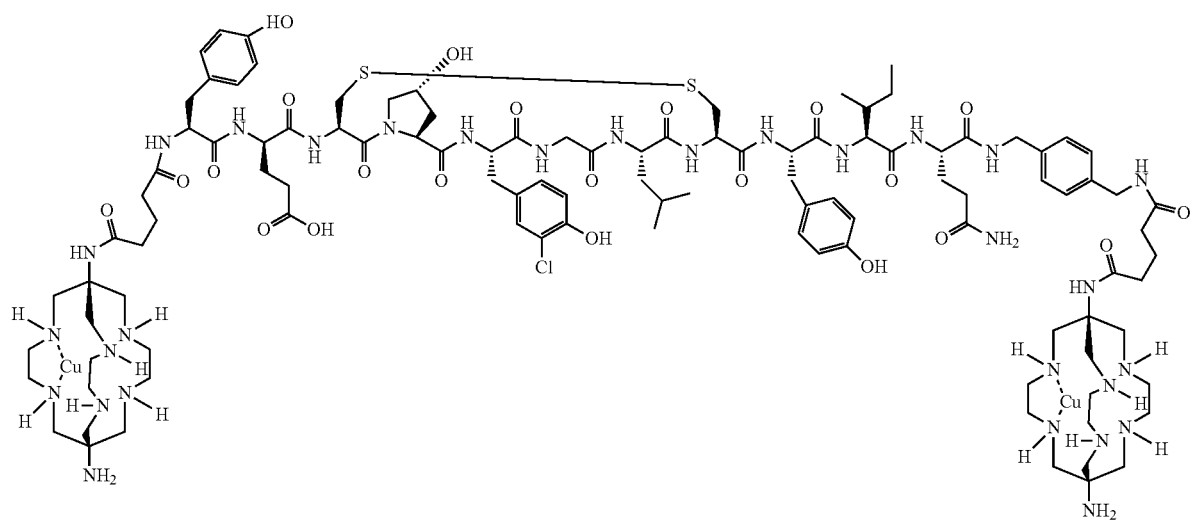
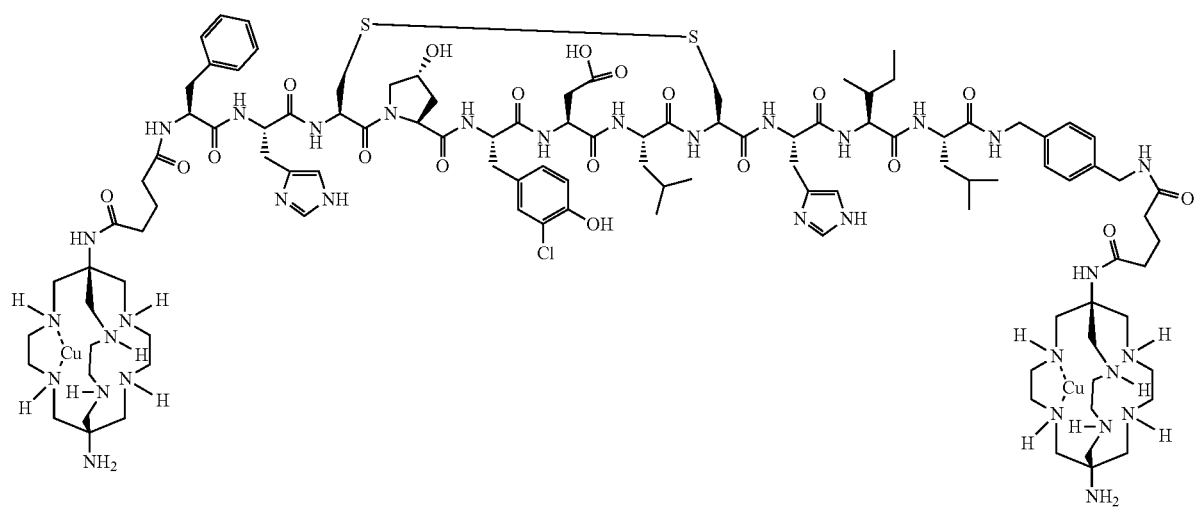

-continued
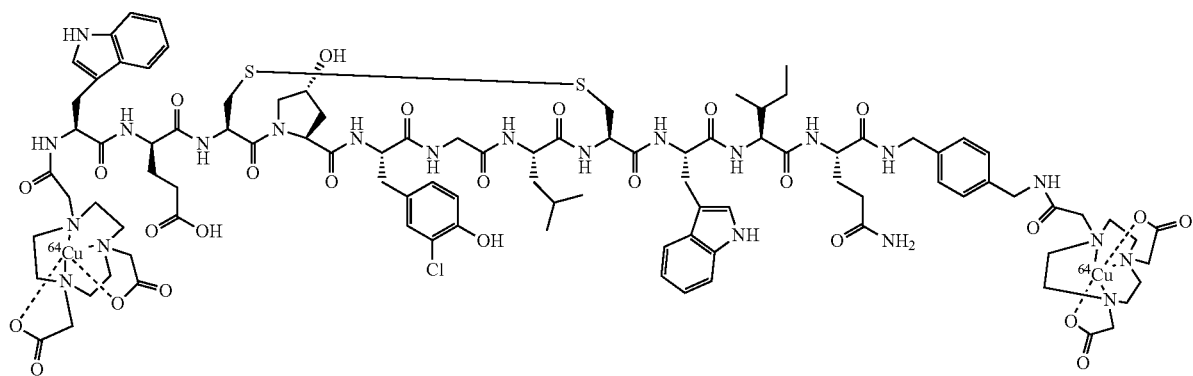
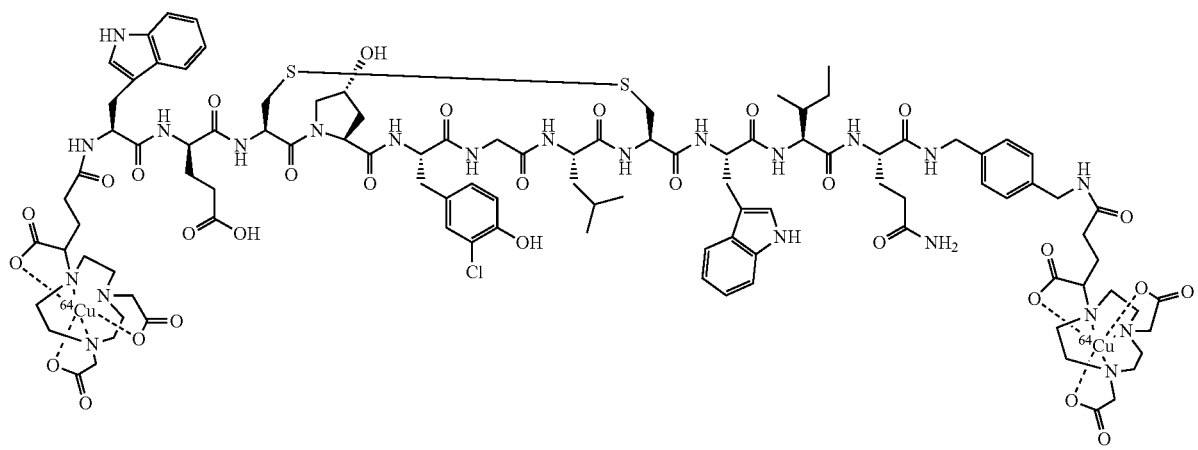
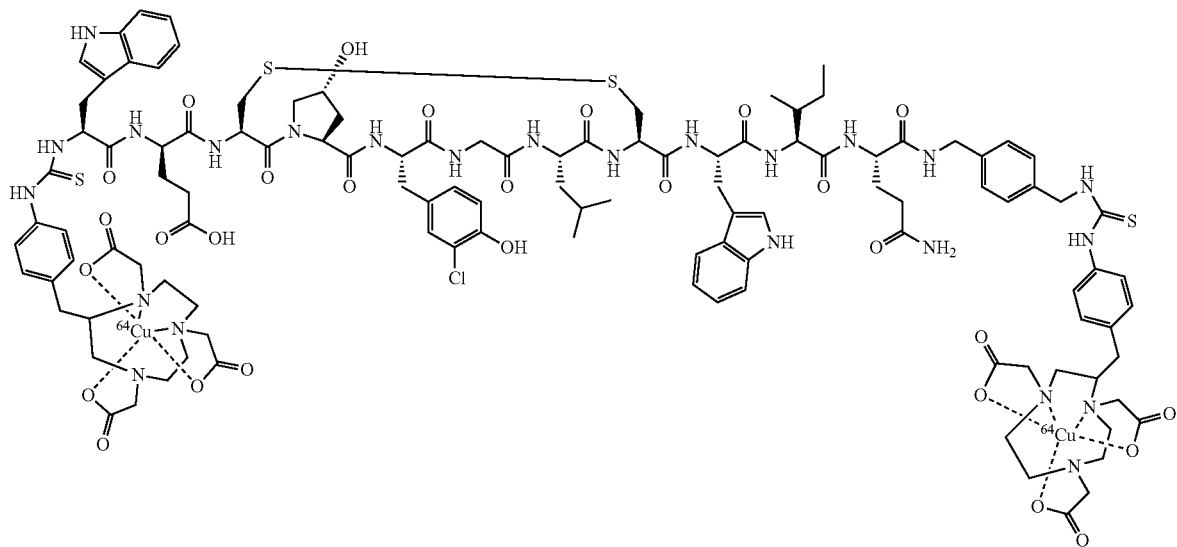

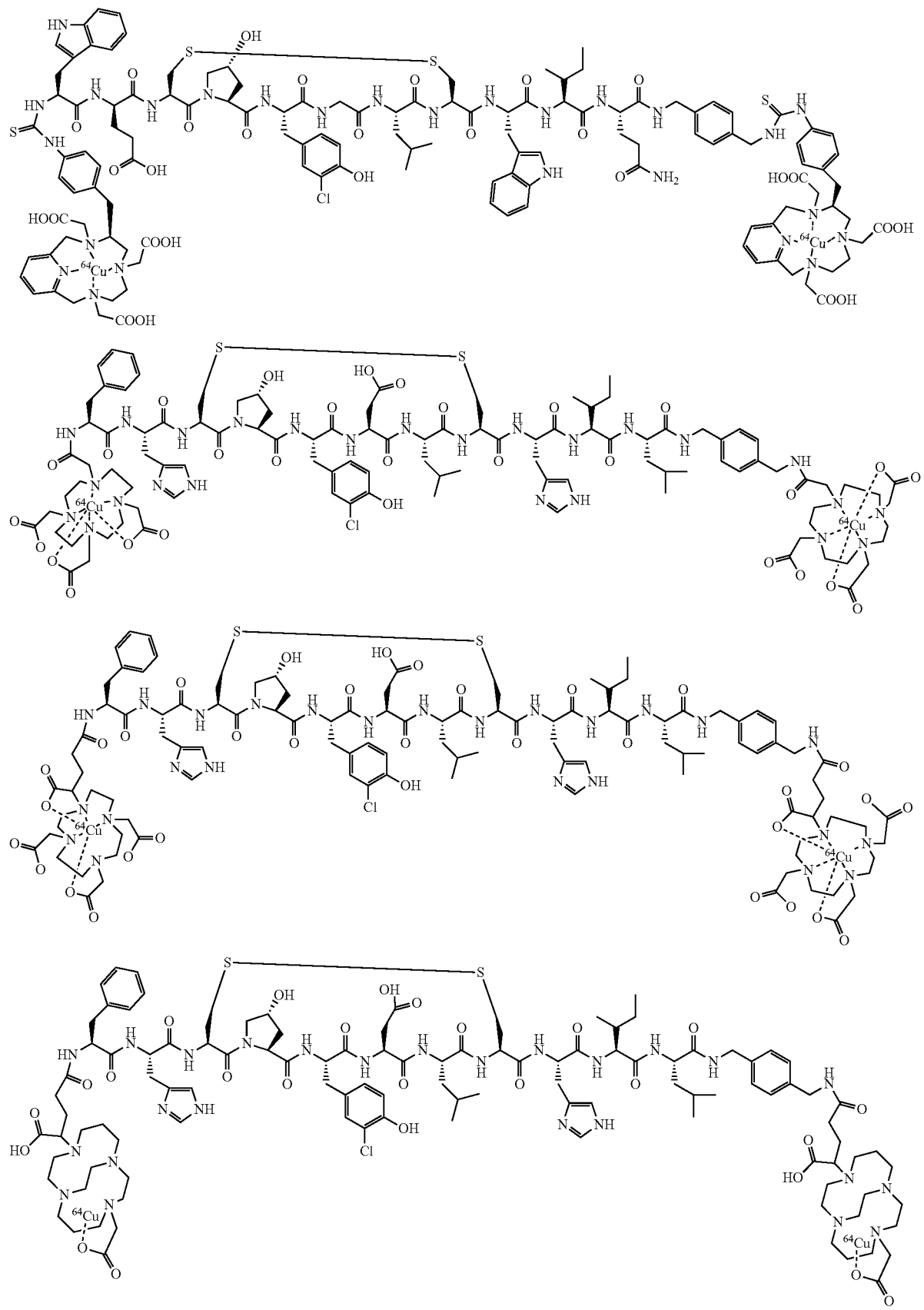

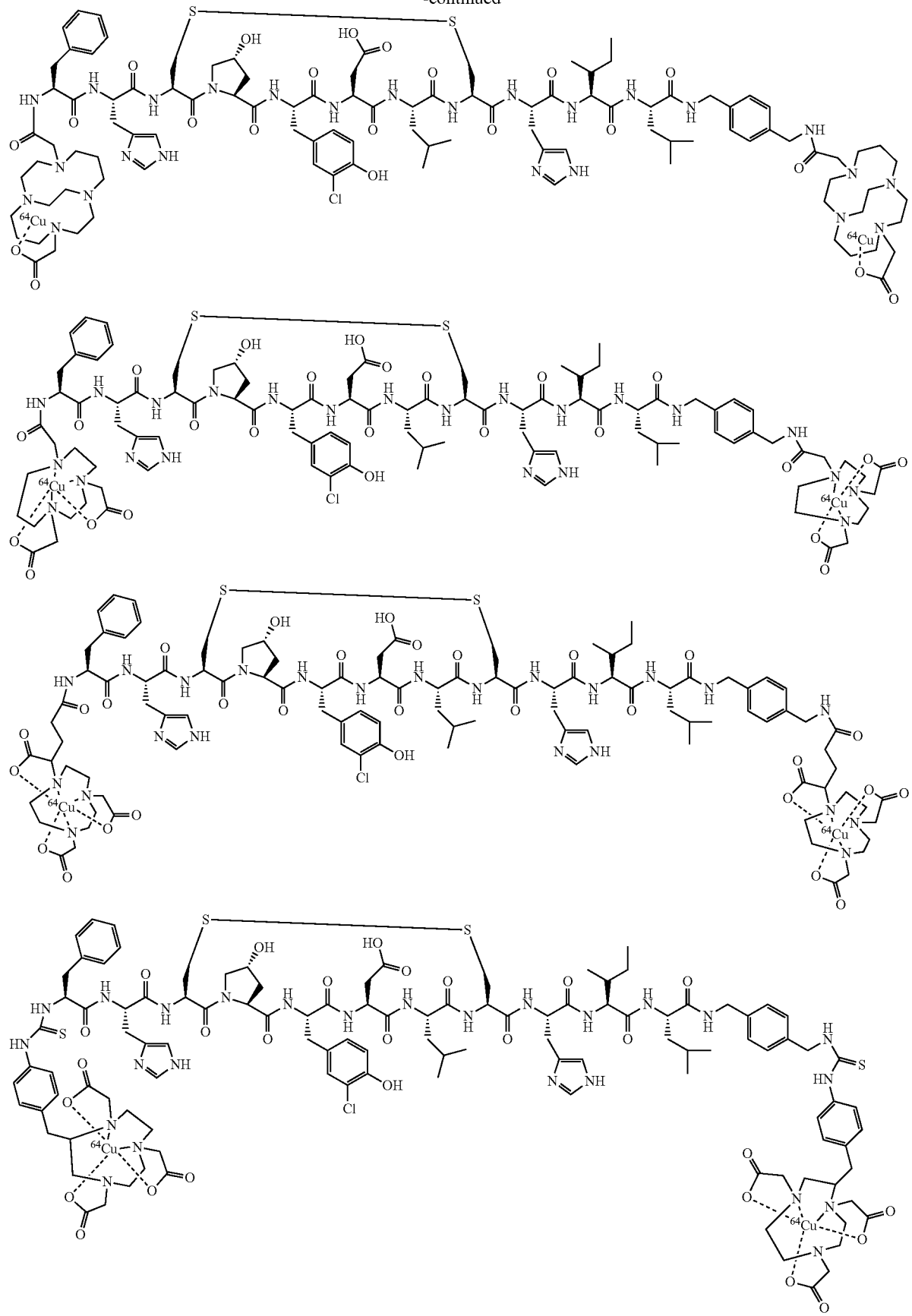

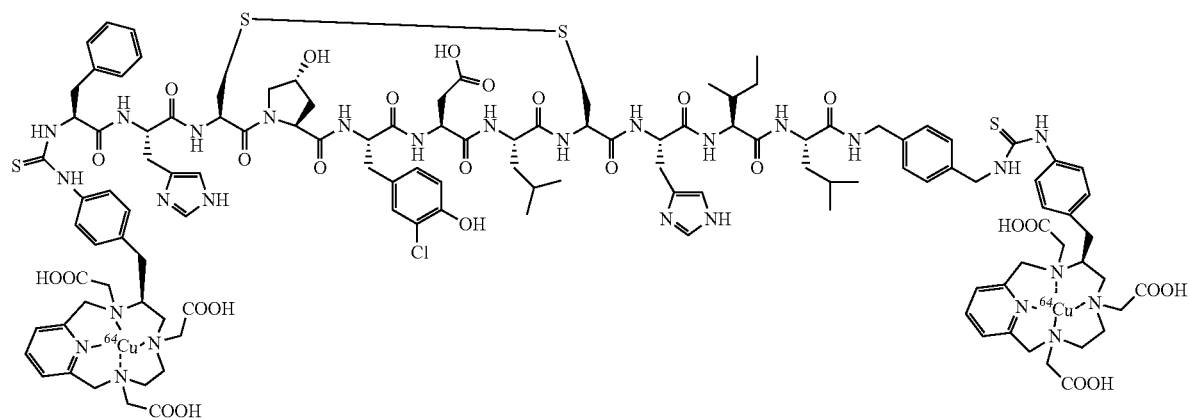
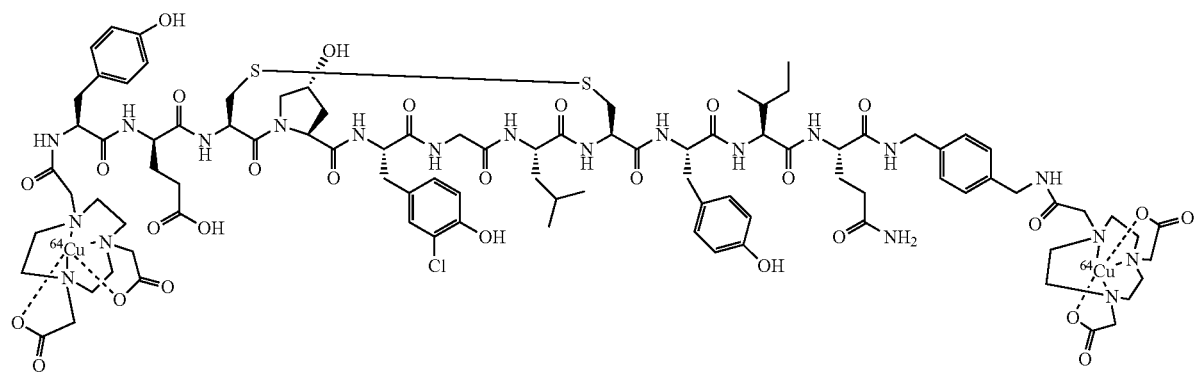
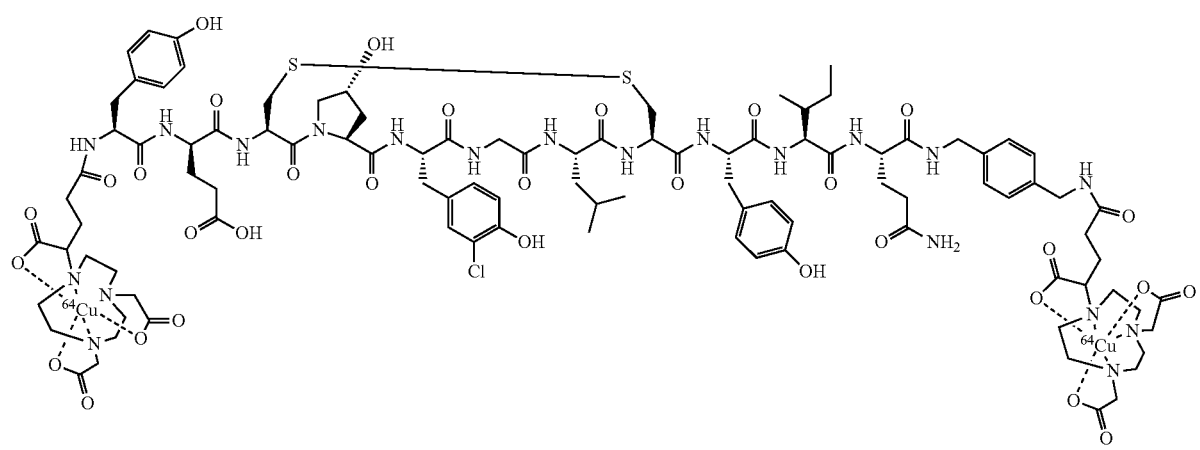

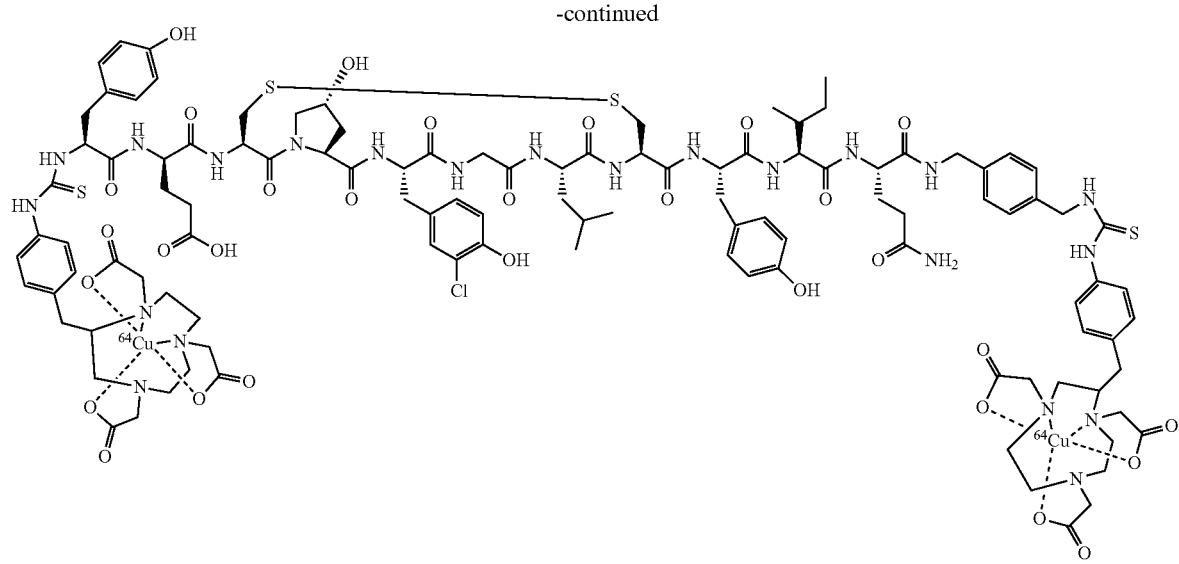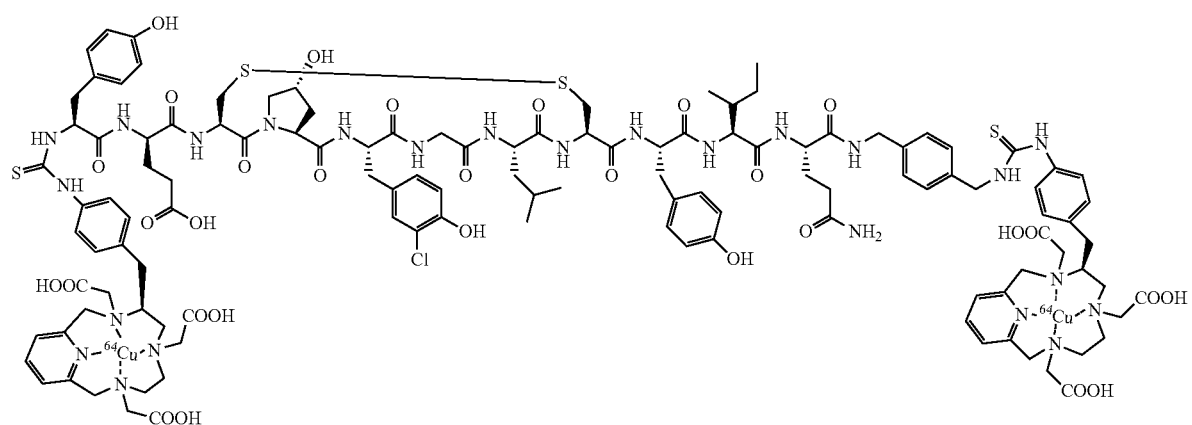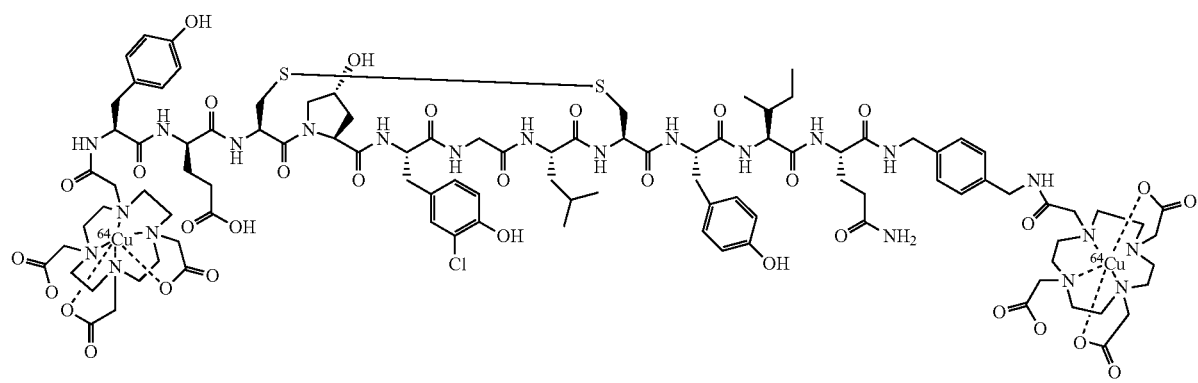

-continued
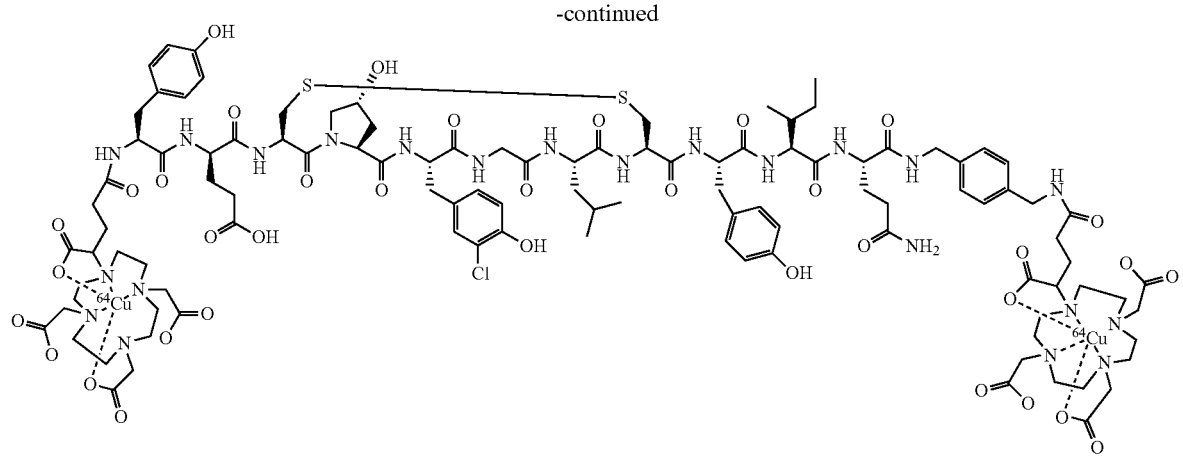
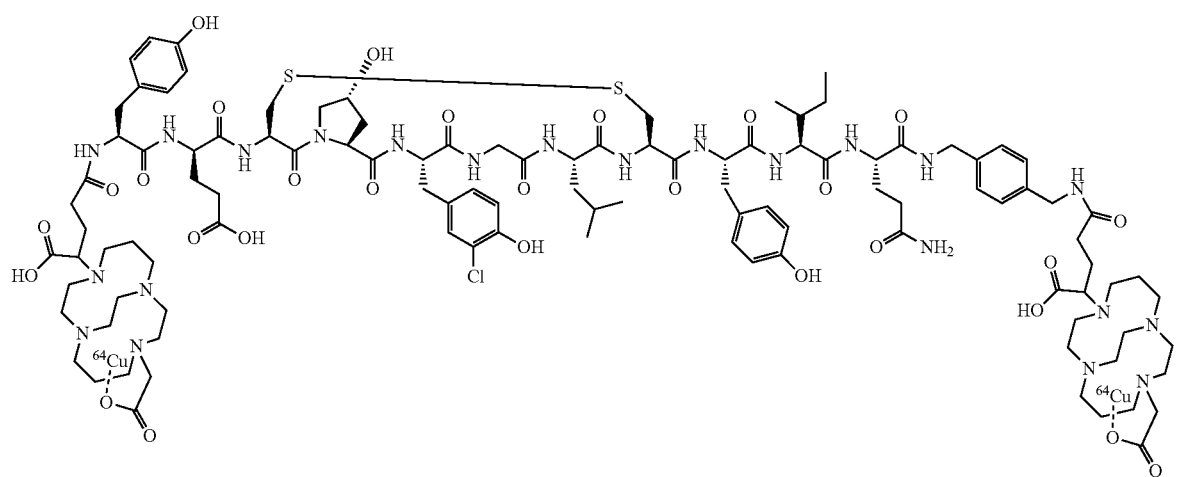
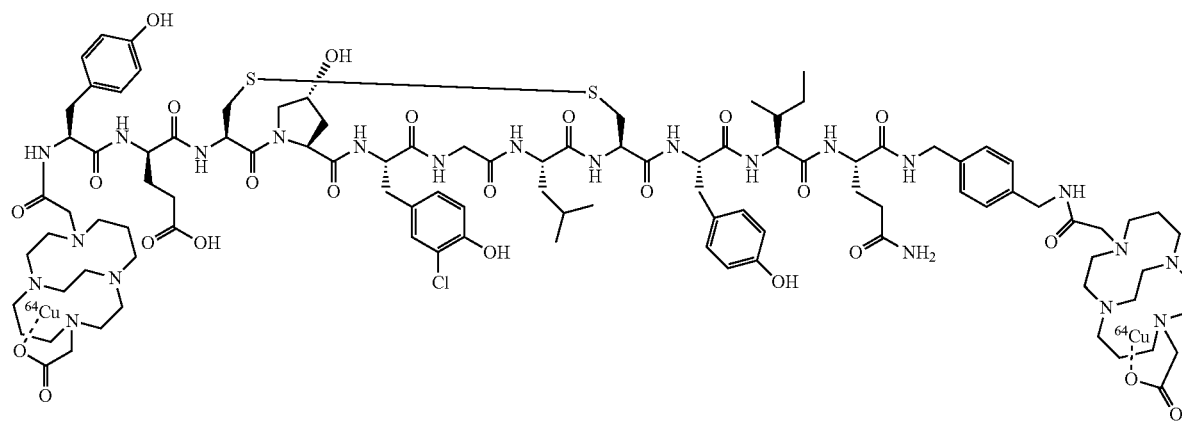
or a pharmaceutically acceptable salt form thereof.

In some embodiments, a fibrin-specific imaging agent can have the structure:

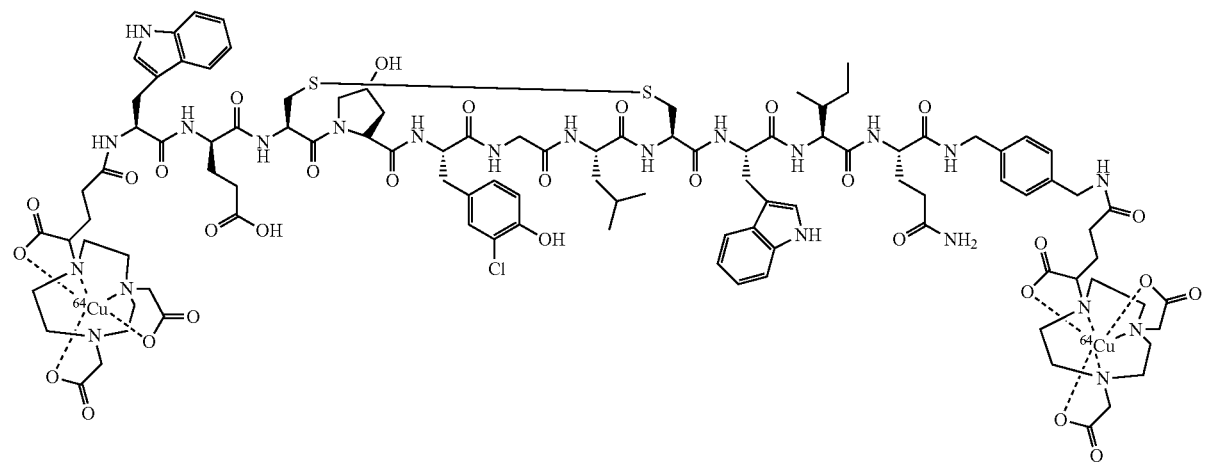

In some embodiments, a fibrin-specific imaging agent can have the formula:

IR$_1$-L$_1$-FTP-L$_2$-IR$_2$ wherein:
FTP is a fibrin binding peptide;
L$_1$ and L$_2$ are optional linkers;
IR$_1$ and IR$_2$ are imaging reporters wherein the two imaging reporters are selected from the pairs consisting of: a fluorescent dye and a chelator comprising a radioactive metal ion; a fluorescent dye and a chelator comprising a paramagnetic metal ion; and a chelator comprising a radioactive metal ion and a chelator comprising a paramagnetic metal ion.

The imaging agent can be a compound of the formula:

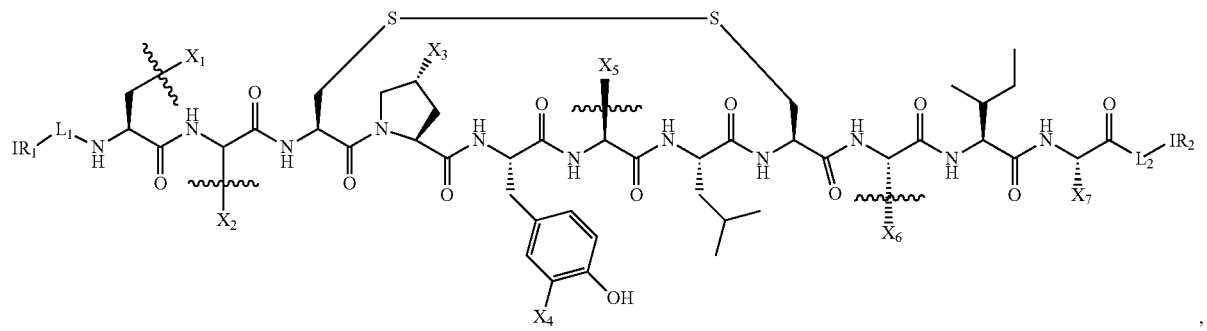

wherein:

X$_1$ is selected from the group consisting of:

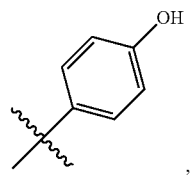 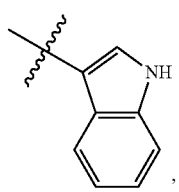 and

X$_2$ is selected from the group consisting of:

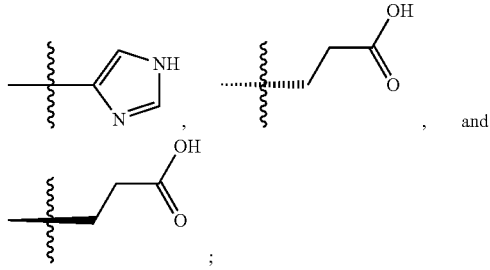

-continued

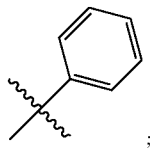

$X_3$ is selected from the group consisting of H and OH;

$X_4$ is selected from the group consisting of H, I, Br, and Cl;

$X_5$ is selected from the group consisting of H and $CH_2COOH$;

$X_6$ is selected from the group consisting of:

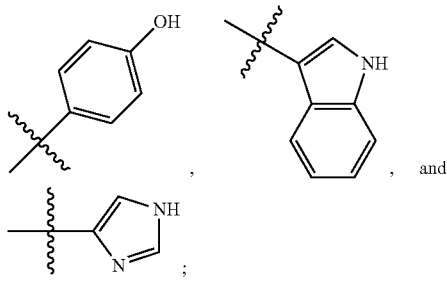

, and $X_7$ is selected from the group consisting of $CH_2CH_2C(O)NH_2$ and $CH_2CH(CH_3)_2$.

When $L_1$ is present, it can be selected from the group consisting of:

—NHCH(R)C(O)—, wherein R is any natural amino acid side chain;

—NH$(CH_2)_n$C(O)—, wherein n is an integer from 1-6;

—$NHCH_2CH_2OCH_2CH_2C(O)$—; and

—$NHCH_2CH_2OCH_2CH_2OCH_2CH_2C(O)$—.

$L_2$, when present, can be selected from the group consisting of:

—$NHCH_2C_6H_4CH_2NH$—;

—NH$(CH_2)_m$NH—, wherein m is an integer from 2-6;

—$NHCH_2OCH_2NH$—;

—$NHCH_2CH_2OCH_2CH_2NH$—; and

—$NHCH_2CH_2OCH_2CH_2OCH_2CH_2NH$—.

In some embodiments, at least one of $IR_1$ and $IR_2$ is a chelator comprising $^{64}Cu$.

Examples of an imaging agent comprising a compound of the formula described above include:

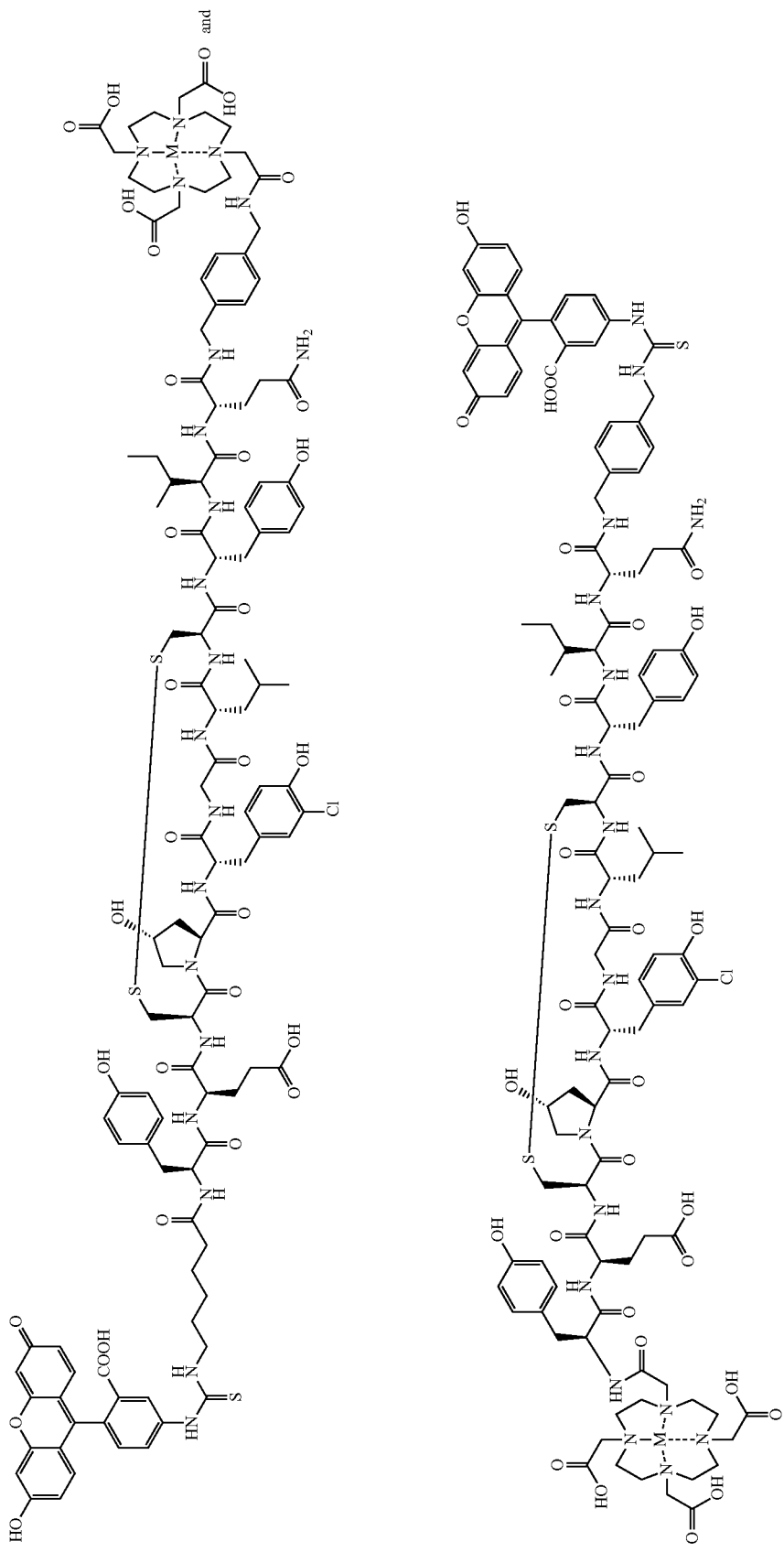

wherein M is a radioactive or paramagnetic metal ion.

Also provided herein is a fibrin-specific imaging agent having the structure:

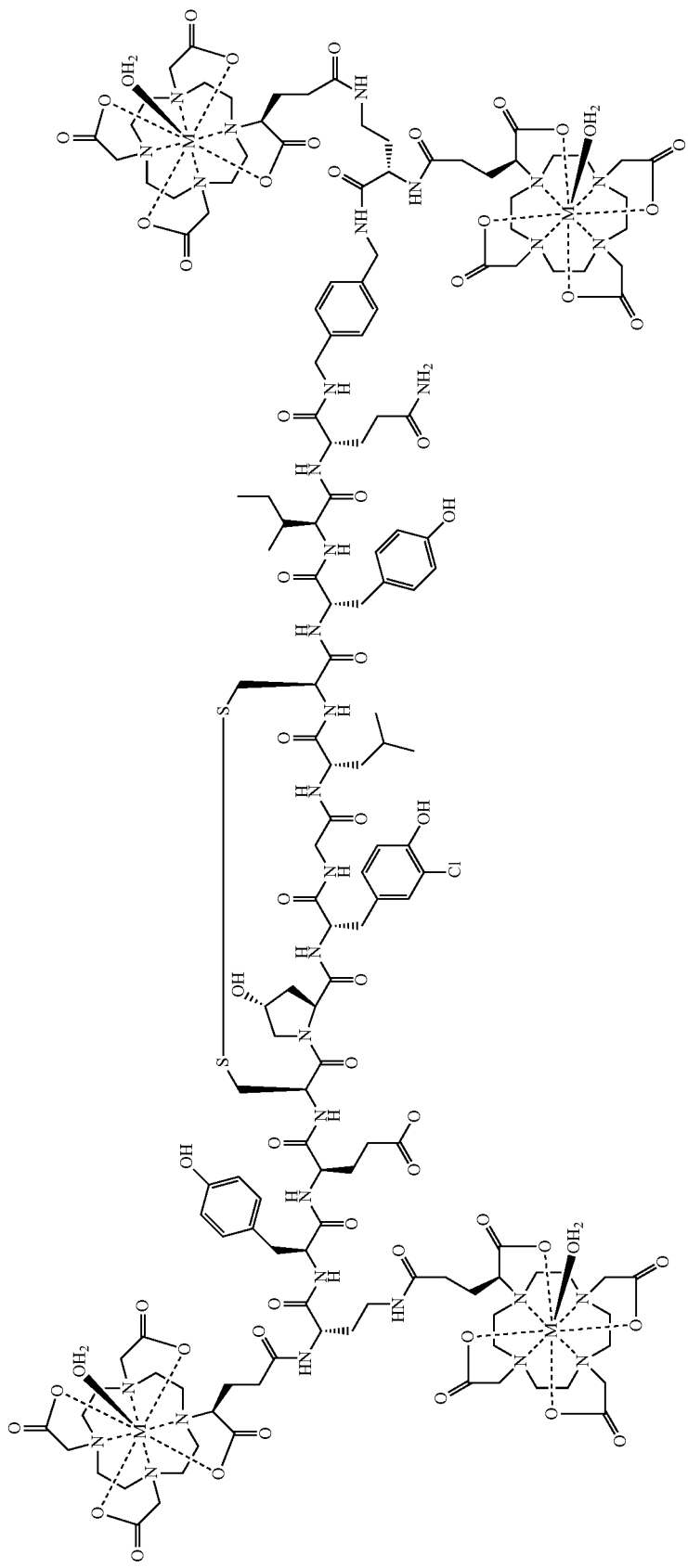

or a pharmaceutically acceptable salt form thereof, wherein each M is independently a radioactive metal ion or $Gd^{3+}$, provided that no more than three M are $Gd^{3+}$. In some embodiments, at least one M is selected from the group consisting of: $^{64}Cu$, $^{67}Cu$, $^{67}Ga$, $^{68}Ga$, $^{86}y$, $^{89}Zr$, $^{99m}Tc$, and $^{111}In$. In some embodiments, three M are $Gd^{3+}$ and one M is a radioactive metal ion. In another embodiment, two M are $Gd^{3+}$ and the remaining two Ms are independently a radioactive metal ion. In a further embodiment, one M is $Gd^{3+}$ and the remaining three Ms are independently a radioactive metal ion. In some embodiments, where multiple Ms are a radioactive metal ion, the Ms can be the same. In some embodiments, the imaging agent may require one or more countercations (e.g., sodium, potassium, ammonium).

The fibrin-specific imaging agents described herein can be prepared using conventional synthetic methods known to those of skill in the art. See, for example, U.S. Pat. Nos. 6,984,373; 6,991,775; and 7,238,341 and U.S. Patent Application No. 2005/0261472, as well as the Examples detailed below. The specific parameters included in the examples are intended to illustrate and are not presented to in any way limit the disclosure.

Imaging agents employing metallo-radionuclides are often prepared by chelating the radionuclide in the final synthetic step. It is useful to avoid HPLC purification of the final product as this purification step is time consuming, involves organic solvents which must be removed from the purified product prior to use, and generally results in lower yields because of radioactive decay during the purification process. The fibrin-specific imaging agents described herein incorporate potent chelators to quantitatively bind the radionuclide often avoiding the need for any additional purification. If there is any radionuclide present that is not the final product, then this can be easily removed in two ways based on ion exchange chromatography. The metallo-radionuclide precursors are typically cationic species, e.g. $^{64}Cu^{2+}$, $^{68}Ga^{3+}$. If analytical radio-HPLC or radio-TLC indicate that the impurity is unreacted metallo-radionuclide, then the reaction mixture can be passed through a cationic exchange column, e.g. Dowex-50 resin, sodium form. The unreacted cationic radionuclide will adhere to the column while the desired negatively charged or neutral imaging agent will pass through the column unchanged. This is a fast purification that uses no organic solvent and results in pure product. An alternate method is to add cation exchange resin, e.g. Dowex-50 resin, sodium form, directly to the solution to bind the cationic radionuclide impurity. The solution is then filtered to remove the resin containing the impurity.

It is also possible that other impurities may be formed. For instance it is possible for the metallo-radionuclide to bind weakly to amino acid side chains of the peptide and not be bound by the chelator. This may be encountered when preparing imaging agents of very high specific activity. In those instances, a positively charged weak chelator can be added in excess to scavenge radionuclide weakly associated with the peptide. For instance diethylenetriamine (dien) exists in solution at pH 7 as a di-cation, $H_2dien^{2+}$. Diethylenetriamine forms stable complexes with the $Cu^{2+}$ ion resulting in a positively charged complex, $Cu(dien)^{2+}$. However dien is not capable of displacing $Cu^{2+}$ from the more stable chelators used in this application, e.g. DOTA, NOTA, CB-TE2A, etc. After incubating the reaction mixture briefly with diethylenetriamine, the resultant solution is passed through a cation exchange column or cartridge, e.g. Dowex-50 resin, sodium form. The cation exchange column removes the positively charged $H_2dien^{2+}$ and $Cu(dien)^{2+}$ but the desired negatively charged or neutral imaging agent will pass through the column unchanged. Alternately, the cation exchange resin can be directly added to the solution, and then filtered to remove the resin containing the impurity. Again, these purification methods are fast and avoid the use of organic solvents.

One skilled in the art can appreciate that other weak chelating ligands that form cationic complexes with the specific radionuclide used could be employed. For instance, the reference Critical Stability Constants, vols. 1-6 edited by A. E. Martell and R. M. Smith, Plenum Press, 1989 could be consulted to find appropriate ligands for an appropriate metal ion. Similarly, other cation exchange resins could be used.

Methods of Use

The fibrin-specific imaging agents described herein can be used to image fibrin present in a mammal. For example, the imaging agents can be used to image thrombi, solid tumors, and atherosclerotic plaques. Any suitable method of imaging fibrin, as appropriate for the imaging reporters present on the imaging agent, may be used.

For example, provided herein is a method of imaging fibrin in a mammal. In some cases, the method can include:
 a) administering to the mammal an imaging agent as described herein, wherein the imaging agent comprises at least one imaging reporter comprising a chelator and a radioactive metal ion;
 b) acquiring an image of the mammal using a nuclear imaging technique;
 c) acquiring an image of the mammal using magnetic resonance imaging or computed tomography; and
 d) overlaying the images of steps b) and c) to image the fibrin within the mammal.

A nuclear imaging technique, as described herein, can include SPECT and PET. Without being bound by theory, the nuclear imaging technique can be used to detect and image the imaging agent directly. The second image can then be used to acquire a high resolution anatomical map using, for example, magnetic resonance imaging (MRI) or computed tomography (CT). The images are then overlaid or fused to localize the low resolution fibrin-targeted image within the high resolution anatomical image. For example, to identify the presence of thrombus in a specific blood vessel, a CT angiogram can then be obtained and this image fused with the nuclear medicine image. The CT image would show the vascular tree and the PET or SPECT image would identify the thrombus in a specific artery or vein. The order of acquiring the images is unimportant: the MR or CT image can be acquired prior to, after or simultaneous with the nuclear image.

Overlaying of images can be done by various means known in the art. See, for example, U.S. Pat. Nos. 7,412,279; 7,110,616; 6,898,331; 6,549,798; and 5,672,877; Rudd, J. H F. et al., *J. Nucl. Med.* 2008 49(6): 871-878; Slomka, P. J. et al., *J. Nucl. Med.* 2009 50: 1621-1630; and Jupp, B. and O'Brien, T. J., *Epilepsia* 2007 49: 82-89. In some embodiments, the first and second image data sets can be overlaid to determine the presence of the fibrin within the mammal, provided that the image acquired using nuclear imaging indicated the presence of fibrin. For example, the first and second image data sets can be combined to produce a third data set that includes an image of the fibrin target and an image of anatomical region where the fibrin is located. The third data set is capable of indicating the location of the fibrin, if present, within the mammal. If desired, the third data set may be displayed on a display device in order to indicate the location of the stationary target within the vascular system. The third data set may also indicate the size of the stationary target within the mammal.

In some embodiments, the MR or CT imaging can employ a contrast agent, wherein the contrast agent is non-specific for fibrin or thrombi. Such a contrast agent can be any known to those of skill in the art. For example, Gd(HP-DO3A), Gd(DTPA), Gd(BOPTA), Gd(EOB-DTPA), Gd(DOTA), Gd(DTPA-BMA), gadoversetamide, gadofosveset for use with MRI or iopamidol, iohexol, ioxilan, iopromide, iodixanol, ioxaglate, metrizoate, or diatrizoate for use with CT.

Further provided herein is a method of imaging fibrin using an imaging agent having at least two imaging reporters, wherein the at least two imaging reporters are selected from the pairs consisting of: a fluorescent dye and a chelator comprising a radioactive metal ion; a fluorescent dye and a chelator comprising a paramagnetic metal ion; and a chelator comprising a radioactive metal ion and a chelator comprising a paramagnetic metal ion. The method includes:
  a) administering to a mammal the imaging agent described above; and
  b) acquiring a first and second image of the mammal using two imaging methods selected from 1) nuclear imaging technique, 2) magnetic resonance imaging, 3) computed tomography, and 4) optical imaging, wherein the selected imaging methods are appropriate for the imaging reporters present in the imaging agent of step a).

Optical imaging, as described herein, can include near infrared (NIR) imaging. The two images may be acquired sequentially or simultaneously. In some cases it may be beneficial to acquire an image with the lower resolution modality first and then use this image to direct where the second higher resolution image is acquired. For example, a non-invasive image can be obtained using a nuclear imaging technique like PET or SPECT (if radiolabeled) or MRI (if labeled with gadolinium) that is sensitive to the imaging agent. This first, non-invasive image is used to identify the region for invasive NIR imaging. A NIR image can then be obtained, e.g. using a fiber optic catheter, and a thrombus on the coronary vessel wall can be imaged for the purpose of guiding surgical therapy. Alternately a NIR image may be obtained in the surgical field to guide the surgeon to the margins of a tumor.

The imaging agents and methods described herein can be used in numerous diagnostic and therapeutic applications. For example, imaging thrombi in a mammal, detecting the presence or absence of thrombi in a mammal, imaging a solid tumor in a mammal detecting the presence or absence of a solid tumor in a mammal, imaging an atherosclerotic plaque in a mammal, detecting the presence or absence of an atherosclerotic plaque in a mammal.

Pharmaceutical Compositions and Salts

Pharmaceutical compositions as described herein comprise at least one fibrin-specific imaging agent, or pharmaceutically acceptable salts thereof, and one or more pharmaceutically acceptable ingredients, excipients, carriers, adjuvants and/or vehicles.

Pharmaceutical compositions can be administered to mammals including humans in a manner similar to other diagnostic or therapeutic agents. The dosage to be administered and the mode of administration will depend on a variety of factors including age, weight, sex, condition of the patient, and genetic factors, and will ultimately be decided by the attending physician or veterinarian. In general, dosage required for diagnostic sensitivity or therapeutic efficacy will range from about 0.001 to 50,000 g/kg, more usually 0.01 to 25.0 g/kg of host body mass.

Pharmaceutically acceptable carriers, adjuvants and vehicles that may be used in the pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions may be administered by a variety of routes or modes. These include, but not limited, to oral, intratracheal, sublingual, pulmonary, topical, rectal, nasal, buccal, vaginal, parenteral, or via an implanted reservoir. Implanted reservoirs may function by mechanical, osmotic, or other means. The term parenteral as used herein includes intraperitoneal, paravertebral, periarticular, periostal, subcutaneous, intracutaneous, intravenous, intra-arterial, intramuscular, intra-articular, intrasynovial, intrasternal, intrathecal, intralesional and intracranial injection or infusion techniques.

Such compositions are preferably formulated for parenteral administration, and most preferably for intravenous or intra-arterial administration. Generally, and particularly when administration is intravenous or intra-arterial, pharmaceutical compositions may be given as a bolus, as two or more doses separated in time, or as a constant or nonlinear flow infusion.

Details concerning dosages, dosage forms, modes of administration, composition and the like are further discussed in a standard pharmaceutical text, such as Remington's Pharmaceutical Sciences, 18th ed., Alfonso R. Gennaro, ed. (Mack Publishing Co., Easton, Pa. 1990), which is hereby incorporated by reference.

The imaging agents described herein can also be in the form of a pharmaceutically acceptable salt. The term "pharmaceutically acceptable salt," as used herein, refers to derivatives of the imaging agents wherein the parent compound is modified by making the acid or basic groups not yet internally neutralized in the form of non-toxic, stable salts which does not destroy the pharmacological activity of the parent compound.

Suitable examples of the salts include: mineral or organic acid salts, of basic residues such as amines; alkali or organic salts of acidic residues such as carboxylic acids; and the like.

Preferred cations of inorganic bases which can be suitably used to prepare salts comprise ions of alkali or alkaline-earth metals such as potassium, sodium, calcium or magnesium. Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the imaging agents include the ions of halo acids such as chlorides, bromides, iodides or other ions such as sulfate. Preferred anions of organic acids comprise those of the acids routinely used in pharmaceutical techniques for the salification of basic substances such as, for instance, acetate, succinate, citrate, fumarate, maleate or oxalate.

Preferred cations and anions of amino acids comprise, for example, those of taurine, glycine, lysine, arginine, ornithine or of aspartic and glutamic acids.

Pharmaceutical compositions can also include stabilizers and/or stabilizer combinations that slow or prevent radiolytic damage to imaging agents. Any stabilizer known to inhibit radiolytic damage to radiolabeled compounds may be used alone or in combination with other stabilizers. For example, human serum albumin (HSA), ascorbate, phenol, sulfites, glutathione, cysteine, gentisic acid, nicotinic acid, ascorbyl palmitate, $PO_2H_3$, glycerol, sodium formaldehyde sulfoxylate, $Na_2S_2O_5$, $Na_2S_2O_3$, $SO_2$, and mixtures thereof. See also, U.S. Patent Application No. 2007/0269375 and WO 1995/025119.

Kits

Also provided herein are kits. Typically, a kit includes one or more fibrin-specific imaging agents as described herein. In certain embodiments, a kit can include one or more delivery systems for the imaging agent, and directions for use of the kit (e.g., instructions for treating a subject).

In some embodiments, a kit can include one or more imaging agent precursors, wherein the imaging agent has not been chelated to a paramagnetic or radioactive metal ion (e.g., $^{64}Cu$). Such precursors may be present in the form of a lyophilized powder or as a sterile solution. In such cases, the kit can further include a labile form of the metal ion (e.g., an acetate or halide salt) and/or directions for use of the kit (e.g., instructions for the final chelation of the metal ion to the imaging agent prior to administration to a mammal).

Unless defined otherwise, all technical and scientific terms used herein have the same meaning as is commonly understood by one of ordinary skill in the art to which this disclosure pertains. All patents, applications, published applications, and other publications are incorporated by reference in their entirety. In the event that there is a plurality of definitions for a term herein, those in this section prevail unless stated otherwise.

EXAMPLES

Example 1

Cu-64 Bifunctional Chelator

Eisenwiener (Eisenwiener K P, Prata M I, Buschmann I, et al. *Bioconjug Chem.* 2002 13(3):530-41) described the synthesis of racemic NODAGA starting from protected α-bromoglutaric acid. The optically pure isomer is preferred since this will result in a single isomer when coupled to a peptide, rather than diasteromers if the racemate is used. The mesylate of the differentially protected, enantiomerically pure S-2-hydroxy-1,5-pentanedioic acid derivative has been described (U.S. Application No. 2007/0244316). Reacting this with 2 equivalents of commercial triazacyclononane (TACN) gives the monosubstituted product. Excess TACN is removed by washing with water. Alkylation of the remaining nitrogens with tert-butyl protected bromoacetic acid gives the protected R-NODAGA intermediate. Removal of the benzyl group by hydrogenation gives the advanced bifunctional intermediate product shown following step (iii) in Scheme 1. This molecule can then be coupled to amino groups on peptides via the free acid. Acid deprotection of the tert-butyl groups followed by chelation with copper gives the desired product.

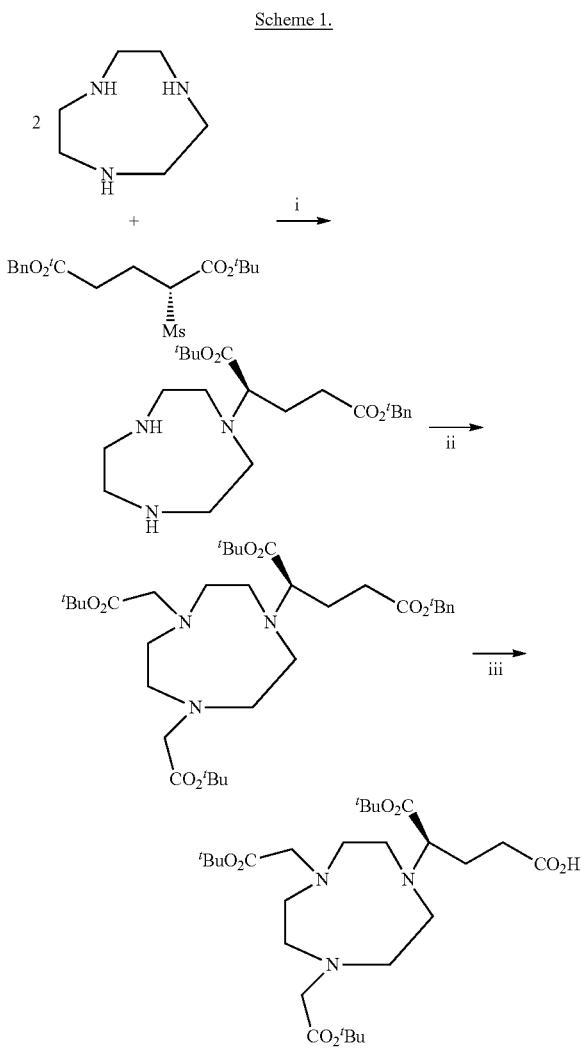

Scheme 1.

i. $K_2CO_3$, 50° C.
ii. $BrCH_2COO^tBu$, $K_2CO_3$, 50° C.
iii. $H_2/Pd-C/MeOH$ Example 2

Fibrin-Specific PET Probes

A fibrin-specific PET probe is described in Scheme 2 and prepared as follows. First p-xylenediamine is coupled to 2-chlorotritylchloride resin in DMF using diisopropylethylamine (DIPEA) as a base as described previously (Overoye-Chan K, Koerner S, Looby R J, et al. *J Am Chem Soc.* 2008 130(18):6025-39). Standard solid phase peptide coupling is then used to elongate the peptide. The peptide used in this example is the same as used in EP-2104R (Overoye-Chan K, Koerner S, Looby R J, et al. J Am Chem Soc. 2008 130(18):6025-39). The completed peptide is then cleaved from the resin and deprotected using trifluoroacetic acid. The peptide is precipitated by addition of cold diethyl ether. This linear peptide is then taken up in a 1:1 mixture of DMSO and pH 4.5 sodium acetate buffer and allowed to cyclize overnight via DMSO oxidation. At this stage the resultant peptide diamine may be purified by HPLC. This peptide is then reacted with two equivalents of NODAGA t-butyl ester (see Example 1) using standard coupling conditions of HOBT and PyBOP in DMF. The tert-butyl groups are then removed using TFA and the product precipitated with cold ether. This precursor is then taken up in sodium acetate buffer, pH 5.5, and reacted with 20 mCi of $^{64}$CuCl$_2$ for 60 minutes at 60° C. The solution is then passed through a cation exchange cartridge (Na$^+$ form) and then through a 0.2 µm filter into a sterile vial.

a TFA (88 parts), triisopropyl silane (4), thioanisole (4), water (4) cocktail. Precipitation with cold ether gives the deprotected peptide with a primary amine at the C-terminus (Scheme 3). The peptide is cyclized using DMSO as described in the Example 2. The near infrared dye AlexaFluor 750 purchased as the succinimidyl ester is conjugated to the C-terminus in solution. HPLC purification gives the probe precursor denoted Cu-Pep-Fluor. This precursor is

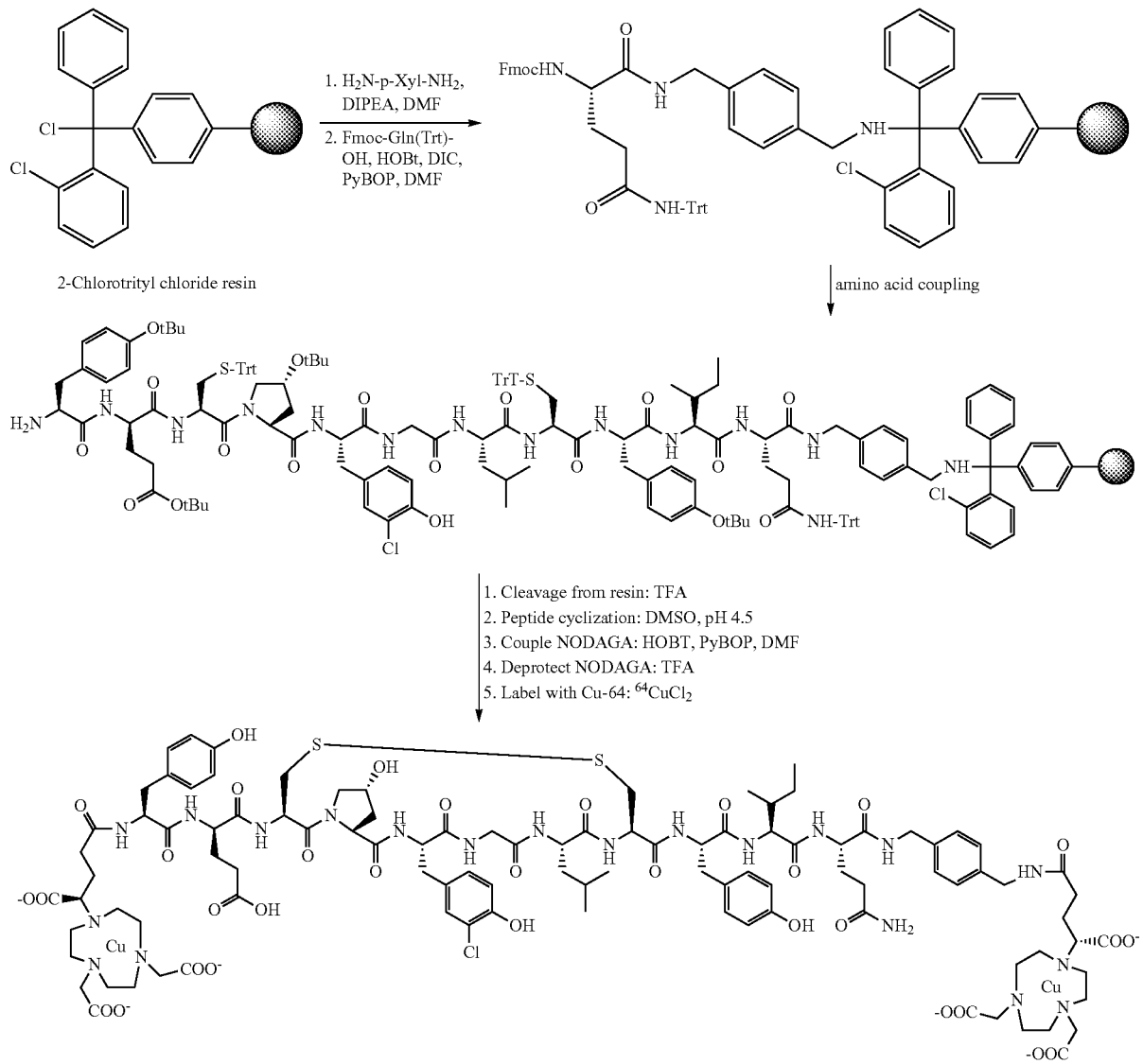

Example 3

Synthesis Dual PET-NIR Fibrin-Specific Probes

Starting from the protected peptide still on resin as described in Example 2, the NODAGA t-butyl ester from Example 1 is converted to the pentafluorophenol ester (PFP) (Overoye-Chan K, Koerner S, Looby R J, et al. J Am Chem Soc. 2008 130(18):6025-39) and coupled to the N-terminus. After coupling the chelator to the resin, the peptide is cleaved from the resin and deprotected in a single step using then taken up in sodium acetate buffer, pH 5.5, and reacted with 20 mCi of $^{64}$CuCl$_2$ for 60 minutes at 60° C. The solution is then passed through a cation exchange cartridge (Na$^+$ form) and then through a 0.2 µm filter into a sterile vial.

Alternatively, the dye is conjugated to the N-terminus while the peptide is still on resin. The dye conjugated peptide is cleaved from the resin and deprotected with TFA, precipitated with ether and then cyclized with DMSO. One equivalent of NODAGA-PFP is then coupled to the C-terminal amino group in solution. The t-Bu protecting groups on the NODAGA ligand are removed by treatment with TFA. HPLC purification gives the probe precursors denoted Fluor-Pep-Cu. This precursor is then taken up in sodium acetate buffer, pH 5.5, and reacted with 20 mCi of $^{64}CuCl_2$ for 60 minutes at 60° C. The solution is then passed through a cation exchange cartridge (Na$^+$ form) and then through a 0.2 μm filter into a sterile vial.

DOTAGA-PFP synthons (Overoye-Chan K, Koerner S, Looby R J, et al. J Am Chem Soc. 2008 130(18):6025-39) can be reacted with the peptide on solid phase. The strong acid cleavage cocktail described above results in a deprotected peptide off resin with both DOTAGA ligands deprotected and a free primary amine at the C-terminus. The peptide is cyclized with DMSO and then chelated by adding two equivalents of GdCl$_3$ and stirring at pH 6.5 for 4 hours. The succinimidyl ester of the AlexaFluor dye is then coupled in aqueous solution. HPLC purification gives the Gd$_2$-Pep-Fluor construct.

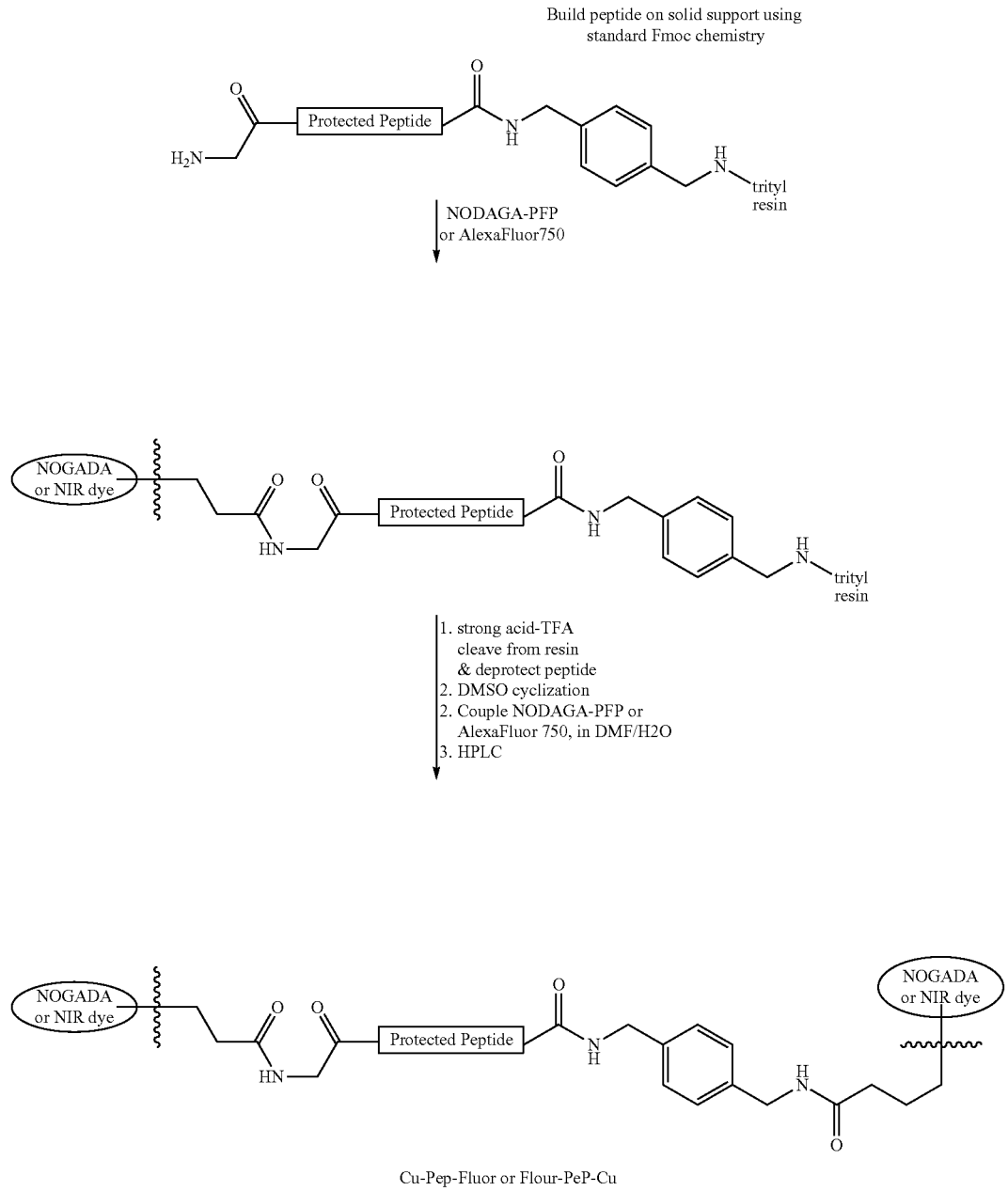

Cu-Pep-Fluor or Flour-PeP-Cu

Example 4

Synthesis of Dual MRI-NIR Probe

The same protected peptide on resin can be used to prepare probes with 2 gadolinium chelates at the N-terminus (for MRI contrast) and a NIR dye at the C-terminus, Scheme 4. Using Fmoc protected lysine at the N-terminus, 2

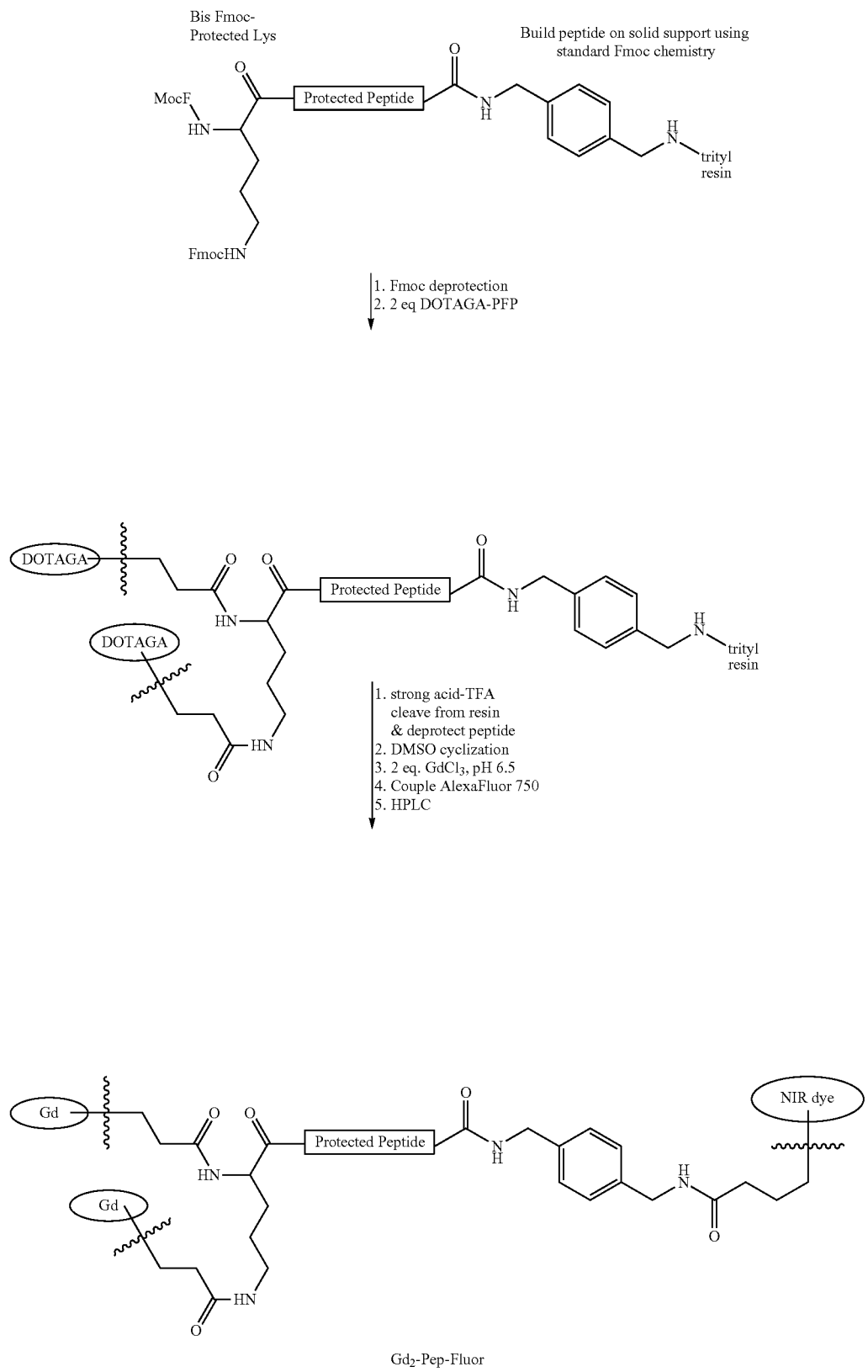

Example 5

Synthesis of a Bis-Cu-64 PET Agent

1) Synthesis of DOTAGA(OtBu)$_4$-OPFP (1)

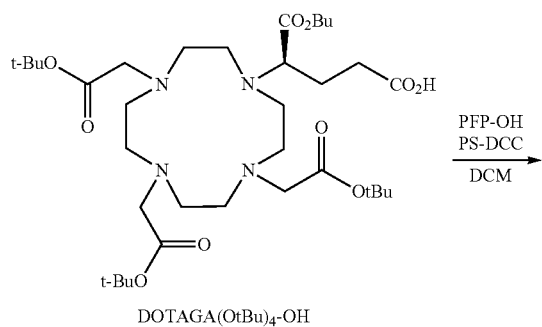

Scheme 5. Synthesis of DOTAGA(OtBu)4-OPFP (1)

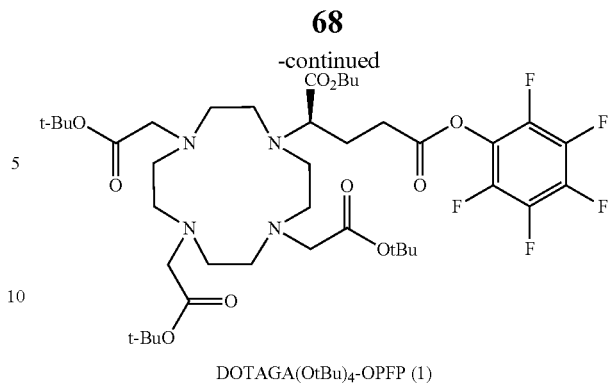

DOTAGA(OtBu)$_4$-OPFP (1)

DOTAGA(OtBu)$_4$-OH (0.4 g, 0.571 mmol, 1 eq) and pentafluorophenol (PFP, 0.1262 g, 0.686 mmol, 0.361 g, 0.686 mmol, 1.2 eq) were dissolved in dichloromethane (DCM). Polystyrene-carbodiimide resin (PS-DCC, 1.2 eq, 1.9 mmol/g loading capacity) was added to the solution and the reaction vessel was shaken on an orbital shaker for 3 h. The reaction was monitored by HPLC. The reaction mixture was filtered and the solvent evaporated. Yield=0.4376 g, includes unreacted PFP which does not interfere with the next step.

2) Synthesis of the Bis(DOTAGA(OtBu)$_4$)-FBP-mXD (3)

Scheme 6. Synthesis of Bis(DOTAGA(OH)4)-FBP-mXD (4)
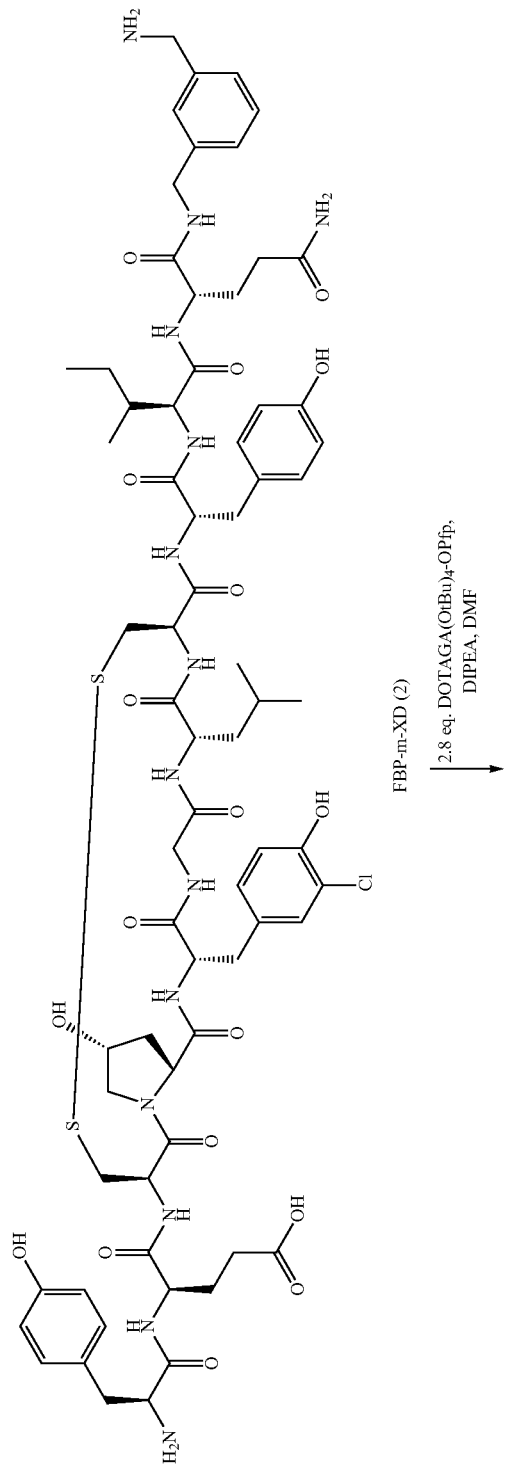
FBP-m-XD (2) $\xrightarrow{\text{2.8 eq. DOTAGA(OtBu)}_4\text{-OPfp,}\atop\text{DIPEA, DMF}}$ -continued
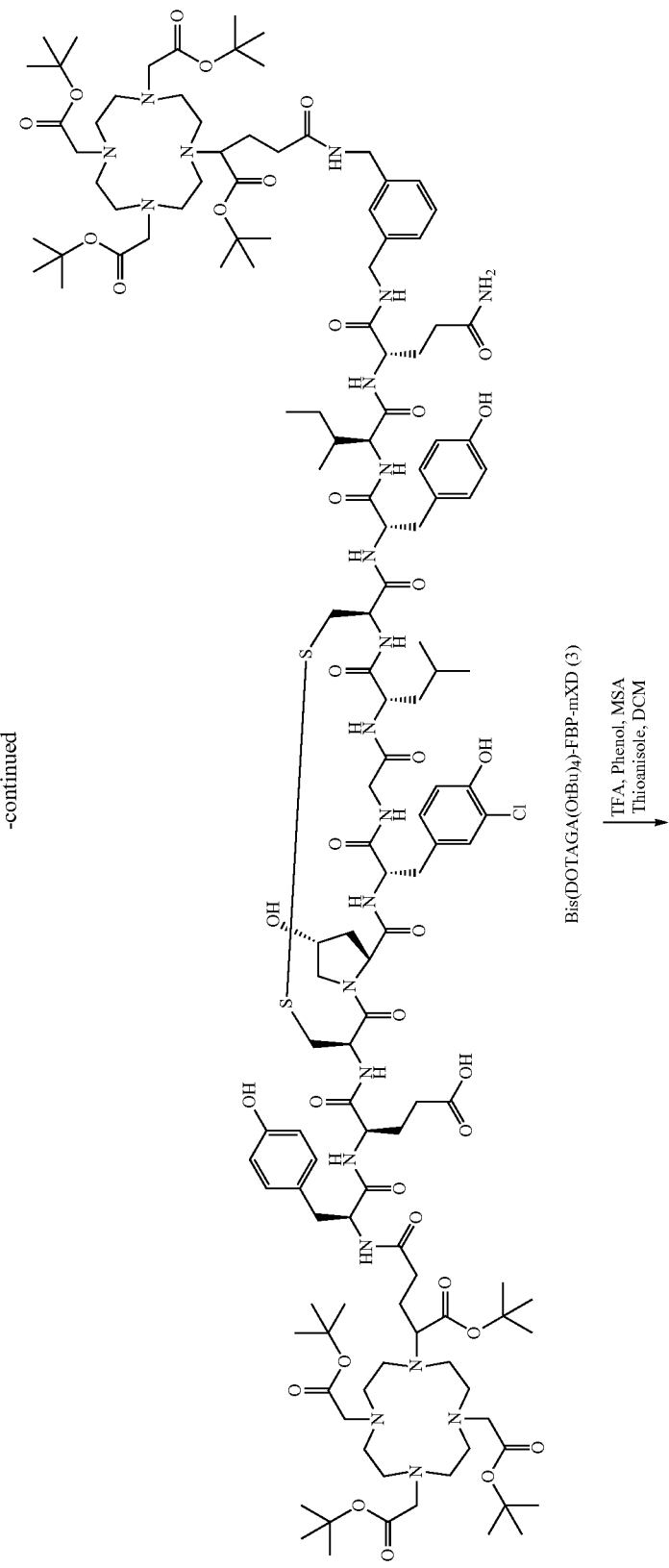
Bis(DOTAGA(OtBu)4)-FBP-mXD (3)
TFA, Phenol, MSA
Thioanisole, DCM

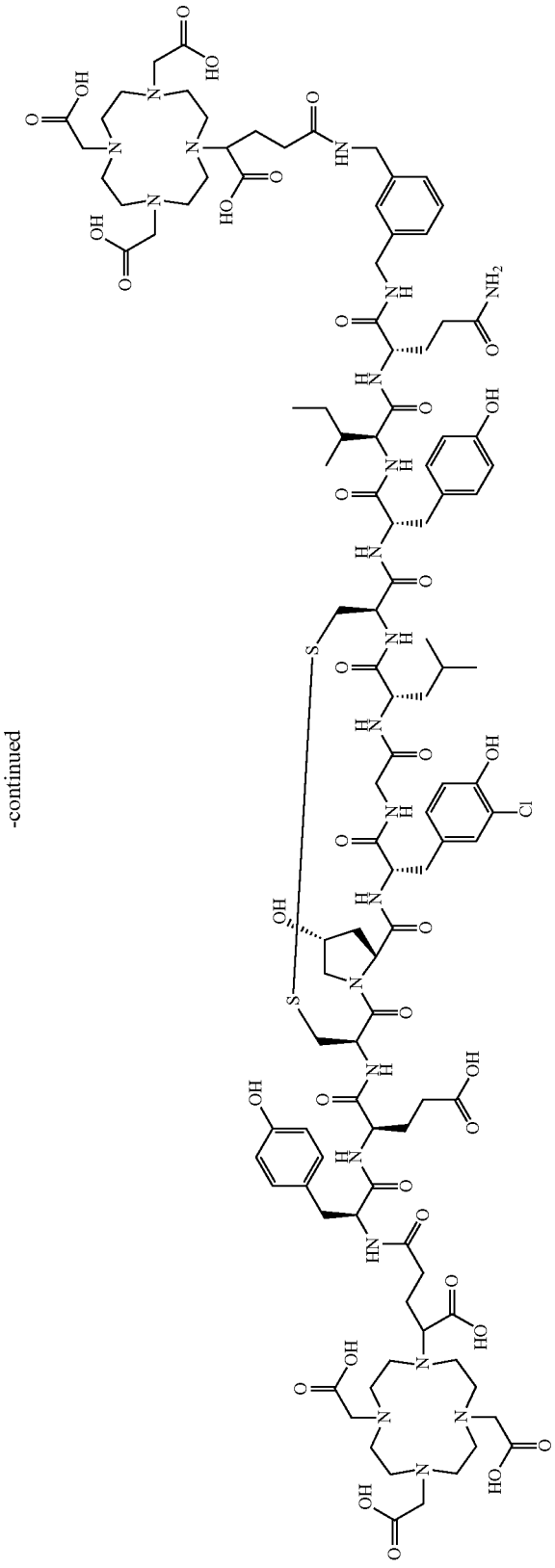
-continued
Bis(DOTAGA(OH)$_4$)-FBP-mXD (4)

The FBP-mXD (2) peptide is prepared as previously described except meta-xylene was used instead of para-xylene (Overoye-Chan K, Koerner S, Looby R J, et al. J Am Chem Soc. 2008 130(18):6025-39). DOTAGA(OtBu)$_4$-OPFP (0.0874 g, 0.1 mmol, 1 eq.) and FBP-m-XD (0.2 g, 0.1 mmol, 1 eq.) were dissolved in 5 m DMF. The pH of the solution was increased to 6.5 with diisopropylethylamine (DIPEA) and it was stirred for 2 h. 0.0438 g (0.5 eq) of 1 was added and the pH was increased to 6.5. Again after stirring for 30 min., another portion of 0.0438 g (0.5 eq) of 1 was added and the pH was increased to 6.5. The same step was repeated after another 30 min. Finally, another 0.0262 g (0.3 eq) of 1 was added and pH maintained at 6.5. The reaction mixture was stirred for another hour and monitored by HPLC. A saturated brine solution was added to the mixture and precipitation was observed. The suspension was stirred for 30 min. The solid was filtered and dried under reduced pressure.

3) Synthesis of the Bis(DOTAGA(OH)$_4$)-FBP-mXD (4)

Bis(DOTAGA(OtBu)$_4$)-FBP-mXD was dissolved in a solution of trifluoroacetic acid (TFA), phenol, methanesulfonic acid (MSA), thioanisole and DCM (90:2.5:2.5:2.5:2.5, ~15 mL/g 3). The reaction was stirred for 20 min. The solution was evaporated to a smaller volume. Diethylether was added to precipitate a solid. The solution was filtered and the solid was washed with ether. The solid was dissolved in a mixture of water and acetonitrile (ACN) and injected onto a prep C4 column. A gradient from 0% B (0.1% TFA/95% H$_2$O/5% ACN) to 100% B (0.1% TFA/10% H$_2$O/90% ACN) was run on the column. Starting from 0% B, the fraction of B increased to 29% over 10 minutes, then from 29 to 31% B over 15 minutes and then from 31 to 100% B over the next 3 min. The column was washed with 100% B for 5 min and the % B was ramped to 0% in the next 2 min. The system was re-equilibrated at 0% B over 5 minutes (total time=35 min). The peptide eluted at a concentration of 30.3% B. (M+2H)$^{2+}$/2: Expected—1217.5, Observed—1217.6: % purity (HPLC, A$_{220}$)=85%.

4) Synthesis of Cu$_2$-bis-(DOTAGA(OH)$_4$)-FBP-mXD (5)

The Cu-64 was received in a small eppendorf tube from Washington University in St. Louis. All the Cu-64 was transferred into a vial using a 0.1 M NaOAc solution, pH 5.5. A 1 mM solution of peptide 4 was prepared in 0.1 M NaOAc, pH 5.5. 50 μL of the peptide 4 solution was added to the Cu-64 solution and stirred at 50° C. for an hour. The solution was checked by RP-TLC. The free Cu-64 in the form of Cu(OAc)$_2$ does not move with the solvent. However, the peptide labeled Cu-64 moves with the mobile phase. If the reaction was not complete and free Cu-64 was observed, more peptide was added to the reaction mixture and the reaction mixture was stirred for another 30 min at 50° C. The solution was checked by RP-TLC and this procedure was repeated until almost no free Cu(OAc)$_2$ was left. The solution was diluted in saline before injection into animals.

Example 6

Synthesis of a Bis-Gd MR Agent, Gd$_2$-Bis-(DOTAGA(OH)$_4$)-FBP-mXD (6)

Compound 4 is dissolved in water and the pH is changed to 6.5 using 1N sodium hydroxide. Gadolinium (III) chloride hexahydrate (GdCl$_3$.6H$_2$O, 1 eq) is added to the solution and the pH is adjusted to 6.5 with 1N sodium hydroxide. The reaction is stirred for 1 h at room temperature and monitored by HPLC. Residual gadolinium (III) chloride is neutralized with ethylenediaminetetraacetic acid (EDTA, 0.25 eq). The reaction is stirred for 15 min. and the pH is adjusted to 6.5 with 1N sodium hydroxide. The neutralization is monitored by testing with xylenol orange. The product is isolated from solution and purified by reverse phase chromatography.

Example 7

Synthesis of Dual MR-Optical Agent, FITC-Hexyl-Cyclic-FBP-p-XD-DOTA-Gd (11)

1) Synthesis of FBP-p-XD-SP (7)

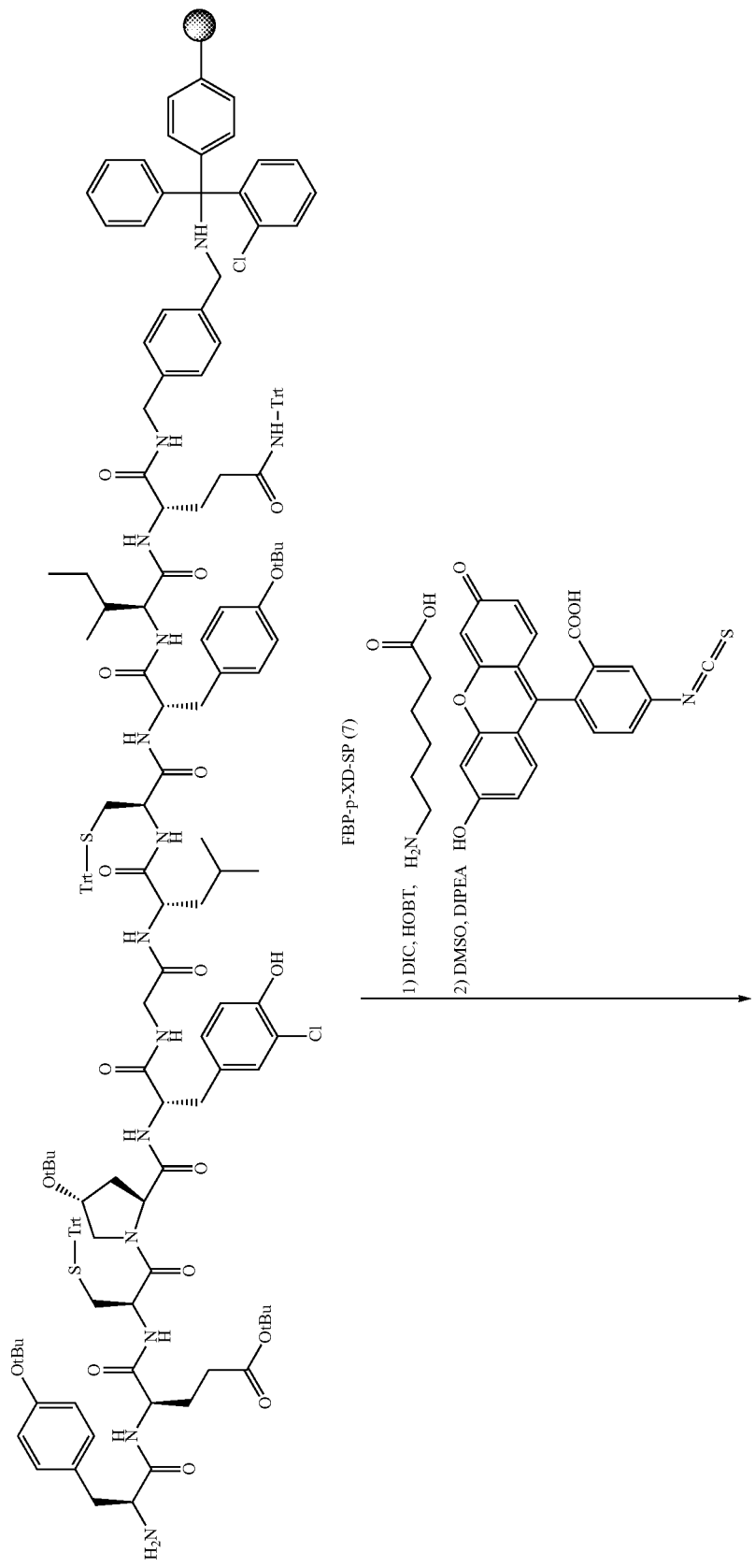
Scheme 7. Synthesis of FITC-hexyl-cyclic-FBP-p-XD-DOTA (10)

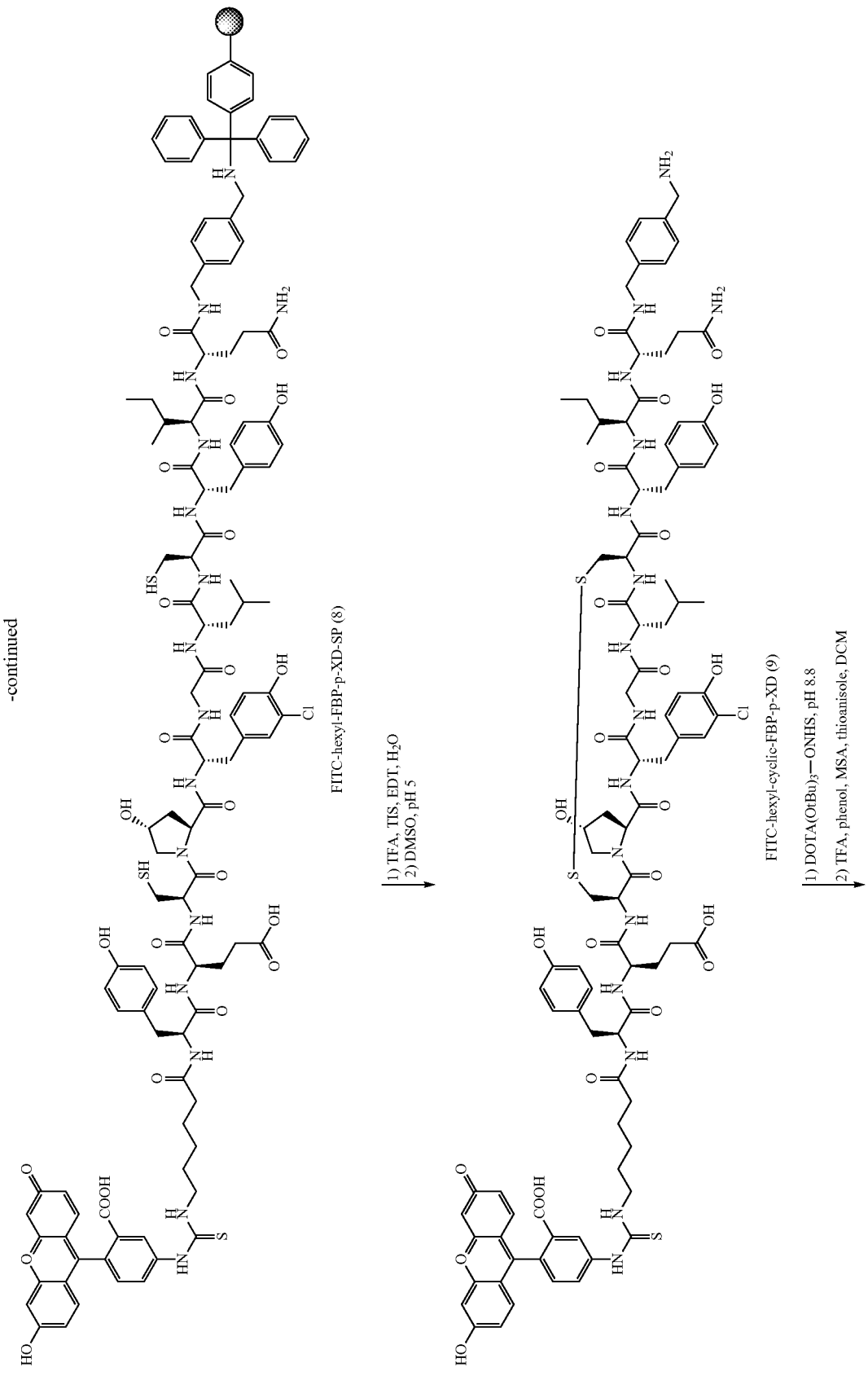

-continued
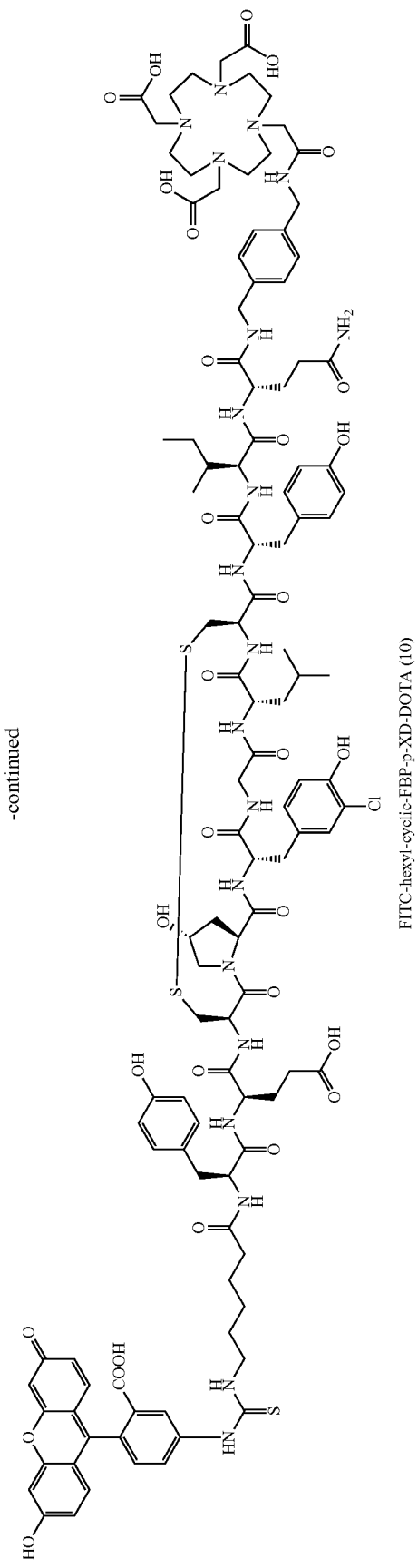
FITC-hexyl-cyclic-FBP-p-XD-DOTA (10)

2-Chlorotritylchloride resin (3.0069 g, 2.947 mmol, 0.98 mmol/g, 1 eq) was swollen in DCM. The resin was then washed with DMF and suspended in DMF. 1.4047 g (10.315 mmol, 3.5 eq) of p-xylylenediamine was added to the suspension. The pH of the mixture was adjusted to 7 with DIPEA. The reaction was agitated for 2 h. A 10 mL solution of DIPEA/DMF/MeOH (17:2:1) was added to the reaction and it was agitated for 30 min. The resin was subsequently washed with DMF. The 1,4-bisaminomethylbenzyl-2-chlorotritylchloride resin was suspended in DMF. Fmoc-Gln(Trt)-OH (6.2991 g, 10.315 mmol, 3.5 eq), diisopropylcarbodiimide (DIC, 2.282 mL, 14.735 mmol, 5.0 eq), and 1-hydroxybenzotriazole (HOBT, 0.9956 g, 7.368 mmol, 2.5 eq) were added. The reaction was agitated for 4 h. The reaction was monitored by Kaiser and chloranil tests. The resin was washed with DMF (3 times) and DCM (3 times). 20% piperidine in DMF was added to the resin and the reaction was agitated for 30 min. The resin was washed with DMF (2 times), 5% HOBT and DMF (2 times). This procedure was repeated for each of the following amino acids in the following order: Fmoc-Ile-OH, Fmoc-Tyr(tBu)-OH, Fmoc-Cys(Trt)-OH, Fmoc-Leu-OH, Fmoc-Gly-OH, Fmoc-Tyr(3-Cl)—OH, Fmoc-Hyp(tBu)-OH, Fmoc-Cys(Trt)-OH, Fmoc-d-Glu(OtBu)-OH, Fmoc-Tyr(tBu)-OH.

2) Synthesis of FITC-hexyl-FBP-p-XD-SP (8)

FBP-p-XD-SP (7) (0.4030 g, 0.3949 mmol, 1.0 eq) was suspended in DMF and Fmoc-6-Ahx-OH (0.4885 g, 1.3822 mmol, 3.5 eq), DIC (0.3058 mL, 1.9747 mmol, 5.0 eq) and HOBT (0.1334 g, 0.9874 mmol, 2.5 eq) were added to it. The reaction was agitated for 6 h and monitored by Kaiser test. The resin was washed with DMF (3 times) and DCM (3 times). 20% piperidine in DMF was added to the resin and the reaction was agitated for 30 min. The resin was washed with DMF (2 times), 5% HOBT and DMF (2 times). The resin was suspended in a mixture of DMSO and DIPEA (4:1). Fluorescein isothiocyanate (FITC, 0.6150 g, 1.5796 mmol, 4 eq) was added to the reaction and it was agitated overnight. The resin was washed with DMF (3 times) and DCM (3 times) to obtain FITC-hexyl-FBP-p-XD-SP. $(M+2H)^{2+}/2$: Expected—1011.4, Observed—1011.3.

3) Synthesis of FITC-Hexyl-Cyclic-FBP-p-XD (9)

Compound 8 was added to a solution of TFA, triisopropylsilane (TIS), ethanedithiol (EDT), and water (92.5:2.5:2.5:2.5, ~15 mL/g FITC-hexyl-FBP-p-XD-SP). The reaction was stirred for 1 h at room temperature. The mixture was filtered and the solution volume reduced. Diethylether was added to precipitate a solid. The mixture was centrifuged and supernatant was removed. The solid was washed with ether and dried.

The solid was dissolved in a mixture of DMSO and water (50:50) and the pH was increased to 5. The reaction was stirred for 12 h and monitored by HPLC. The reaction mixture was injected onto a reverse phase C4 preparative column. The mobile phase A was a mixture of 0.1% TFA/95% $H_2O$/5% ACN and mobile phase B was a mixture of 0.1% TFA/10% $H_2O$/90% ACN. Starting from 0% B, the fraction of B increased to 29% over 10 minutes, then from 29 to 33% B over 15 minutes and then from 33 to 100% B over the next 3 min. The column was washed with 100% B for 5 min and the % B was ramped to 0% in the next 2 min. The system was re-equilibrated at 0% B over 5 minutes (total time=35 min). The peptide eluted at a concentration of 31% B from the column. The fractions were collected and lyophilized. Yield=0.020 g. $(M+2H)^{2+}/2$: Expected—1010.4, Observed—1010.3%; purity=99.9%.

4) Synthesis of FITC-Hexyl-Cyclic-FBP-p-XD-DOTA (10)

Compound 9 is dissolved in DMF and DOTA(OtBu)$_3$-ONHS (2 eq) is added to the solution. The pH of the solution is increased to 8.8 and the reaction stirred for 3 h and monitored by HPLC. The product is dissolved in a solution of TFA, phenol, MSA, thioanisole and DCM (90:2.5:2.5:2.5:2.5) and allowed to react for 20 min. The solution is then concentrated under reduced pressure and cold diethylether added to precipitate a solid. The solid is filtered and then redissolved in ACN/water mixture and purified by by reverse phase chromatography.

5) Synthesis of FITC-Hexyl-Cyclic-FBP-p-XD-DOTA-Gd (11)

Compound 10 is dissolved in water and the pH is changed to 6.5 using 1N sodium hydroxide. Gadolinium (III) chloride hexahydrate (GdCl$_3$.6H$_2$O, 1 eq) is added to the solution and the pH is adjusted to 6.5 with 1N sodium hydroxide. The reaction is stirred for 1 h at room temperature and monitored by HPLC. Residual gadolinium (III) chloride is neutralized with ethylenediaminetetraacetic acid (EDTA, 0.25 eq). The reaction is stirred for 15 min. and the pH is adjusted to 6.5 with 1N sodium hydroxide. The neutralization is monitored by testing with xylenol orange. The product is isolated from solution and purified by reverse phase chromatography.

Example 8

Synthesis of Dual PET-Optical Agent, FITC-Hexyl-Cyclic-FBP-p-XD-DOTA-Cu (12)

To a solution of 200 µCi of $^{64}$CuCl$_2$ (80 µL) was added 15 µL of 3.1 mM FITC-hexyl-cyclic-FBP-p-XD-DOTA solution (10). The total volume was increased to 200 µL by addition of water and 1 M NaOH to adjust the pH to 6.5. The reaction was stirred at 50° C. for 60 min and monitored by reverse phase HPLC with gamma ray detection. The radiochemical purity by HPLC was >98%.

Example 9

Synthesis of Dual SPECT-Optical Agent, FITC-Hexyl-Cyclic-FBP-p-XD-DOTA-in (13)

The In-111 (InCl$_3$) is transferred into a vial using a 0.1 M NaOAc solution, pH 5.5. A 1 mM solution of peptide 10 is prepared in 0.1 M NaOAc, pH 5.5. 50 µL of the peptide 10 solution is added to the In-111 solution and stirred at 50° C. for an hour. The solution is checked by RP-TLC. If the reaction is not complete and free In-111 is observed, more peptide is added to the reaction mixture and the reaction mixture is stirred for another 30 min at 50° C. The solution is checked by RP-TLC and this procedure is repeated until almost no free In-111 is left. The solution is diluted in saline before injection into animals.

Example 10

Synthesis of Dual MR-Optical Agent, DOTA-Cyclic-FBP-p-XD-FITC-Gd (17)

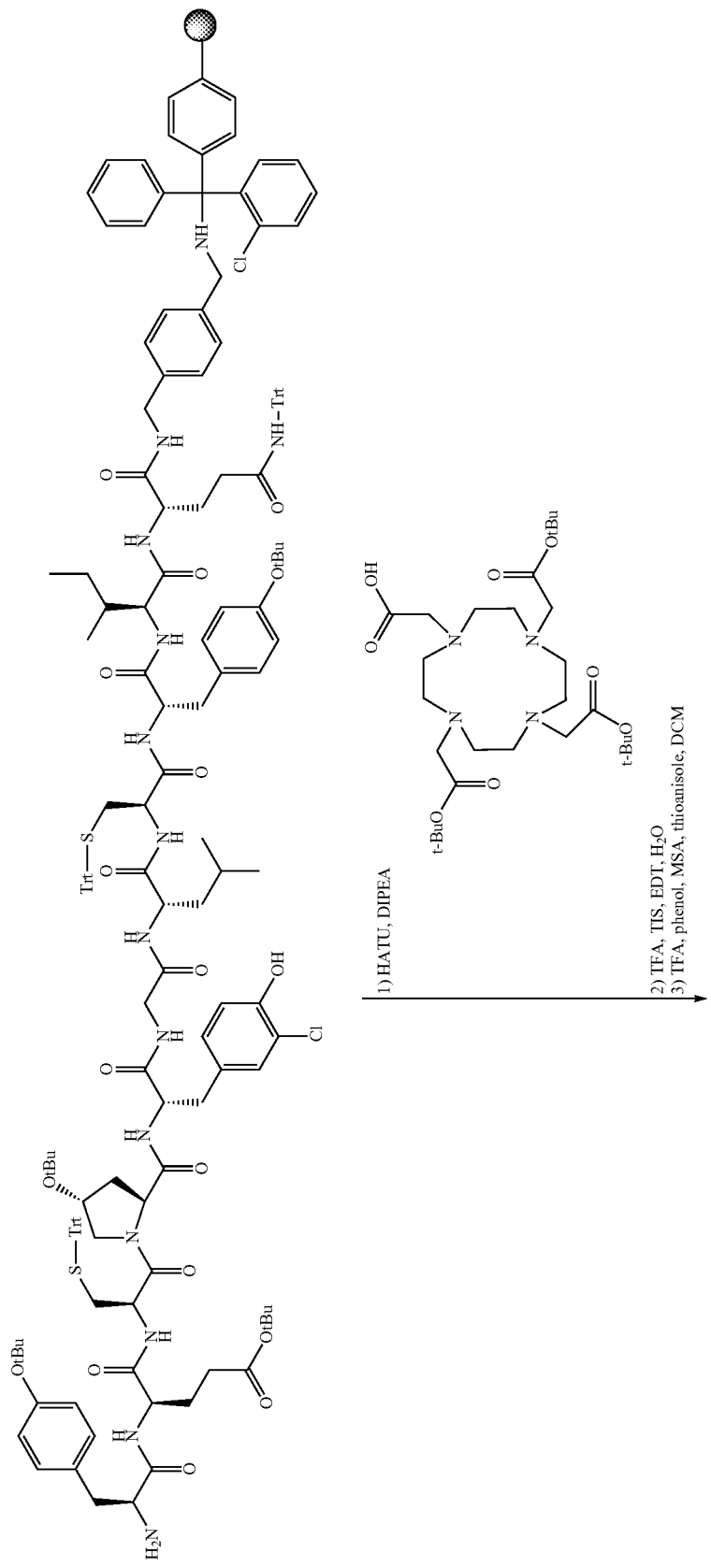
Scheme 8. Synthesis of DOTA-cyclic-FBP-p-XD-FITC (16)

-continued
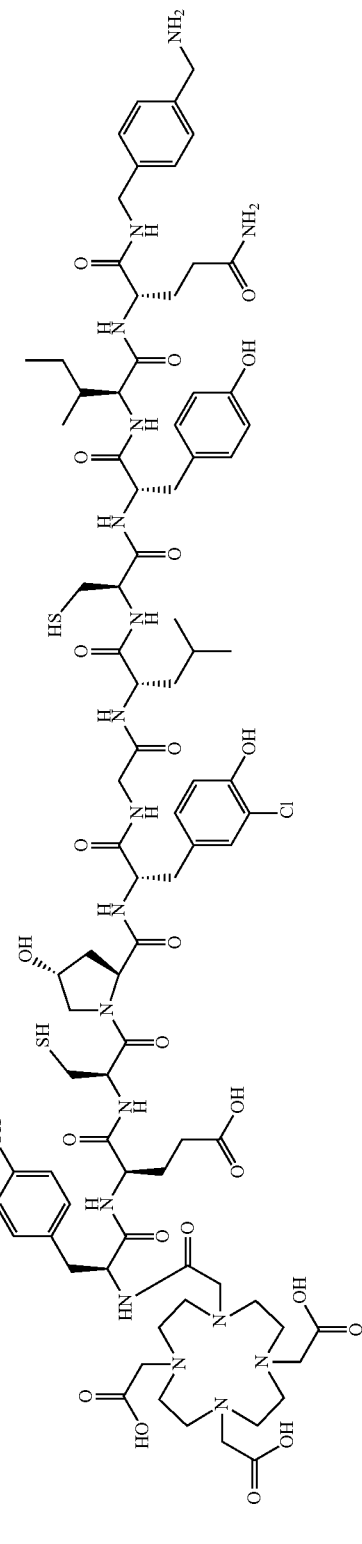
DOTA-FBP-p-XD (14)
↓ DMSO, pH 5
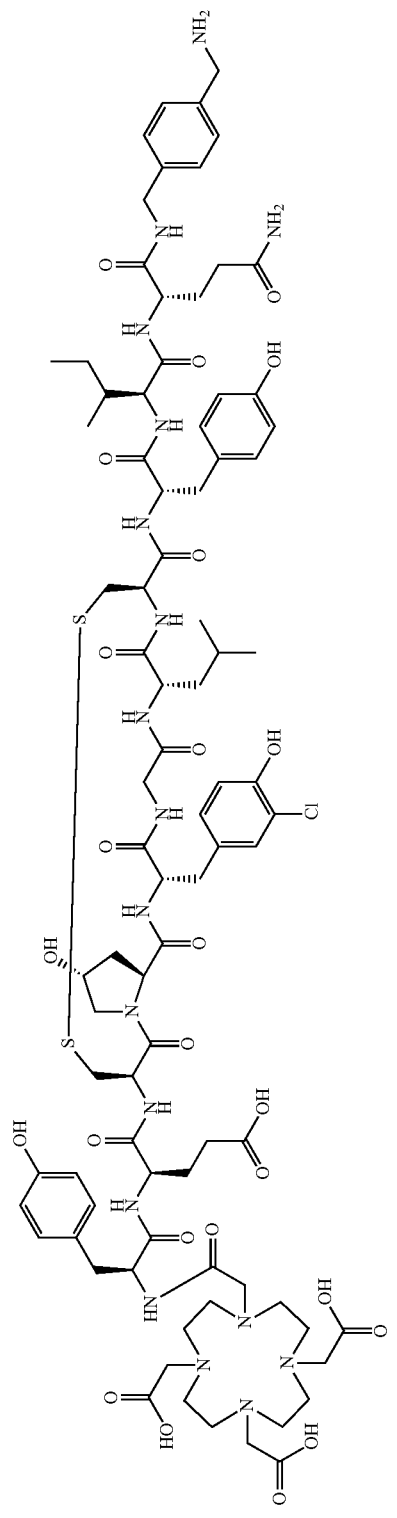
DOTA-cyclic-FBP-p-XD (15)
↓ 1) FITC, borate buffer, pH 9

-continued
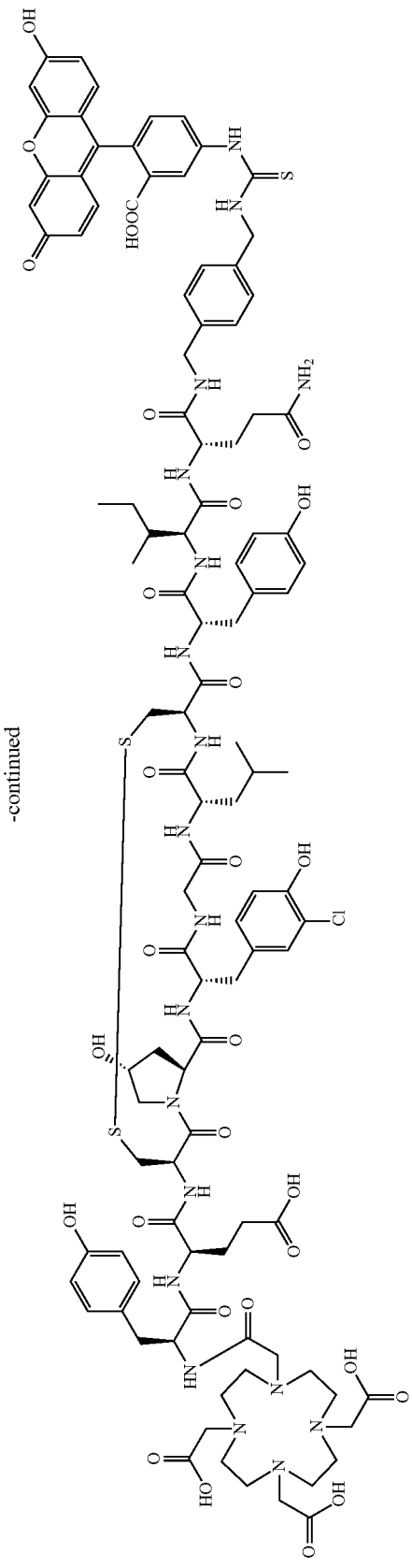
DOTA-cyclic-FBP-p-XD-FITC (16)

1) Synthesis of DOTA-FBP-p-XD (14)

Compound 7 (0.3224 g, 0.316 mmol, 1.0 eq) was suspended in DMF and DOTA(OtBu)$_3$-OH (0.5429 g, 0.9479 mmol, 3 eq), 2-(7-aza-1H-benzotriazole-1-yl) -1,1,3,3-tetramethyluronium hexafluorophosphate (HATU, 0.6008 g, 1.58 mmol, 5.0 eq) and DIPEA (0.550 mL, 3.16 mmol, 10 eq) were added to it. The reaction was agitated for 5 h and reaction checked by the Kaiser test. The resin was washed with DMF (3 times) and DCM (3 times).

The resin was added to a solution of TFA, TIS, EDT and water (92.5:2.5:2.5:2.5). The reaction was stirred for 1 h at room temperature. The mixture was filtered and the solution volume reduced. Diethylether was added to precipitate a solid. The mixture was centrifuged and supernatant was removed. The solid was washed with ether and dried. The solid obtained was dissolved in a solution of TFA, phenol, MSA, thioanisole and DCM (90:2.5:2.5:2.5:2.5). The reaction was stirred for 20 min. The solution was evaporated to a smaller volume. Diethylether was added to precipitate a solid. The mixture was centrifuged and supernatant was removed. The solid was washed with ether and dried under reduced pressure. $(M+2H)^{2+}/2$: Expected—953.4, Observed—952.9.

2) Synthesis of DOTA-Cyclic-FBP-p-XD (15)

Compound 14 was dissolved in a mixture of DMSO and water (60:40) and the pH was increased to 5. The reaction was stirred for 12 h and monitored by HPLC. The reaction mixture was injected onto a reverse phase C4 preparative column. The mobile phase A was a mixture of 0.1% TFA/95% H$_2$O/5% ACN and mobile phase B was a mixture of 0.1% TFA/10% H$_2$O/90% ACN. Starting from 0% B, the fraction of B increased to 29% over 10 minutes, then from 29 to 33% B over 15 minutes and then from 33 to 100% B over the next 3 min. The column was washed with 100% B for 5 min and the % B was ramped to 0% in the next 2 min. The system was re-equilibrated at 0% B over 5 minutes (total time=35 min). The peptide eluted off the column at a concentration of 30.4% B. Yield=0.0253 g $(M+2H)^{2+}/2$: Expected—951.9, Observed—952.4. % purity=87%.

3) Synthesis of DOTA-Cyclic-FBP-p-XD-FITC (16)

Compound 15 is dissolved in 0.05 M borate buffer, pH 9. FITC (2 eq) dissolved in DMF is added to the DOTA-cyclic-FBP-p-XD solution. The reaction is stirred for 3 h and monitored by HPLC. The peptide is purified by reverse phase chromatography.

4) Synthesis of GdDOTA-Cyclic-FBP-p-XD-FITC (17)

Compound 16 is dissolved in water and the pH is changed to 6.5 using 1N sodium hydroxide. Gadolinium (III) chloride hexahydrate (GdCl$_3$.6H$_2$O, 1 eq) is added to the solution and the pH is adjusted to 6.5 with 1N sodium hydroxide. The reaction is stirred for 1 h at room temperature and monitored by HPLC. Residual gadolinium (III) chloride is neutralized with ethylenediaminetetraacetic acid (EDTA, 0.25 eq). The reaction is stirred for 15 min. and the pH is adjusted to 6.5 with 1N sodium hydroxide. The neutralization is monitored by testing with xylenol orange. The product is isolated from solution and purified by reverse phase chromatography.

Example 11

Fibrinogen (fgn) (50 mg, American Diagnostica) was dissolved in 1 mL of TBS (50 mM Tris, 150 mM sodium chloride, pH 7.4) and was dialyzed against TBS with 5 mM sodium citrate. The concentration of the resulting fibrinogen solution was 8.8 mg/mL based on the absorbance at 280 nm where 1 mg/mL fgn has an optical density of 1.512 for a 1 cm path length. Solutions were prepared by diluting stock solutions of gadolinium probe and fgn to final solutions of 25 µM Gd and 5 mg/mL fgn. Gadolinium concentrations were determined by ICP-MS. Fibrin gels were prepared by adding CaCl$_2$ and thrombin to a final concentration of 7 mM and 4 U/mL, respectively. After briefly mixing the CaCl$_2$ and thrombin, the solutions were allowed to gel/clot for 30 minutes. After fibrin (fbn) formation was complete, the clots were pushed to the wall of the tube with a pipet tip. A total of 6×0.5 mL phantoms were prepared in 1 mL centrifuge tubes: A) pure water; B) 5 mg/mL fibrinogen; C) [Gd(HP-DO3A)] at 25 µM in 5 mg/mL fgn; D) [Gd(HP-DO3A)] at 25 µM in 5 mg/mL fbn gel; E) GdDOTA-cyclic-FBP-p-XD-FITC (compound 17) at 25 µM in 5 mg/mL fgn; F) GdDOTA-cyclic-FBP-p-XD-FITC (compound 17) at 25 µM in 5 mg/mL fbn gel.

All 6 phantoms were simultaneously imaged at room temperature at 1.5 T with a clinical MRI. T1-weighted gradient echo images were acquired with repetition time TR=9.2 ms, echo time TE=1.9 ms, flip angle=25°.

The images (FIG. 1) demonstrate that the dual probe is a better relaxation agent than commercial GdHP-DO3A and it can be used to visualize fibrin with MRI. Tubes A and B have similar signal intensity. For the fibrinogen solutions (B, C, E), the presence of gadolinium increases the signal intensity (C and E versus B). The tube with GdDOTA-cyclic-FBP-p-XD-FITC (E) is brighter than the tube with GdHP-DO3A (C) indicating that the former is a better relaxation agent. Tube D shows a uniform signal intensity indicating that the GdHP-DO3A is distributed equally between the clotted fibrin and the supernatant. On the other hand tube F with GdDOTA-cyclic-FBP-p-XD-FITC shows biphasic enhancement. On the right side of tube F the signal is more intense than in any of the other tubes while on the left side, the signal intensity is decreased relative to tube E. This indicates that GdDOTA-cyclic-FBP-p-XD-FITC is binding to the fibrin and the fibrin side of the tube is enriched with Gd resulting in greater signal intensity.

Example 12

Synthesis of Dual PET-Optical Agent, $^{64}$CuDOTA-Cyclic-FBP-p-XD-FITC (18)

To a solution of 200 µCi of $^{64}$CuCl$_2$ (80 µL) was added 35 µL of 0.872 mM DOTA-cyclic-FBP-p-XD-FITC (16). The total volume was increased to 200 µL by addition of water and 1 M NaOH to adjust the pH to 6.5. The reaction was stirred at 50° C. for 60 min and monitored by reverse phase HPLC with gamma ray detection. The radiochemical purity by HPLC was >98%.

Example 13

Phantom Study with PET $^{64}$CuDOTA was prepared by reacting 200 µCi of $^{64}$CuCl$_2$ with DOTA ligand (50 nmol) in 200 µL water at pH 6.5. The pH of the solution was maintained at 6.5 and the reaction was stirred at 50° C. for 30 min. The solution was then passed through a cation-exchange resin. The resin was washed with water and the total final volume was 600 µL.

Six phantoms were prepared in 4 mL glass culture tubes. Each phantom contained fibrinogen (fgn) at a final concentration of 2 mg/mL, 2.3 nmol of peptide or DOTA, a total volume of 2 mL, and a total activity of 150 nCi. In 3 of the phantoms, Fibrin gels (fbn) were prepared by adding CaCl$_2$ and thrombin to a final concentration of 7 mM and 4 U/mL, respectively. Once the clots had formed, the mixture was centrifuged and the clots settled to the bottom. The 6 phantoms were labeled: A) $^{64}$CuDOTA in fgn; B) $^{64}$CuDOTA in fbn gel; C) FITC-hexyl-cyclic-FBP-p-XD-$^{64}$CuDOTA (compound 12) in fgn; D) FITC-hexyl-cyclic-FBP-p-XD-$^{64}$CuDOTA (compound 12) in fbn gel E) $^{64}$CuDOTA-cyclic-FBP-p-XD-FITC (compound 18) in fgn; F) $^{64}$CuDOTA-cyclic-FBP-p-XD-FITC (compound 18) in fbn gel.

The 6 tubes were placed in a holder with each tube equidistant from the isocenter and PET data was collected for 15 minutes. PET imaging was performed on a human PET head scanner (BrainPET) at 21° C. The BrainPET gantry physical ID and OD are 36 cm and 60 cm, respectively. The axial field of view (FOV) is 19.25 cm and the transaxial FOV is ~30 cm. Each of the 32 PET detector modules consists of six 12×12 LSO crystal arrays read out by a 3×3 array of APDs (Hamamatsu 8664-55, Japan). The individual crystal size is 2.5×2.5×20 mm$^3$. The emission data recorded in list-mode format were sorted in the line of response space and compressed axially in the sinogram space for fast reconstruction. The normalization was calculated from a 64-hour scan of a plane-source rotated in the FOV. The images were reconstructed with the ordinary poisson ordered subsets expectation maximization (OP-OSEM) algorithm from prompts, variance reduced random coincidences, and normalization. The reconstructed volume consisted of 153 slices with 256×256 pixels (1.25×1.25×1.25 mm3).

Figure 2:
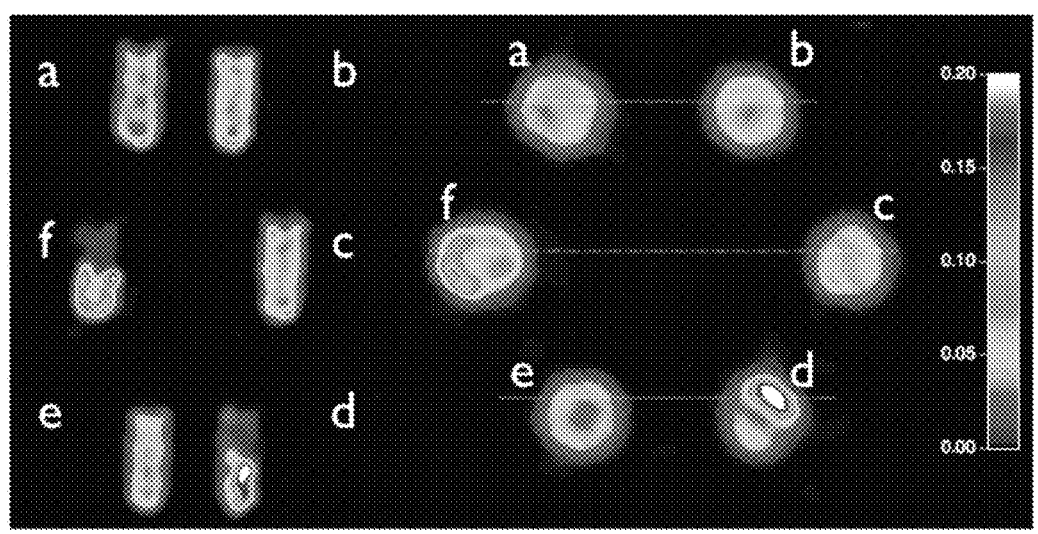
FIG. 2 shows phantoms imaged with PET. Activity in each sample was 150 nCi. At left are coronal images corresponding to the point indicated by the lines through the axial images (right hand side). A) $^{64}CuDOTA$ in fibrinogen; B) $^{64}CuDOTA$ in fibrin gel; C) FITC-hexyl-cyclic-FBP-p-XD-$^{64}CuDOTA$ (compound 12) in fibrinogen; D) FITC-hexyl-cyclic-FBP-p-XD-$^{64}CuDOTA$ (compound 12) in fibrin gel E) $^{64}CuDOTA$-cyclic-FBP-p-XD-FITC (compound 18) in fibrinogen; F) $^{64}CuDOTA$-cyclic-FBP-p-XD-FITC (compound 18) in fibrin gel.

The images (FIG. 2) demonstrate that the dual probes can visualize fibrin with PET. For the fibrinogen solutions (A, C, E), the $^{64}$Cu is distributed equally throughout the samples giving rise to uniform signal intensity. When the fibrinogen is clotted (tube B), there was no difference in the PET image between tubes A and B indicating that untargeted $^{64}$CuDOTA cannot be used to detect fibrin. The $^{64}$CuDOTA is distributed equally in the clot (bottom of tube B) and in the liquid above the clot. On the other hand, the fibrin-targeted dual probes both demonstrate an ability to detect fibrin. The $^{64}$CuDOTA experiment also demonstrates that clot formation does not physically trap the molecule. Tubes D and F indicate that radioactivity is centered in the bottom of each tube, i.e. in the clot, and very little activity remains in the liquid above the clot.

Example 14

Phantom Study with Fluorescence Imaging

A 10 mM solution of fluorescein was prepared in ethanol by adding 0.0113 g of fluorescein to 3 mL EtOH. This solution was diluted in water to prepare a 9.99 µM solution. Also, a dilute solution of GdDOTA-cyclic-FBP-p-XD-FITC was prepared with a final concentration of 8.55 µM. Four phantoms were prepared in 1 mL glass tubes. Each phantom contained fibrinogen at a final concentration of 2 mg/mL, 50 pmol of GdDOTA-cyclic-FBP-p-XD-FITC or fluorescein, at a total volume of 1 mL. In two of the phantoms, fibrin gels were prepared by adding CaCl$_2$ and thrombin to a final concentration of 7 mM and 4 U/mL, respectively. Once the clots had formed, the mixture was centrifuged and the clots settled to the bottom. The 4 phantoms were labeled: A) GdDOTA-cyclic-FBP-p-XD-FITC in fgn; B) GdDOTA-cyclic-FBP-p-XD-FITC in fbn gel; C) fluorescein in fbn gel D) fluorescein in fgn. The phantoms were imaged with an IVIS Spectrum imager.

Figure 3:
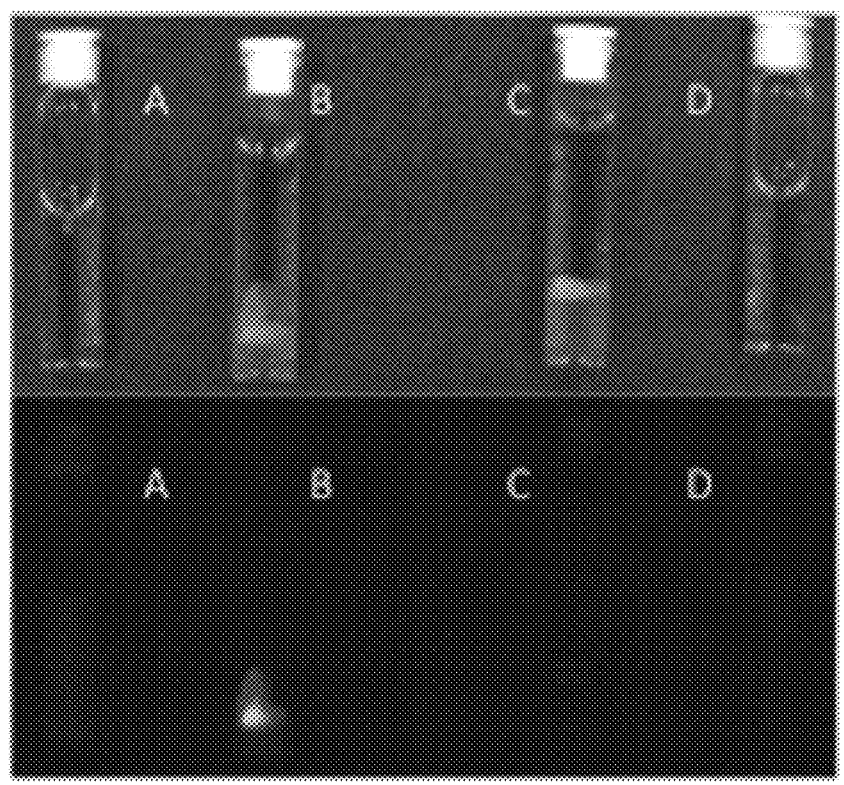
FIG. 3 illustrates phantoms imaged using fluorescence. Top row is a photograph of the 4 phantoms. Bottom row is the fluorescence signal overlaid on the photographic image. A) 50 nM GdDOTA-cyclic-FBP-p-XD-FITC (compound 17) in 2 mg/mL fibrinogen solution; B) 50 nM GdDOTA-cyclic-FBP-p-XD-FITC (compound 17) in 2 mg/mL fibrin gel; C) 50 nM fluorescein in 2 mg/mL fibrin gel D) 50 nM fluorescein in 2 mg/mL fibrinogen solution.

The images (FIG. 3) demonstrate that the dual probe can visualize fibrin with fluorescence imaging. For the fibrinogen solutions (A, D), the fluorescence intensity is distributed equally throughout the samples giving rise to uniform signal intensity. When the fibrinogen is clotted (tube B), the dual probe localizes in the fibrin clot and the fluorescence intensity is much higher in the clot. In the liquid around the clot the fluorescence intensity is reduced with respect to the fluorescence in Tube A. On the other hand, when fibrinogen is clotted in the presence of untargeted fluorescein (tube C), the fluorescence intensity is the same throughout the sample indicating little or no binding.

Example 15

Synthesis of Dual SPECT-Optical Agent, $^{111}$InDOTA-Cyclic-FBP-p-XD-FITC (19)

The $^{111}$InCl$_3$ is transferred into a vial using a 0.1 M NaOAc solution, pH 5.5. A 1 mM solution of peptide 16 is prepared in 0.1 M NaOAc, pH 5.5. 50 µL of the peptide 16 solution is added to the $^{111}$InCl$_3$ solution and stirred at 50° C. for an hour. The solution is checked by RP-TLC. If the reaction is not complete and free In-111 is observed, more peptide is added to the reaction mixture and the reaction mixture is stirred for another 30 min at 50° C. The solution is checked by RP-TLC and this procedure is repeated until almost no free In-111 is left. The solution is diluted in saline before injection into animals.

Example 16

Synthesis of Dual MR-PET Agent, Gd$_3$-EP-2104R-Cu (21)

1) Synthesis of Gd$_3$-EP-2104R (20)

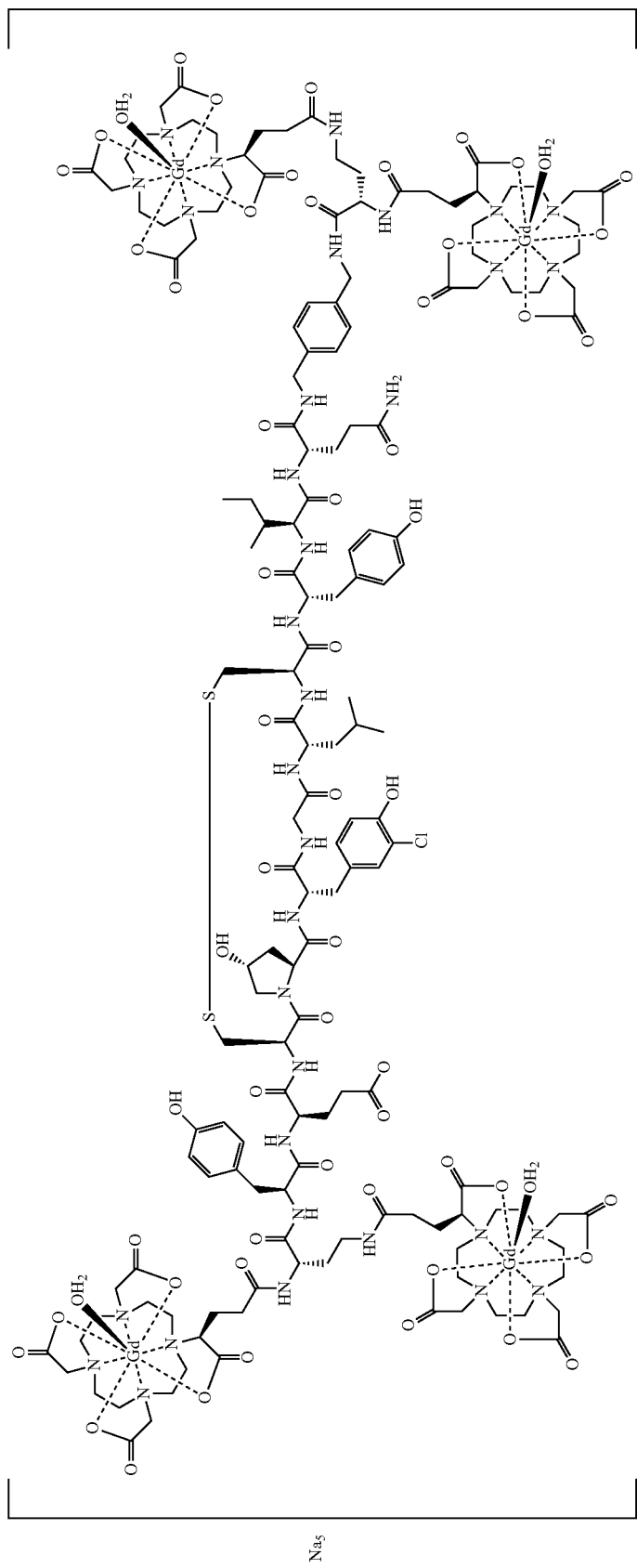

The fibrin-targeted MR probe EP-2104R was synthesized as described previously (Overoye-Chan K, Koerner S, Looby R J, et al. J Am Chem Soc. 2008 130(18):6025-39). EP-2104R (0.04 g, 8.32 μmol, 1 eq) was dissolved in 50 mM citric acid, pH 3. 0.666 mL of 50 mM DTPA (33.28 μmol, 4 eq) solution in water was added to the EP-2104R solution and pH was maintained at 3. The solution was stirred for 48 h and was monitored by HPLC on a $C_4$ column. The mobile phase A was 40 mM ammonium phosphate and 0.2 mM EDTA. The mobile phase B contained 70% MeOH and 30% A. Based on HPLC analysis, after 48 h, about 5% of the total Gd was removed from EP-2104R. The peptide was injected onto a $C_4$ reverse-phase column to remove the DTPA. The mobile phase A for this column was 95% $H_2O$/5% ACN and mobile phase B was 90% ACN/10% $H_2O$. The column was washed with A for the first five minutes. EP-2104R and Gd-depleted EP-2104R were eluted by increasing the percentage of B and were collected together. The ACN from the fractions was evaporated and the fractions were lyophilized. The product obtained weighed 0.0292 g.

2) Synthesis of $Gd_3$-EP-2104R-Cu (21)

To incorporate copper-64, 5 mg of Gd-depleted EP-2104R (20) was dissolved in 0.1 mL of water, and 2.5 mCi of $^{64}CuCl_2$ in 0.2 mL water was added. The pH of this solution was increased to 6.5 using 5 M NaOH. The reaction mixture was stirred at 50° C. for an hour. The reaction was monitored by reverse phase HPLC with a gamma detector. The reaction mixture was stirred with 4 equivalents of diethylenetriamine (dien) for 30 min at room temperature. The excess dien, free $Cu^{2+}$ and $Cu(dien)^{2+}$ were removed by cation exchange chromatography using Dowex-50 resin, sodium form. The radiochemical purity of the final solution was >98% as determined by HPLC. The specific activity of the dual PET-MR probe was 380±120 μCi/μmol. The solution was diluted with saline before injection into animals.

Example 17

Fibrin Binding of Cu-64 Labeled Probes

Fibrinogen from human plasma (Calbiochem) was dialyzed against 50 mM Tris, pH 7.4, 150 mM sodium chloride, 5 mM sodium citrate (TBS•citrate). The fibrinogen concentration was adjusted to 5 mg/mL and $CaCl_2$ was added (7 mM). The fibrinogen solution (50 μL) was dispensed into the wells of a 96-well polystyrene microplate (Immulon-II). A solution (50 μL) of human thrombin (2 U/mL) in TBS was added to each well to clot the fibrinogen. The plates were incubated at 37° C. and evaporated to dryness overnight. The plates were sealed with tape and stored at −20° C. until use. The wells with dried fibrin were incubated at 37° C. with known concentrations of the probes. The concentration of the unbound probe was determined by well counting. The concentration of the bound probe=[total]−[unbound]. The percentage bound probe was given by [(bound probe)/total probe)]×100.

% bound for $Cu_2$-bis-(DOTAGA(OH)$_4$)-FBP-mXD (5)=66%.

% bound for $Gd_3$-EP-2104R-Cu (21)=98.7%.

Example 18

MR-PET Imaging of Thrombus with $Gd_3$-EP-2104R-$^{64}$Cu

Animal Protocol.

All animal studies were approved by the Subcommittee on Research Animal Care at Massachusetts General Hospital. The occlusive thrombus model was described previously (Zhang R L, Chopp M, Zhang Z G, Jiang Q, and Ewing J R., *Brain Res.* 1997 766(1-2):83-92). Briefly, male Wistar rats (350-400 g, n=8; Charles River Laboratories, Wilmington, Mass.) were anaesthetized with isoflurane (1-2% in 70% $N_2O$ and 30% $O_2$) and body temperature was kept at 37.5° C. A day old autologous blood clot was injected into the right internal carotid artery (ICA) at the level of the middle cerebral artery (MCA). The femoral vein was cannulated for intravenous delivery of the contrast agent. Simultaneous PET and MR were acquired on a clinical 3T MRI-BrainPET scanner using a home-built receive surface coil and a CP transmit coil. After baseline MR scans were acquired, the dual MR-PET probe was injected at a dose of 11.5 μmol/kg (46 μmol Gd/kg, total activity=19.6±5.9 MBq). The animals were sacrificed 2 h post-injection. In total, six animals underwent imaging while in two additional animals only biodistribution data was collected.

General MR-PET Imaging Protocol.

The list-mode emission data from PET were rebinned in the sinogram space for fast reconstruction. The uncorrected PET volume was first reconstructed and binary segmented based on an empirically determined threshold in soft tissue and air. A uniform linear attenuation coefficient (0.096 cm$^{-1}$, corresponding to water at 511 keV) was assigned to all soft tissue voxels and the resulting attenuation map (combined with the coil attenuation map) was forward projected to derive the attenuation correction factors in sinogram space. A model-based approach was used to derive the scatter sinogram. The normalization was calculated from a 64 hr scan of a plane-source rotated in the FOV. The images were reconstructed with the ordinary Poisson ordered subsets expectation maximization (OP-OSEM) algorithm using 16 subsets and 6 iterations. The reconstructed volume consists of 153 slices with 256×256 pixels (1.25×1.25×1.25 mm$^3$). The spatial resolution at the center of the field of view is approximately 2.5 mm.

The emission data were recorded in list-mode format for approximately 90 min (9×10 min frames) after MR-PET probe administration. The data acquired in each individual frame were processed and images were reconstructed after acquisition for immediate analysis. Images were also reconstructed from the data acquired 30-90 minutes post injection. Additionally, thirty 3-minute frames were generated and the tracer uptake in structures of interest as a function of time was analyzed.

The MR imaging sequence included MP-RAGE and 3D T1-weighted gradient echo scans with and without inflow saturation. The latter were used for time of flight (TOF) angiography. The field of view scanned for the 3D sequences was 85×85 mm$^2$, with repetition time (TR), echo time (TE), and flip angle of 32 ms, 5.78 ms and 18°, respectively. The number of excitations (NEX) was 1 with a matrix size of 448×448×92 giving a resolution of 0.19 mm$^3$ in a scan time of 5 min, or 9:35 for the black blood sequence which used inferior and superior saturation to the null the inflowing arterial blood. For the MP-RAGE, the parameters used were inversion time TI=900 ms, TR/TE=2300/4.4, NEX=1, FOV=49×49 mm², matrix=192×192, slice thickness=0.26 mm for resolution=0.26 mm³.

Tissue and Blood Analysis.

The ipsilateral (containing the thrombus) and contralateral ICA and MCA, cerebral hemispheres, blood, urine, intraabdominal organs, rectus femoris muscle and femur bone were collected from all the animals, weighed and radioactivity measured on a gamma counter. The percent of the injected dose per gram of tissue (% ID/g) was calculated by dividing the counts of $^{64}Cu/g$ of tissue by the total counts of the injected dose, based on an aliquot of the injected dose, with correction for radioactive decay. Tissues were later homogenized in nitric acid and analyzed for Gd concentration by inductively coupled plasma-mass spectrometry (ICP-MS).

Image Analysis.

MR images were analyzed using OsiriX (www.osirix-viewer.com) by drawing regions of interest (ROI) in the thrombus, contralateral artery and adjacent tissue and quantifying signal intensity (SI). Noise was quantified as the standard deviation (SD) of the signal measured in the air outside the animal. Contrast to noise ratios (CNR) were calculated for the difference between tissue A and tissue B using the following equation (1).

$$\text{CNR(tissue } A/\text{tissue } B) = [\text{SI(tissue } A) - \text{SI(tissue } B)] / \text{SD(air)} \quad (1)$$

Signal intensity ratios (SIR) between the thrombus (ipsilateral) and contralateral vessel were calculated using equation (2) for images pre- and 10 min post-probe administration.

$$\text{SIR} = [\text{SI(ipsilateral)/SI(contralateral)}]_{post}/[\text{SI(ipsilateral)/SI(contralateral)}]_{pre} \quad (2)$$

For PET, the thirty datasets reconstructed from the three-minute frames were analyzed using Amide (Loening A M, Gambhir S S., *Mol Imaging* 2003 2(3):131-7). Volumes of interest (VOI) were drawn in the thrombus and in the same area on the contralateral side. Average uptake was quantified in both VOI for the same slice and the ratio of ipsilateral to contralateral uptake was calculated. Time activity curves were also calculated for the thrombus, contralateral artery, liver and kidney.

Results.

Figure 4:
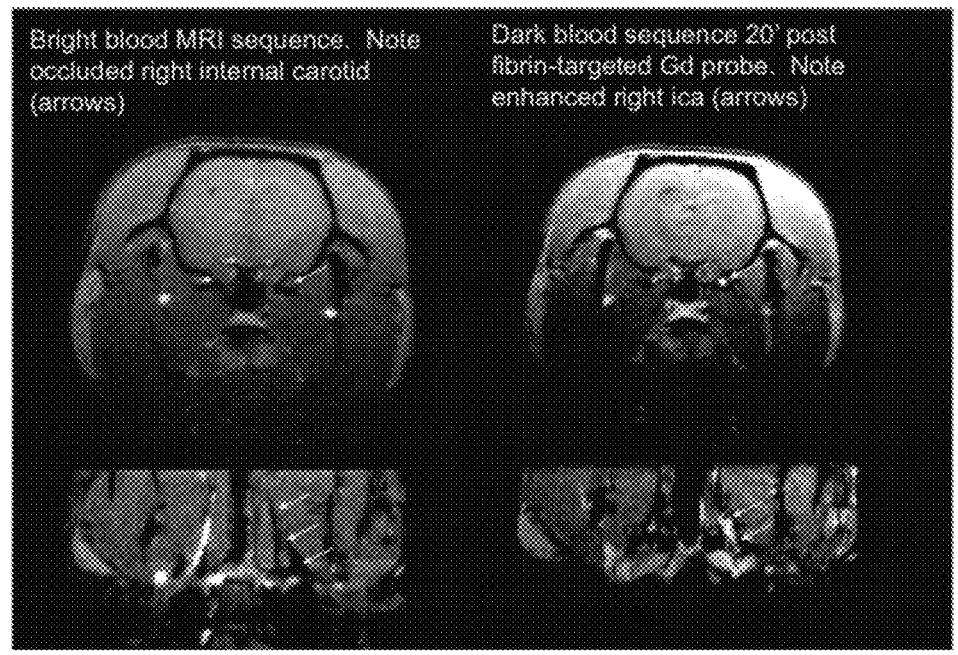
FIG. 4 shows images at the top that are orthogonal reformats of the corresponding image immediately below it. Left: rat with occlusive thrombus in right internal carotid artery (ica). Time of flight angiography shows a flow deficit on the right side indicated by the arrows. Flowing blood appears bright in this image. Right: Black blood T1-weighted MRI post injection of dual probe 21. The region that showed no flow on the angiographic image is now bright indicating the presence of thrombus.

Time of flight MR angiography (FIG. 4, right) showed restricted flow to the right side of the brain in all animals imaged, consistent with an occlusive thrombus. In all six animals imaged the thrombus was clearly visible on black-blood MR images post injection of the dual probe with relatively high contrast compared to adjacent tissue (FIG. 4, left). The CNR post probe was much higher than the CNR measured on the pre-injection images ($CNR_{thrombus:brain}=3.0±2.0$ post vs $-2.0±2.2$ pre, $p<0.005$).

This demonstrates that the dual probe can detect thrombi using MRI and that combining an angiographic image with the image after the targeted probe is injected provides more certainty as to the precise location of the enhancing thrombus.

Figure 5:
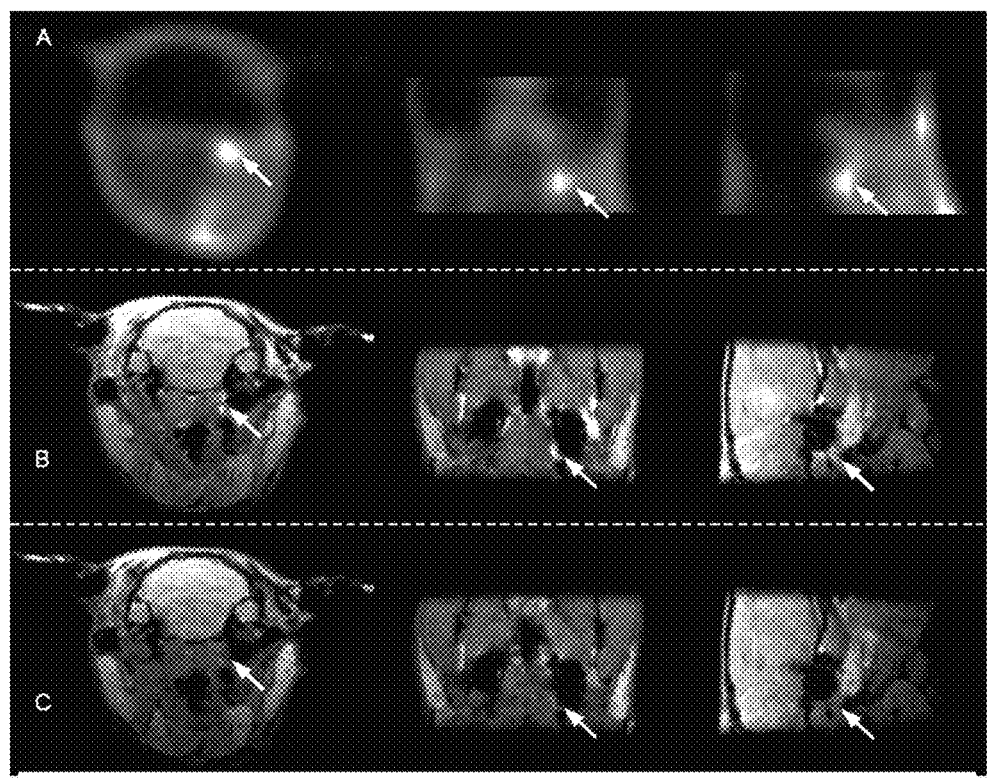
FIG. 5 illustrates orthogonal multiplanar co-registered images covering the MR field of view. A) PET images reconstructed from data 30-90 min post probe; B) T1-weighted black blood MR images post probe; C) T1-weighted black blood MR images pre-probe. Arrows denote increased PET signal (A) that is hyperintense on MR post probe (B) but not on MR pre-probe (C) and which corresponds to thrombus in the right

FIG. 5 shows multiplanar MR black blood pre-probe (FIG. 5C), MR black blood post probe (FIG. 5B) and PET images post probe (FIG. 5A) from co-registered data sets for the MR field of view. The focal increased signal on the PET images (FIG. 5A) corresponds to a region that is hyperintense on T1-weighted MR post probe injection (FIG. 5B) but is absent on pre-probe MR (FIG. 5C). The PET data were analyzed by computing a signal intensity ratio ($SIR_{ipsi:contra}$) between the hyperintense lesion (ipsilateral) and an identical contralateral volume of interest. For PET, $SIR_{ipsi:contra}=1.85±0.48$, $p<0.01$ for null hypothesis of $SIR_{ipsi:contra}=1$. For the MR data SIR was computed analogously to the PET data for the pre and post probe scans. The ratio $SIR_{post}/SIR_{pre}=1.71±0.35$, $p<0.01$ for null hypothesis of $SIR_{post}/SIR_{pre}=1$.

This data (FIG. 5) shows that the dual probe enables thrombus detection with both modalities. In PET the thrombus was quite conspicuous but the lower spatial resolution of PET and the lack of anatomical landmarks in the PET image makes it more difficult to ascertain if the hyperintense signal is coming from an artery, a vein, or outside the vasculature. Combining this image with high resolution MRI confirms the presence of the thrombus and localizes it precisely within the internal carotid artery.

Figure 6:
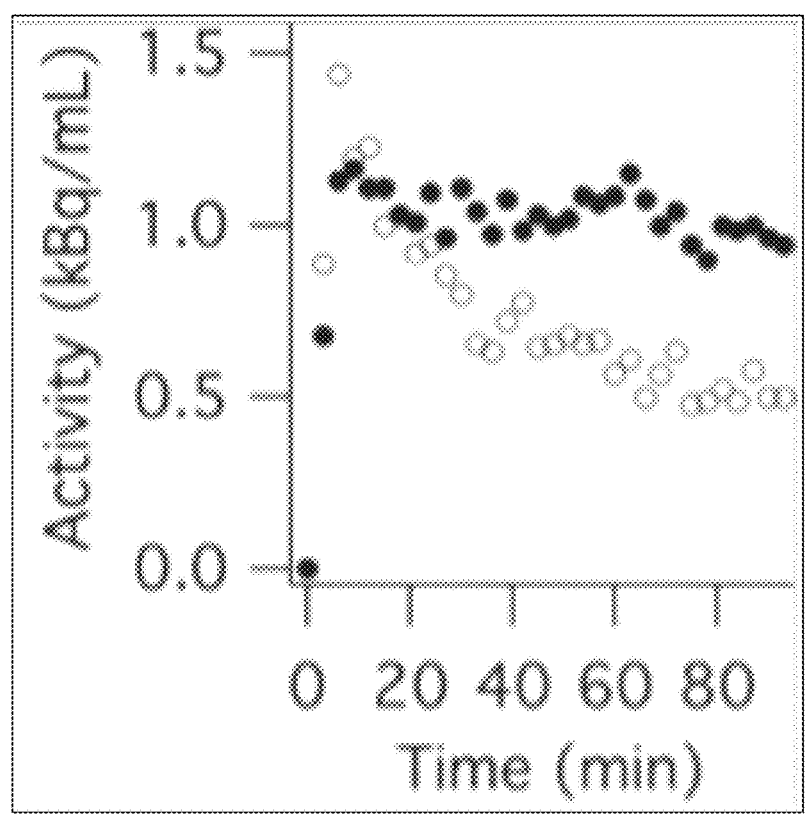
FIG. 6 shows time activity curves after injection of dual probe 21 into a rat with occlusive thrombus in the right ica. Time-activity curves for the thrombus (filled circles) and contralateral (left carotid) vessel (open circles) show rapid and static uptake in the thrombus while in the contralateral vessel activity is clearing with time.

Time-activity volume-of-interest curves for the thrombus and contralateral artery were calculated from the images. For the thrombus (FIG. 6) activity remains approximately constant over 90 min suggesting fibrin binding, while in the contralateral vessel the signal decays with time as the probe is cleared from the blood. The results show in FIG. 6 indicate that thrombus conspicuity measured by thrombus to background tissue activity is greatest at late time points. This is a benefit of using a $^{64}Cu$ labeled probe with a relatively long radioactive half-life wherein delayed imaging is feasible at several hours post injection.

The ex vivo $^{64}Cu$ and Gd tissue analyses were consistent with the imaging results. The % ID/g of $^{64}Cu$ was the greatest in the kidney, followed by the liver and the thrombus. The concentration of $^{64}Cu$ in the thrombus was at least 4-fold higher than in the contralateral vessel, blood plasma, brain, or muscle ($p<0.005$). The gadolinium findings generally mirrored the $^{64}Cu$ results. Outside the kidney, the highest Gd concentration was in the thrombus and here it was over 6-fold higher compared to the contralateral vessel, blood plasma, brain, or muscle ($p<0.0001$). These results quantitatively show that the dual probe targets thrombus in vivo.

Example 19

Figure 7:
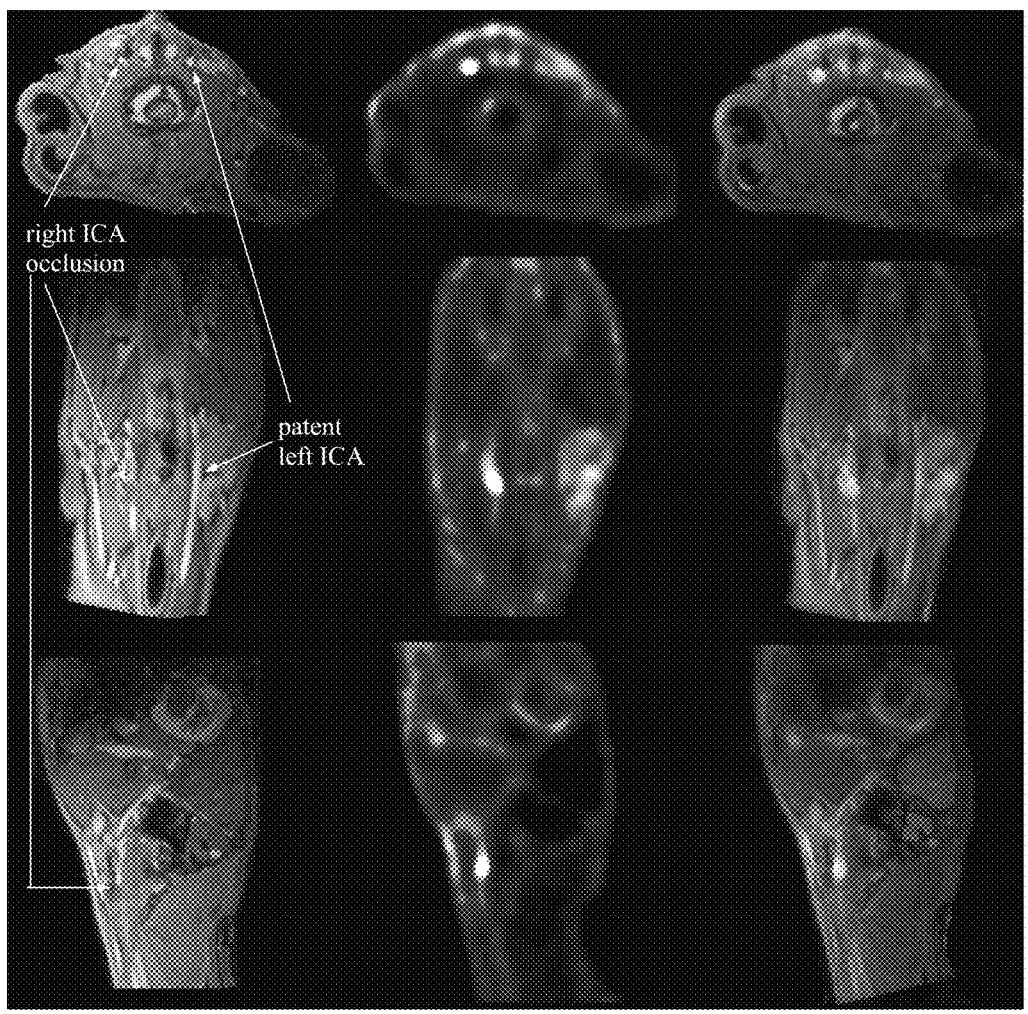
FIG. 7 illustrates a hyperintense PET signal in the right internal carotid (ICA) after intravenous injection of dual probe 21 into a rabbit with occlusive thrombus in the right ICA. From top to bottom: three orthogonal views (axial, coronal, sagittal) of a rabbit neck. Left: MR angiogram acquired after injection of blood pool MR contrast agent gadofosveset. Contrast agent makes arteries and veins appear bright. Note signal void in right internal carotid artery (arrows). Middle: PET post $^{64}Cu$-labeled compound 21. Note the region of high activity; Right: merged MR-PET image shows localization of hyperintense PET signal to area of right internal carotid artery (ICA) occlusion.

MR-PET Imaging of Thrombus with $Gd_3$-EP-2104R-$^{64}Cu$ (21) in a Rabbit Model of Occlusive Arterial Thrombus The occlusive thrombus model was similar to the one described above. Briefly, a male New Zealand white rabbit (2.5 kg) was sedated with a mixture of ketamine and xylazine and anaesthetized with isoflurane (1-2% in 70% $N_2O$ and 30% $O_2$) and body temperature was kept at 37.5° C. A day old autologous blood clot was injected into the right internal carotid artery (ICA). The femoral vein was cannulated for intravenous delivery of the imaging agents. Simultaneous PET and MR were acquired on a clinical 3T MRI-BrainPET scanner using a home-built receive surface coil and a CP transmit coil. After baseline MR scans were acquired, the compound 21 was administered at a dose of 300 mCi. The blood pool MR contrast agent gadofosveset was injected at a dose of 0.1 mmol Gd/kg to acquire an angiographic image. FIG. 7 shows a hyperintense PET signal in the right internal carotid (ICA). MR with a blood pool agent shows localization of the PET signal to the right ICA. The PET intensity is focused in an area where the MR angiogram shows an occlusion. This demonstrates the benefit of using two different imaging modalities to 1) identify the thrombus using the probe 21 with the PET image and 2) precisely localize the hyperintense PET image within the vascular tree.

Example 20

Binding to Human Fibrin

Human fibrinogen (American Diagnostica) was dialyzed against 50 mM Tris, pH 7.4, 150 mM sodium chloride, 5 mM sodium citrate (TBS•citrate) prior to use. The fibrinogen concentration was adjusted to 5 mg/mL, and CaCl$_2$ was added (7 mM). The fibrinogen solution (50 µL) was dispensed into the wells of a 96-well polystyrene microplate (Immulon-II). A solution (50 µL) of human thrombin (2 U/mL) in TBS was added to each well to clot the fibrinogen and to yield a final fibrin concentration close to 2.5 mg/mL. The plates were incubated at 37° C. and evaporated to dryness overnight.

Solutions of compound ranging from 0.1 to 50 µM were added to each of the wells of the dried fibrin microtiter plate, and the plate was shaken for 2 h. After incubation, solution was removed and the concentration of unbound compound was determined from its radioactivity or by ICP-MS. The concentration of the fibrin bound species, [bound], was determined by [bound]=[total]−[unbound]. The binding data were fit to a stoichiometric binding model (Nair et al, *Angew. Chem. Int. Ed.* 2008 47: 4918-4921).

Binding data for the first binding event:
Compound 5, Kd=9.0±1.9 µM
Compound 17, Kd=0.8±0.3 µM
Compound 11, Kd=0.9±0.3 µM A number of embodiments of the invention have been described. Nevertheless, it will be understood that various modifications may be made without departing from the spirit and scope of the invention. Accordingly, other embodiments are within the scope of the following claims.

What is claimed is:

1. An imaging agent, or a pharmaceutically acceptable salt form thereof, comprising a fibrin binding peptide bound to two imaging reporters, wherein:

a) the fibrin binding peptide is:

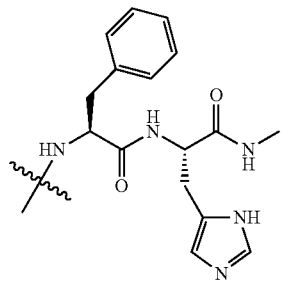

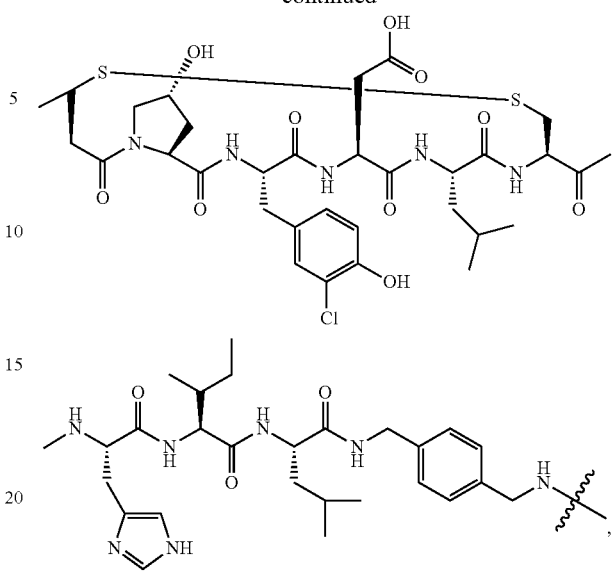

and b) each of the two imaging reporters is:

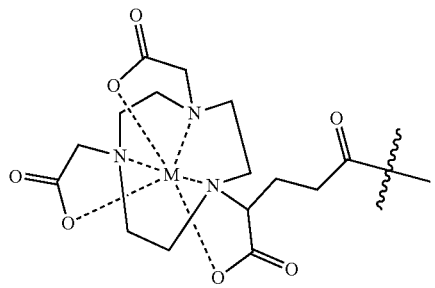

wherein M is $^{68}$Ga, or a pharmaceutically acceptable salt form thereof.

2. A pharmaceutical composition comprising an imaging agent and a pharmaceutically acceptable carrier, wherein the imaging agent comprises a fibrin binding peptide bound to two imaging reporters, wherein:

a) the fibrin binding peptide is:

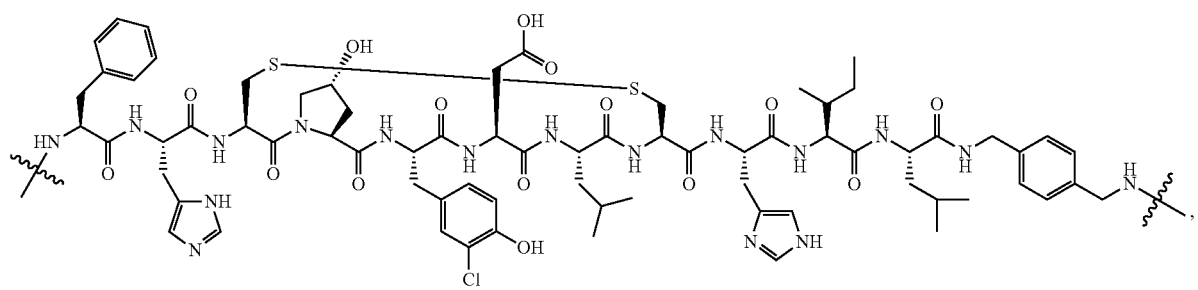 [SMILES: *NCc1ccc(CNC(=O)[C@H](CC(C)C)NC(=O)[C@@H](NC(=O)[C@H](Cc2c[nH]cn2)NC(=O)[C@@H]2CSSC[C@H](NC(=O)[C@H](Cc3cnc[nH]3)NC(=O)[C@H](Cc3ccccc3)N*)C(=O)N3C[C@H](O)C[C@H]3C(=O)N[C@@H](Cc3ccc(O)c(Cl)c3)C(=O)N[C@@H](CC(=O)O)C(=O)N[C@@H](CC(C)C)C(=O)N2)C(C)CC)cc1]

and
b) each of the two imaging reporters is:

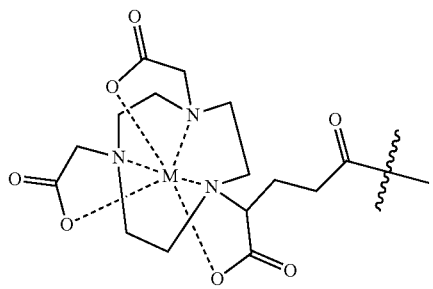

wherein M is $^{68}$Ga, or a pharmaceutically acceptable salt form thereof.

3. A method of imaging fibrin in a mammal, the method comprising:

a) administering to the mammal an imaging agent comprising a fibrin binding peptide bound to two imaging reporters, wherein:

i) the fibrin binding peptide is:

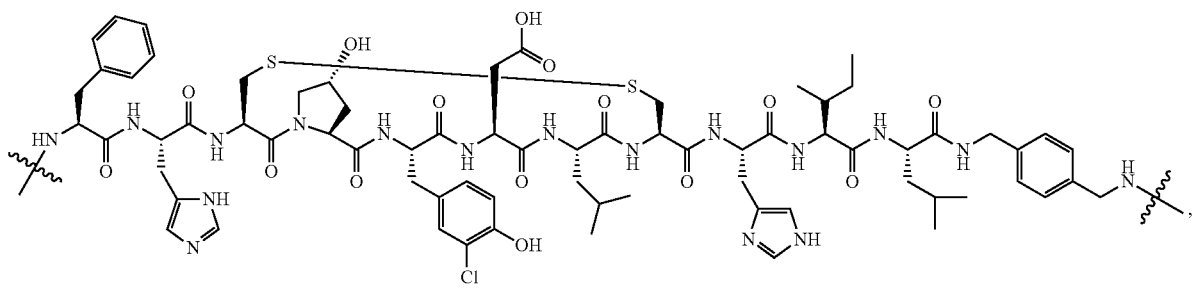 [SMILES: *NCc1ccc(CNC(=O)[C@H](CC(C)C)NC(=O)[C@@H](NC(=O)[C@H](Cc2c[nH]cn2)NC(=O)[C@@H]2CSSC[C@H](NC(=O)[C@H](Cc3cnc[nH]3)NC(=O)[C@H](Cc3ccccc3)N*)C(=O)N3C[C@H](O)C[C@H]3C(=O)N[C@@H](Cc3ccc(O)c(Cl)c3)C(=O)N[C@@H](CC(=O)O)C(=O)N[C@@H](CC(C)C)C(=O)N2)C(C)CC)cc1]

and ii) each of the two imaging reporters is:

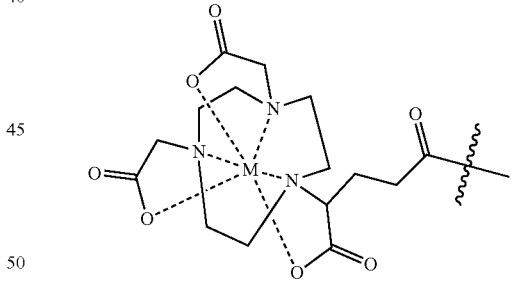

wherein M is $^{68}$Ga, or a pharmaceutically acceptable salt form thereof;
b) acquiring an image of the fibrin of the mammal using a nuclear imaging technique;
c) acquiring an anatomical image of the mammal using magnetic resonance imaging or computed tomography; and
d) overlaying the images of steps b) and c) to localize the image of fibrin within the anatomical image of the mammal.

4. The method of claim 3, wherein the nuclear imaging technique is selected from single photon emission computed tomography and positron emission tomography.

5. The method of claim 3, wherein the images of steps b) and c) are acquired simultaneously.

6. The method of claim 3, wherein the method further comprises administering to the mammal a second imaging agent, wherein the second imaging agent does not target fibrin.

7. The method of claim 6, wherein the second imaging agent is an MRI imaging agent selected from the group consisting of: gadoteridol, gadopentetate, gadobenate, gadoxetic acid, gadodiamide, gadoversetamide, gadoversetamide, and gadofosveset; or a CT imaging agent selected from the group consisting of iopamidol, iohexol, ioxilan, iopromide, iodixanol, ioxaglate, metrizoate, and diatrizoate.

8. An imaging agent, or a pharmaceutically acceptable salt form thereof, comprising a fibrin binding peptide bound to two imaging reporters, wherein:

a) the fibrin binding peptide is:

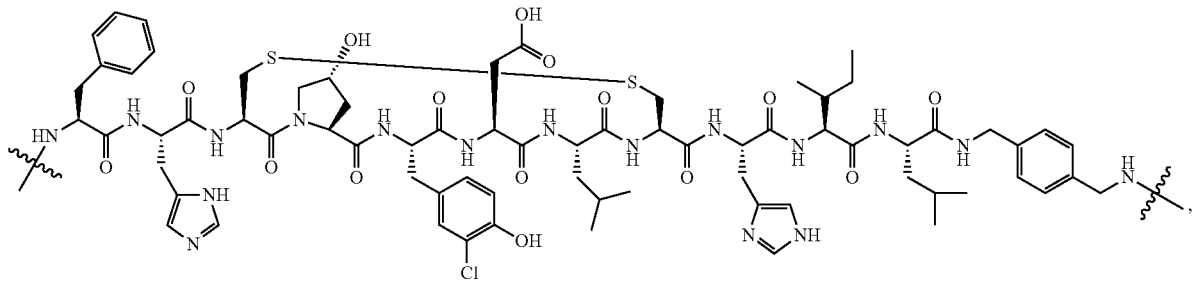 [SMILES: *NCc1ccc(CNC(=O)[C@H](CC(C)C)NC(=O)[C@@H](NC(=O)[C@H](Cc2c[nH]cn2)NC(=O)[C@@H]2CSSC[C@H](NC(=O)[C@H](Cc3cnc[nH]3)NC(=O)[C@H](Cc3ccccc3)N*)C(=O)N3C[C@H](O)C[C@H]3C(=O)N[C@@H](Cc3ccc(O)c(Cl)c3)C(=O)N[C@@H](CC(=O)O)C(=O)N[C@@H](CC(C)C)C(=O)N2)C(C)CC)cc1]

and b) each of the two imaging reporters is:

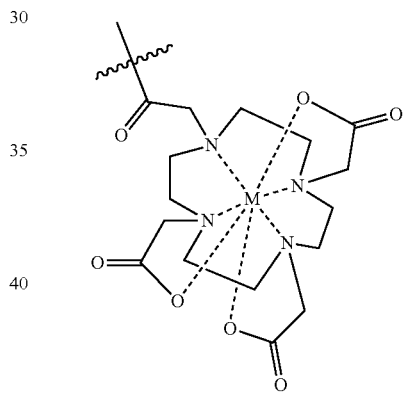

wherein M is $^{111}$In, or a pharmaceutically acceptable salt form thereof.

9. A pharmaceutical composition comprising an imaging agent and a pharmaceutically acceptable carrier, wherein the imaging agent comprises a fibrin binding peptide bound to two imaging reporters, wherein:

a) the fibrin binding peptide is:

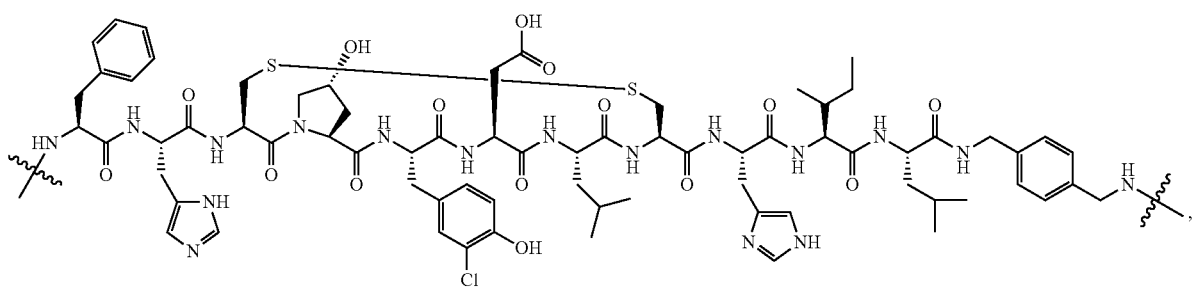 [SMILES: *NCc1ccc(CNC(=O)[C@H](CC(C)C)NC(=O)[C@@H](NC(=O)[C@H](Cc2c[nH]cn2)NC(=O)[C@@H]2CSSC[C@H](NC(=O)[C@H](Cc3cnc[nH]3)NC(=O)[C@H](Cc3ccccc3)N*)C(=O)N3C[C@H](O)C[C@H]3C(=O)N[C@@H](Cc3ccc(O)c(Cl)c3)C(=O)N[C@@H](CC(=O)O)C(=O)N[C@@H](CC(C)C)C(=O)N2)C(C)CC)cc1]

and
b) each of the two imaging reporters is:

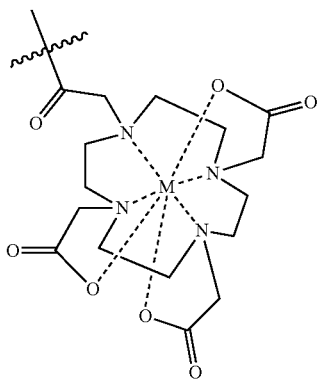

wherein M is $^{111}$In, or a pharmaceutically acceptable salt form thereof.

10. A method of imaging fibrin in a mammal, the method comprising:

a) administering to the mammal an imaging agent comprising a fibrin binding peptide bound to two imaging reporters, wherein:

i) the fibrin binding peptide is:

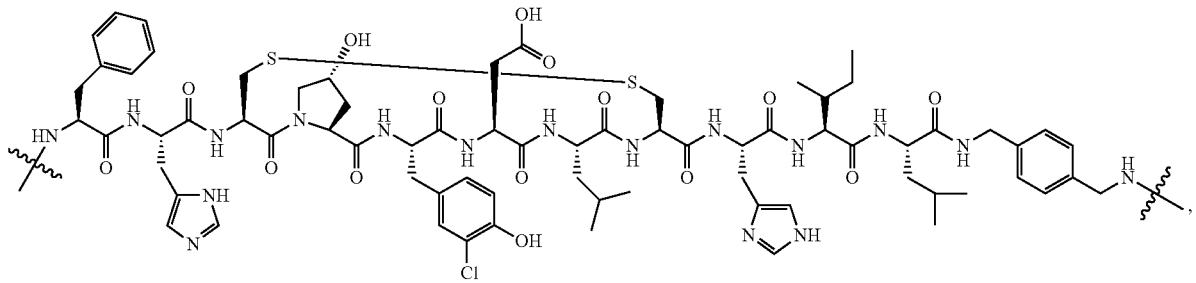 [SMILES: *NCc1ccc(CNC(=O)[C@H](CC(C)C)NC(=O)[C@@H](NC(=O)[C@H](Cc2c[nH]cn2)NC(=O)[C@@H]2CSSC[C@H](NC(=O)[C@H](Cc3cnc[nH]3)NC(=O)[C@H](Cc3ccccc3)N*)C(=O)N3C[C@H](O)C[C@H]3C(=O)N[C@@H](Cc3ccc(O)c(Cl)c3)C(=O)N[C@@H](CC(=O)O)C(=O)N[C@@H](CC(C)C)C(=O)N2)C(C)CC)cc1]

and
  ii) each of the two imaging reporters is:

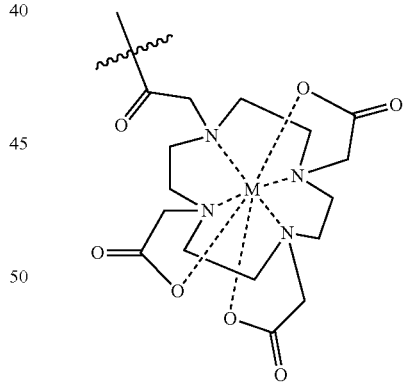

wherein M is $^{111}$In, or a pharmaceutically acceptable salt form thereof;
  b) acquiring an image of the fibrin of the mammal using a nuclear imaging technique;
  c) acquiring an anatomical image of the mammal using magnetic resonance imaging or computed tomography; and
  d) overlaying the images of steps b) and c) to localize the image of fibrin within the anatomical image of the mammal.

11. The method of claim 10, wherein the nuclear imaging technique is selected from single photon emission computed tomography and positron emission tomography.

12. The method of claim 10, wherein the images of steps b) and c) are acquired simultaneously.

13. The method of claim 10, wherein the method further comprises administering to the mammal a second imaging agent, wherein the second imaging agent does not target fibrin.

14. The method of claim 13, wherein the second imaging agent is an MRI imaging agent selected from the group consisting of: gadoteridol, gadopentetate, gadobenate, gadoxetic acid, gadodiamide, gadoversetamide, gadoversetamide, and gadofosveset; or a CT imaging agent selected from the group consisting of iopamidol, iohexol, ioxilan, iopromide, iodixanol, ioxaglate, metrizoate, and diatrizoate.

* * * * *

UNITED STATES PATENT AND TRADEMARK OFFICE
CERTIFICATE OF CORRECTION

| | | |
|---|---|---|
| PATENT NO. | : 9,889,213 B2 | Page 1 of 1 |
| APPLICATION NO. | : 14/954236 | |
| DATED | : February 13, 2018 | |
| INVENTOR(S) | : Peter D. Caravan | |

It is certified that error appears in the above-identified patent and that said Letters Patent is hereby corrected as shown below:

On the Title Page

Item (56) Other Publications, Column 2, Line 10, delete "US1010/031396." and insert -- US2010/031396 --, therefor.

In the Claims

Column 101, Lines 38-48 to Column 102, Lines 1-23, in Claim 1, replace

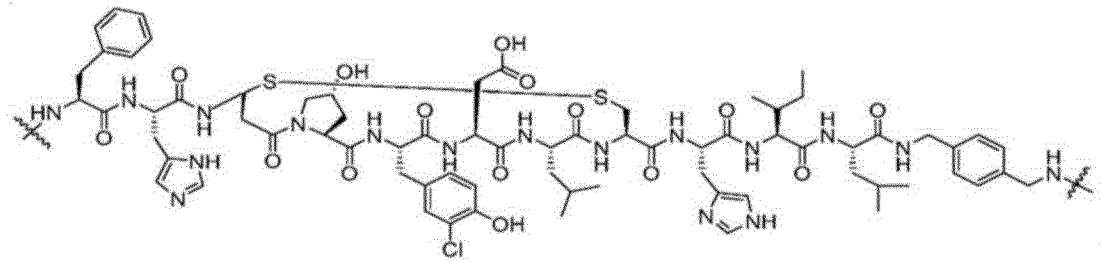

with

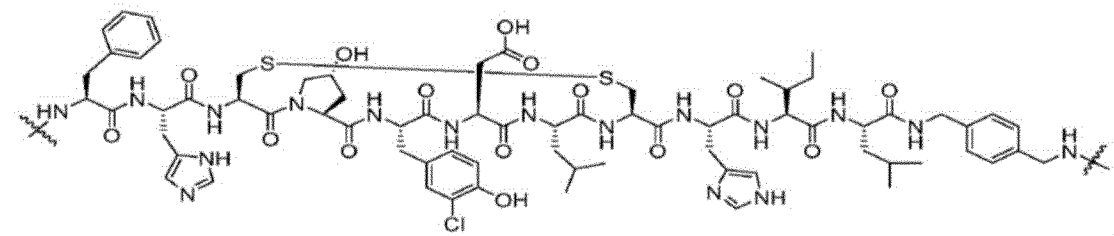

therefor.

Column 105, Line 8 - Column 106, Line 1, in Claim 7, delete "gadoversetamide, gadoversetamide," and insert -- gadoversetamide, --, therefor.

Column 109, Lines 10-11, in Claim 14, delete "gadoversetamide, gadoversetamide," and insert -- gadoversetamide, --, therefor.

Signed and Sealed this
Twenty-first Day of May, 2019

Andrei Iancu
*Director of the United States Patent and Trademark Office*